United States Patent
Sears

(10) Patent No.: US 11,700,810 B2
(45) Date of Patent: Jul. 18, 2023

(54) TRITICALE CULTIVAR 343CMS AND NOVEL SEQUENCES FOR MALE STERILITY

(71) Applicant: Northern Agri Brands LLC, Butte, MT (US)

(72) Inventor: Rollin George Sears, Junction City, KS (US)

(73) Assignee: Northern Agri Brands LLC, Butte, MT (US)

( * ) Notice: Subject to any disclaimer, the term of this patent is extended or adjusted under 35 U.S.C. 154(b) by 131 days.

(21) Appl. No.: 16/949,918

(22) Filed: Nov. 20, 2020

(65) Prior Publication Data
US 2021/0153449 A1 May 27, 2021

Related U.S. Application Data

(60) Provisional application No. 62/938,690, filed on Nov. 21, 2019.

(51) Int. Cl.
*A01H 5/10* (2018.01)
*A01H 6/46* (2018.01)

(52) U.S. Cl.
CPC ............. *A01H 6/4672* (2018.05); *A01H 5/10* (2013.01)

(58) Field of Classification Search
CPC .................... C12N 15/8289; A01H 6/4678
See application file for complete search history.

(56) References Cited

U.S. PATENT DOCUMENTS

| 6,297,012 | B1 | 10/2001 | Nakajima et al. |
| 11,124,797 | B1* | 9/2021 | Fu ........................ C12N 15/113 |
| 2007/0020621 | A1 | 1/2007 | Boukharov et al. |
| 2007/0074302 | A1 | 3/2007 | Matchett |

FOREIGN PATENT DOCUMENTS

WO 2018102816 A1 6/2018

OTHER PUBLICATIONS

Lamattina et al., "Higher plant mitochondria encode an homologue of the nuclear-encoded 30-kDa subunit of bovine mitochondrial complex 1", Eur. J. Biochem., vol. 217, pp. 831-838, 1993.
International Searching Authority in connection with PCT/US2020/061492 filed Nov. 20, 2020, "The International Search Report and the Written Opinion of the International Searching Authority, or the Declaration", 25 pages, dated Mar. 23, 2021.
Northern Agri Brands, LLC, "Application for Plant Variety Protection Certificate", 6 pages, May 24, 2019.
Hanson et al., "Interactions of Mitochondrial and Nuclear Genes That Affect Male Gametophyte Development", The Plant Cell., vol. 116, 17 pages. 2004.
Sinha et al., "Association of nad7a Gene with Cytoplasmic Male Sterility in Pigeonpea", The Plant Genome, vol. 8, No. 2, 13 pages. Jul. 10, 2015.

* cited by examiner

*Primary Examiner* — Weihua Fan
(74) *Attorney, Agent, or Firm* — McKee, Voorhees & Sease, PLC

(57) ABSTRACT

A cytoplasmic male sterile triticale cultivar, designated 343CMS, is disclosed. The invention relates to the seeds of triticale cultivar 343CMS, to the plants of triticale 343CMS, and to methods for producing a triticale plant produced by crossing the cultivar 343CMS with itself or another triticale variety. The invention also relates to methods for producing a triticale plant containing in its genetic material one or more transgenes and to the transgenic triticale plants and plant parts produced by those methods. The invention also relates to triticale varieties or breeding varieties and plant parts derived from triticale cultivar 343CMS, to methods for producing other triticale varieties, lines or plant parts derived from triticale cultivar 343CMS, and to the triticale plants, varieties, and their parts derived from the use of those methods. The invention further relates to hybrid triticale seeds and plants produced by crossing the cultivar 343CMS with another triticale cultivar.

21 Claims, 4 Drawing Sheets
Specification includes a Sequence Listing.

```
Cox3_1   GGGGTTTTAG  ATGGTTGGGA  AATGGGTGTT  GTTAATAGGG  GTATTGTGGG  420
Cox3_2   GGTGTTTTAG  ATGGTTGGGA  AATGGGTGTT  GTTAATAGGG  GTATTGTGGG  417
Cox3_3   GGGGTTTTAG  ATGGTTGGGA  AATGGGTGTT  GTTAATAGGG  GTATTGTGGG  419
Cox3_4   GGTGTTTTAG  ATGGTTGGGA  AATGGGTGTT  GTTAATAGGG  GTATTGTGGG  422
Cox3_5   GGTGTTTTAG  ATGGTTGGGA  AATGGGTGTT  GTTAATAGGG  GTATTGTGGG  419
Cox3_6   GGG--TTTNN  ATGGTTGGGN  NNNGGNNNT-  GTTNANNGGG  GNNNTGNNGG  417
Cox3_7   GGGGTTTTAN  ATGGTTGGGA  AATGGGTGTT  GTTAATAGGG  GTATTGTGGG  421
Cox3_8   GGGGTTTTAG  ATGGTTGGGA  AATGGGTGTT  GTTAATAGGG  GTATTGTGGG  421
Cox3_9   GGGGTTTTAG  ATGGTTGGGA  AATGGGTGTT  GTTAATAGGG  GTATTGTGGG  422
Cox3_10  GGGGTTTTAG  ATGGTTGGGA  AATGGGTGTT  GTTAATAGGG  GTATTGTGGG  422
Cox3_11  GGNNNNTTNN  NGGGGNNAAA  NNNNNNNNN-  ----------  ----------  393
Cox3_13  GGGGTTTTAG  ATGGTTGGGA  AATGGGTGTT  GTTAATAGGG  GTATTGTGGG  422
Cox3_15  GGGGTTTTAG  ATGGTTGGGA  AATGGGTGTT  GTTAATAGGG  GTATTGTGGG  422
Cox3_16  AGTGTTANAG  ATNNATGNNN  AANTGGTTTT  GTAAAGAGGG  TTATTGGGGN  404
Cox3_17  GGGGTTTTAG  ATGGTTGGGA  AATGGGTGTT  GTTAATAGGG  GTATTGTGGG  422
Cox3_12  GGGGTTTTAN  ATGGTTGGGA  AATGGGTNTT  GTTAATAGGG  GTATTGTGGG  419
```

TRITICALE CULTIVAR 343CMS AND NOVEL SEQUENCES FOR MALE STERILITY

CROSS-REFERENCE TO RELATED APPLICATIONS

This application claims priority to provisional application U.S. Ser. No. 62/938,690, filed Nov. 21, 2019, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 19, 2020, is named 2020-11-19_SEARS_P12671W001_SEQLISTING ST25.txt and is 204,606 bytes in size.

BACKGROUND

Triticale (*Triticale hexaploide* L.) is a crop species resulting from a cross between wheat (*Triticum*) and rye (*Secale*). It is a man-made crop in that plant breeders must physically make crosses and then manipulate the resultant offspring to obtain a self-fertile plant. Triticales are agronomically desirable due to their ideal combinations of the yield and quality advantages of common wheat, and the hardiness, pest tolerance, and adaptability of rye.

Hybrids of wheat and rye date back to the late 1800's, however early attempts to cross wheat and rye produced only sterile offspring, so for many years triticale was only a scientific novelty. Fertile triticales capable of producing viable seed were virtually unknown until the late 1930's when a Swedish geneticist named Arne Muntzing produced fertile triticale by treating the hybrids with colchicines, which doubled the chromosome number allowing reproductive pairing and division to occur. With normal pairing and division, triticale could be reproduced through subsequent generations. Once a fertile hybrid of triticale was produced, it became possible to create new combinations between wheat and rye and to intercross triticale with various common wheat. Triticale became a new crop plant, similar to, but distinct from common wheat, rye, and other cereal grains in breeding, seed production, and use. Once created and reproduced, a triticale does not revert or break-down to its original wheat and rye components.

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinated if pollen from one flower is transferred to the same or another flower of the same plant or a genetically identical plant. A plant is cross-pollinated if the pollen comes from a flower on a genetically different plant. In certain species, such as *Brassica campestris*, the plant is normally self-sterile and can only be cross-pollinated. In predominantly self-pollinating species, such as soybeans, wheat, and cotton, the male and female plants are anatomically juxtaposed such that during natural pollination, the male reproductive organs of a given flower pollinate the female reproductive organs of the same flower. Triticale, as with wheat, is predominantly self-pollinating, though considerable outcrossing may occur. Male sterile triticale lines are useful in a hybrid production system.

SUMMARY

Provided here is triticale seed, a triticale plant, plant parts, a triticale cultivar and a method for producing a triticale plant. Further provided are methods of producing triticale seeds and plants by crossing a plant of the instant invention with another triticale plant. The cytoplasmic male sterile plant is useful in hybridization systems.

The compositions and methods relate to seeds of triticale line 343CMS, to the plants of triticale line 343CMS and to methods for producing a triticale plant produced by crossing the triticale 343CMS with itself or another triticale plant. Thus, any such methods using the triticale line 343CMS are part of this invention, including selfing after restoration of fertility, backcrosses, hybrid production, crosses to populations, and the like.

In another aspect, single trait converted plants of 343CMS are provided. The single transferred trait may preferably be a dominant or recessive allele. Preferably, the single transferred trait will confer such traits as herbicide resistance, insect resistance, resistance for bacterial, fungal, or viral disease, male fertility, male sterility, and industrial usage. The single trait may be a naturally occurring triticale gene or a transgene introduced through genetic engineering techniques.

In another aspect is provided regenerable cells for use in tissue culture of triticale plant 343CMS. The tissue culture will preferably be capable of regenerating plants having the physiological and morphological characteristics of the foregoing triticale plant, and of regenerating plants having substantially the same genotype as the foregoing triticale plant. Preferably, the regenerable cells in such tissue cultures will be embryos, protoplasts, meristematic cells, callus, plant clumps, pollen, ovules, pericarp, seeds, flowers, florets, heads, spikes, leaves, roots, root tips, anthers, stems, and the like. Still further, the present invention provides triticale plants regenerated from the tissue cultures of the invention.

Applicants have further identified novel sequence variants of mitochondrial genes that are associated with the male sterile phenotype present in variety 343CMS. Disclosed herein are novel sequences of mitochondrial Atp synthase 8-1 gene (Atp8-1), NAD9/NAD7 mitochondrial nicotinamide adenine dinucleotide dehydrogenase (NAD9), and NADH dehydrogenase subunit 4L (NAD4L) which may be used to introduce the male sterile phenotype into other wheat, triticale or cereal plants by back-crossing, transformation, gene editing and the like, or used as a marker to identify male sterile varieties for use and selection in breeding to develop further male sterile varieties.

The sequences include SEQ ID NOs: 32, 48, 64, 66, and 68, their conservatively modified variants, and sequences with 80, 85, 90, 95, 96, 97, 98 or 99 percent homology thereto which include the novel variant nucleotides of the disclosure including an Atp8-1 nucleic acid sequence associated with a male sterile phenotype comprising one or more of: a C at position 155, a C at position 176, an A at position 186 and/or a C at position 337 as depicted in FIG. 2; an NAD9 nucleic acid sequence associated with a male sterile phenotype comprising one or more of the following: a C at position 170, an A at position 187 and/or a G at position 338 as depicted in FIG. 3; and an NAD4L nucleic acid sequence associated with a male sterile phenotype comprising one or more of the following: a C at position 51, an A at position 54, a C at position 57, a G at position 61, a T at position 64, a C at position 69, a G at position 74, a G at position 75, an A at position 89, a G at position 93, an A at position 95, a G at position 97, an A at position 199, a C at position 202, an A at position 206, a T at position 207, a T at position 208, a G at position 210, an A at position 212, a G at position 213, a C at position 214, a C at position 215, a T at position 218, a C at position 219, a C at position 220, a T at position 221, a T at position 222, a C at position 223, a C at position 225, a T at position 226, a C at position 227, a G at position 237, and/or a C at position 238 as depicted in FIG. 4.

In some embodiments, the Atp8-1 nucleic acid sequence comprises one or more of: a C at position 56, a C at position 77, an A at position 87 and/or a C at position 238 when compared to wild type reference SEQ ID NO: 65 or as set forth in SEQ ID NO: 66. In some embodiments, the NAD9 nucleic acid sequence comprises one or more of: a C at position 118, an A at position 135 and/or a G at position 286 when compared to wild type reference SEQ ID NO: 67 or as set forth in SEQ ID NO: 68.

The sequences include SEQ ID NOs: 70 and 72, their conservatively modified variants, and sequences with 80, 85, 90, 95, 96, 97, 98 or 99 percent homology thereto which include the novel variant polypeptides of the disclosure including an Atp8-1 polypeptide associated with a male sterile phenotype comprising one or more of: a P residue at position 19, a P residue at position 26, a K residue at position 29, and/or a P residue at position 80 when compared to wild type reference SEQ ID NO: 69 or as set forth in SEQ ID NO: 70; and an NAD9 polypeptide sequence associated with a male sterile phenotype comprising one or more of the following: an H residue at position 40, an A residue at position 45 and/or an A residue at position 96 when compared to wild type reference SEQ ID NO: 71 or as set forth in SEQ ID NO: 72.

Compositions and methods for modulating male fertility in a plant are provided. Compositions comprise expression cassettes comprising one or more mitochondrial male-fertility polynucleotides, or fragments or variants thereof, operably linked to a promoter, wherein expression of the polynucleotide modulates the male fertility of a plant. Various methods are provided wherein the level and/or activity of a polynucleotide or polypeptide that influences male fertility is modulated in a plant or plant part. Methods for identifying and/or selecting plants plants that are homozygous or heterozygous for a mutation that induces male sterility are also provided. In addition to the exemplary aspects and embodiments described above, further aspects and embodiments will become apparent by study of the following descriptions.

BRIEF DESCRIPTION OF THE DRAWINGS

FIG. 1 is a graphic showing multiple sequence alignment at nucleotide level of the mitochondrial cytochrome coxidase III (Cox3) gene (SEQ ID NOs: 1-16). All the accessions used in the study are labelled 1 through 13 and 15 through 17 with gene prefix (sequence 14 is omitted here and in FIGS. 2-4). Triticale line 343CMS is shown at number 12. Sequence change of interest is highlighted with asterisk (*) and nucleotide position. Nucleotides 371-420 of SEQ ID NO: 1, nucleotides 368-417 of SEQ ID NO: 2, nucleotides 370-419 of SEQ ID NO: 3, nucleotides 373-422 of SEQ ID NO: 4, nucleotides 370-419 of SEQ ID NO: 5, nucleotides 371-417 of SEQ ID NO: 6, nucleotides 372-421 of SEQ ID NO: 7, nucleotides 372-421 of SEQ ID NO: 8, nucleotides 373-422 of SEQ ID NO: 9, nucleotides 373-422 of SEQ ID NO: 10, nucleotides 365-393 of SEQ ID NO: 11, nucleotides 373-422 of SEQ ID NO: 12, nucleotides 373-422 of SEQ ID NO: 13, nucleotides 355-404 of SEQ ID NO: 14, nucleotides 373-422 of SEQ ID NO: 15, and nucleotides 370-419 of SEQ ID NO: 16 are shown.

FIG. 2 is a graphic showing multiple sequence alignment at nucleotide level of the mitochondrial Atp synthase 8-1 gene (Atp8-1) (SEQ ID NOs: 17-32). All the accessions used in the study are labelled 1-13 and 15-17 with gene prefix. Triticale line 343CMS is number 12. Sequence change of interest is highlighted with asterisk (*) and nucleotide position. Nucleotides 144-193 and 294-343 of SEQ ID NO: 17, nucleotides 136-185 and 286-335 of SEQ ID NO: 18, nucleotides 137-186 and 287-336 of SEQ ID NO: 19, nucleotides 135-184 and 285-334 of SEQ ID NO: 20, nucleotides 130-179 and 280-329 of SEQ ID NO: 21, nucleotides 136-185 and 286-335 of SEQ ID NO: 22, nucleotides 136-185 and 286-335 of SEQ ID NO: 23, nucleotides 136-185 and 286-335 of SEQ ID NO: 24, nucleotides 137-186 and 287-336 of SEQ ID NO: 25, nucleotides 137-186 and 287-336 of SEQ ID NO: 26, nucleotides 139-188 and 289-338 of SEQ ID NO: 27, nucleotides 143-192 and 293-342 of SEQ ID NO: 28, nucleotides 137-186 and 287-336 of SEQ ID NO: 29, nucleotides 61-63 and 119-168 of SEQ ID NO: 30, nucleotides 136-185 and 286-335 of SEQ ID NO: 31, and nucleotides 139-188 and 289-338 of SEQ ID NO: 32 are shown.

FIG. 3 is a graphic showing multiple sequence alignment at nucleotide level of the mitochondrial NAD9/NAD7 mitochondrial nicotinamide adenine dinucleotide dehydrogenase (NAD9) gene (SEQ ID NOs: 33-48). All the accessions used in the study are labelled 1-13 and 15-17 with gene prefix. Triticale 343CMS is number 12. Sequence change of interest is highlighted with asterisk (*) and nucleotide position. Nucleotides 150-195 and 296-345 of SEQ ID NO: 33, nucleotides 146-191 and 292-341 of SEQ ID NO: 34, nucleotides 147-192 and 293-342 of SEQ ID NO: 35, nucleotides 147-192 and 293-342 of SEQ ID NO: 36, nucleotides 117-132 and 213-240 of SEQ ID NO: 37, nucleotides 147-192 and 293-342 of SEQ ID NO: 38, nucleotides 147-192 and 293-342 of SEQ ID NO: 39, nucleotides 146-195 and 296-345 of SEQ ID NO: 40, nucleotides 151-200 and 301-350 of SEQ ID NO: 41, nucleotides 144-193 and 294-343 of SEQ ID NO: 42, nucleotides 146-195 and 296-345 of SEQ ID NO: 43, nucleotides 146-195 and 296-345 of SEQ ID NO: 44, nucleotides 147-196 and 297-346 of SEQ ID NO: 45, nucleotides 144-192 and 286-308 of SEQ ID NO: 46, nucleotides 147-196 and 297-346 of SEQ ID NO: 47, and nucleotides 148-197 and 298-347 of SEQ ID NO: 48 are shown.

FIG. 4 is a graphic showing multiple sequence alignment at nucleotide level of the mitochondrial NADH dehydrogenase subunit 4L (NAD4L) gene (SEQ ID NOs: 49-64). All the accessions used in the study are labelled 1 through 17 with gene prefix. Triticale line 343CMS is number 12. Sequence change of interest is highlighted with asterisk (*) and nucleotide position. Nucleotides 45-94 and 183-228 of SEQ ID NO: 49, nucleotides 44-93 and 182-227 of SEQ ID NO: 50, nucleotides 43-92 and 181-226 of SEQ ID NO: 51, nucleotides 45-94 and 183-228 of SEQ ID NO: 52, nucleotides 46-92 and 161-194 of SEQ ID NO: 53, nucleotides 49-98 and 187-232 of SEQ ID NO: 54, nucleotides 45-94 and 183-228 of SEQ ID NO: 55, nucleotides 48-97 and 186-231 of SEQ ID NO: 56, nucleotides 47-96 and 185-230 of SEQ ID NO: 57, nucleotides 45-94 and 183-228 of SEQ ID NO: 58, nucleotides 47-96 and 185-230 of SEQ ID NO: 59, nucleotides 47-96 and 185-230 of SEQ ID NO: 60, nucleotides 49-98 and 187-232 of SEQ ID NO: 61, nucleotides 51-100 and 189-234 of SEQ ID NO: 62, nucleotides 47-96 and 185-230 of SEQ ID NO: 63, and nucleotides 51-97 and 195-244 of SEQ ID NO: 64 are shown.

DESCRIPTION

Provided here is triticale seed, a triticale plant, a triticale line and a triticale hybrid. This invention further relates to a method for producing triticale seed and plants. All references cited in this application are herein incorporated by reference.

Most of the triticale grown in the United States is used for feed grain and forage for swine, dairy cattle, and poultry. Triticale competes with other cereal grains, primarily common wheat and oats, for these forage markets. These markets in the U.S. are substantial. Cereal silage and hay are important in the major dairy producing regions, and cereal hay is a popular forage for horses.

Triticale is a cross between wheat as the female plant and rye as the pollinator. Compared to common wheat and oats, triticale has important advantages for forage production in terms of yield, production costs, and tolerance to pests, drought, low fertility, mineral toxicities, and heavy grazing. Triticale is generally superior to all classes of common wheat for pasture, silage, hay, and for grain used for feed. Triticales, like common wheat, have either a winter or spring growth habit, but vary significantly in plant height, tend to tiller less, and have a larger inflorescence when compared with common wheat. The majority of triticale cultivars have prominent awns, which sometimes cause problems in pastures or in hay. Certain releases are awnless and have increased its potential use as forage.

Common wheat and triticale have many similarities in their pattern of plant development and morphology. The flower heads or spikes, develop at the top of the main stems and secondary stems called tillers, which are analogous to branches. An individual plant usually has a main stem and multiple tillers, the number of which depends on plant density, soil moisture, nutrient supply, pest damage, seeding date, and temperature, as well as the genetics of the plant. Typically, two to four tillers per plant will develop to the point of developing a head. Each head at the top of the stem consists of multiple spikelets, each of which consists of multiple florets that produce pollen, ovules, and ultimately, kernels.

Triticale has many benefits to offer crop producers, livestock feeders, and for commercial use in soft-dough mixtures. Its major strength is its versatility: it can be used for grazing, silage, feed, cover crops, straw, and even human consumption. Additionally, production of triticale provides environmental benefits such as erosion control and improved nutrient cycling through crop rotation. Thus, because of its considerable benefits, significant plant breeding effort has been directed towards breeding triticale.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In triticale, the important traits include by way of example, increased yield and quality, resistance to diseases and insects, resistance to drought and heat, and improved agronomic traits.

Factors involved in the production of hybrid seed include controlled cross-pollination while limiting self-pollination, allowing sufficient pollen transfer, and retaining hybrid vigor and desirable characteristics in the progeny. Several methods have been proposed to limit self-pollination (selfing) of the parental lines. These methods include emasculation, chemically-induced male sterility, genetically-induced male sterility, cytoplasmic male sterility, day length incompatibility and self-incompatibility. For example, emasculation can be achieved manually or mechanically on tomato and maize, respectively. Emasculation is generally not applicable, however, to wheat and triticale due to flower architecture and scale(s) of production.

In one aspect of the methods, an A line triticale plant has cytoplasmic male sterility (CMS). It may be used in crosses with another male fertile line to produce hybrid progeny. B maintainer lines are provided which are male fertile plants of the line. In another aspect restorer (R) lines are provided. The maintainer and restorer lines are male fertile and female fertile. The CMS and maintainer lines are the same line other than the maintainer line is male fertile. The cytoplasmic component of the genome is not transferred through pollen and thus the progeny of a cross between the maintainer and CMS line is male sterile. Hybrid seeds are produced in a cross with a restorer line that is male fertile and restores fertility to progeny.

As detailed below, a comparison of the cytoplasm of 343CMS with the genome of 15 triticale lines showed distinct sequence changes in the known mitochondrial genes, Atp8-1, NAD9 and NAD4L. ATP synthase produces ATP from ADP. Atp8 refers to mitochondrially encoded ATP synthase membrane subunit 8 that encodes a subunit of mitochondrial ATP synthase. It is linked to CMS in *Brassica*, *Raphanus* and sunflower. See, e.g., Hanson et al. (2004) "Interactions of mitochondrial and nuclear genes that affect male gametophyte development" The Plant Cell Vol. 16 5154-5169. NAD9 is a subunit of mitochondrial NADH dehydrogenase. See Lamattina et al. (1993) "Higher plant mitochondria encode an homologue of the nuclear-encoded 30-kDa subunit of bovine mitochondrial complex" Eur. J. Biochem. 217, 831-838. NAD4L is a subunit of NADH dehydrogenase. It also has been associated with CMS. See Sinha et al. (2015) "Association of gene with cytoplasmic male sterility in Pigeonpea" The Plant Genome Vol. 8, No. 2.

The comparison showed that 343CMS had changes at positions 155, 176, 186, 286, 295, and 337bp of the Atp8-1 gene; changes in position 170 and 338 bp of NAD9 and in NAD4L changes in positions 51, 54, 57, 89, 99, 106, 159, 181, 185, 199, 220, 226, and 425 to 429 bp that differentiated it cytoplasm from other accessions. Markers for such sequence changes allows for detection of 343CMS.

Compositions disclosed herein include polynucleotides and polypeptides that influence male fertility. In particular, isolated polynucleotides are provided comprising nucleotide sequences set forth in SEQ ID NOs: 32, 48, 64, 66, and 68, or active fragments or variants thereof. Further provided are polypeptides having an amino acid sequence encoded by a polynucleotide described herein, for example those set forth in SEQ ID NO: 70 or 72, or active fragments or variants thereof.

Sexually reproducing plants develop specialized tissues for the production of male and female gametes. Successful production of male gametes relies on proper formation of the male reproductive tissues. The stamen, which embodies the male reproductive organ of plants, contains various cell types, including for example, the filament, anther, tapetum, and pollen. As used herein, "male tissue" refers to the specialized tissue in a sexually reproducing plant that is responsible for production of the male gamete. Male tissues include, but are not limited to, the stamen, filament, anther, tapetum, and pollen.

The process of mature pollen grain formation begins with microsporogenesis, wherein meiocytes are formed in the sporogenous tissue of the anther. Microgametogenesis follows, wherein microspore nuclei undergo an asymmetric mitotic division to develop the microgametophyte, or pollen grain. The condition of "male fertility" or "male fertile" refers to those plants producing a mature pollen grain capable of fertilizing a female gamete to produce a subsequent generation of offspring. The term "influences male fertility" or "modulates male fertility", as used herein, refers to any increase or decrease in the ability of a plant to produce a mature pollen grain when compared to an appropriate control. A "mature pollen grain" or "mature pollen" refers to any pollen grain capable of fertilizing a female gamete to produce a subsequent generation of offspring. Likewise, the term "male-fertility polynucleotide" or "male-fertility polypeptide" refers to a polynucleotide or polypeptide that modulates male fertility.

Male-fertility polynucleotides disclosed herein include homologs and orthologs of polynucleotides shown to influence male fertility. For example, male-fertility polynucleotides, and active fragments and variants thereof, disclosed herein include homologs and orthologs of Atp8-1, NAD9, and NAD4L.

Fragments and variants of the disclosed polynucleotides and proteins encoded thereby are also provided. By "fragment" is intended a portion of the polynucleotide or a portion of the amino acid sequence and hence protein encoded thereby. Fragments of a polynucleotide may encode protein fragments that retain the biological activity of the native protein and hence influence male fertility; these fragments may be referred to herein as "active fragments." Alternatively, fragments of a polynucleotide that are useful as hybridization probes or which are useful in constructs and strategies for down-regulation or targeted sequence modification generally do not encode protein fragments retaining biological activity, but may still influence male fertility. Thus, fragments of a nucleotide sequence may range from at least about 20 nucleotides, about 50 nucleotides, about 100 nucleotides, up to the full-length polynucleotide encoding a polypeptide disclosed herein.

A fragment of a polynucleotide that encodes a biologically active portion of a polypeptide that influences male fertility will encode at least 15, 25, 30, 50, 100, 150, or 200 contiguous amino acids, or up to the total number of amino acids present in a full-length polypeptide that influences male fertility. Fragments of a male-fertility polynucleotide that are useful as hybridization probes or PCR primers, or in a down-regulation construct or targeted-modification method generally need not encode a biologically active portion of a polypeptide but may influence male fertility.

Thus, a fragment of a male-fertility polynucleotide as disclosed herein may encode a biologically active portion of a male-fertility polypeptide, or it may be a fragment that can be used as a hybridization probe or PCR primer or in a downregulation construct or targeted-modification method using methods known in the art or disclosed below. A biologically active portion of a male-fertility polypeptide can be prepared by isolating a portion of one of the male-fertility polynucleotides disclosed herein, expressing the encoded portion of the male-fertility protein (e.g., by recombinant expression in vitro), and assessing the activity of the encoded portion of the male-fertility polypeptide. Polynucleotides that are fragments of a male-fertility polynucleotide comprise at least 16, 20, 50, 75, 100, 150, 200, 250, 300, 350, 400, 450, 500, 550, 600, 650, 700, 800, 900, 1000, 1200, 1400, 1600, 1800, 2000, 2200, 2400, 2600, 2800, 3000, 3200, 3400, 3600, 3800, or 4000 nucleotides, or up to the number of nucleotides present in a full-length male-fertility polynucleotide disclosed herein.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of a male-fertility polypeptide disclosed herein. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis, and which may encode a male-fertility polypeptide. Generally, variants of a particular polynucleotide disclosed herein will have at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to that particular polynucleotide as determined by sequence alignment programs and parameters described elsewhere herein or known in the art.

Variants of a particular polynucleotide disclosed herein (i.e., a reference polynucleotide) can also be evaluated by comparison of the percent sequence identity between the polypeptide encoded by a variant polynucleotide and the polypeptide encoded by the reference polynucleotide. Thus, for example, an isolated polynucleotide may encode a polypeptide with a given percent sequence identity to the polypeptide of SEQ ID NO: 70 or 72. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more sites in the native protein and/or substitution of one or more amino acids at one or more sites in the native protein. Variant proteins disclosed herein are biologically active, that is they continue to possess biological activity of the native protein, that is, male fertility activity as described herein. Such variants may result from, for example, genetic polymorphism or human manipulation. Biologically active variants of a male-fertility protein disclosed herein will have at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to the amino acid sequence for the native protein as determined by sequence alignment programs and parameters described elsewhere herein or known in the art. A biologically active variant of a protein disclosed herein may differ from that protein by as few as 1-15 amino acid residues, as few as 1-10, such as 6-10, as few as 5, as few as 4, 3, 2, or even 1 amino acid residue.

The proteins disclosed herein may be altered in various ways including amino acid substitutions, deletions, truncations, and insertions. Methods for such manipulations are generally known in the art. For example, amino acid sequence variants and fragments of the male-fertility polypeptides can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

Thus, the genes and polynucleotides disclosed herein include both the naturally occurring sequences as well as DNA sequence variants. Likewise, the male-fertility polypeptides and proteins encompass both naturally occurring polypeptides as well as variations and modified forms thereof. Such polynucleotide and polypeptide variants may continue to possess the desired male-fertility activity, in which case the mutations that will be made in the DNA encoding the variant must not place the sequence out of reading frame and optimally will not create complementary regions that could produce secondary mRNA structure. See, EP Patent Application Publication No. 75,444.

Certain deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for male fertility activity.

Increases or decreases in male fertility can be assayed in a variety of ways. One of ordinary skill in the art can readily assess activity of the variant or fragment by introducing the polynucleotide into a plant homozygous for a stable male-sterile allele of the polynucleotide, and observing male tissue development in the plant.

Variant functional polynucleotides and proteins also encompass sequences and proteins derived from a mutagenic and recombinogenic procedure such as DNA shuffling. With such a procedure, one or more different male fertility sequences can be manipulated to create a new male-fertility polypeptide possessing desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the male-fertility polynucleotides disclosed herein and other known male-fertility polynucleotides to obtain a new gene coding for a protein with an improved property of interest, such as an increased $K_m$ in the case of an enzyme. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

As used herein, "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

A person of skill in the art appreciates there are a variety of methods to produce markers that allow for identification of the distinguishing sequences changes. Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected eg via DNA sequencing, PCR-based sequence specific amplification methods, detection of polynucleotide polymorphisms by allele specific hybridization (ASH), dynamic allele-specific hybridization (DASH), Competitive (Kompetitive) Allele-Specific Polymerase chain reaction (KASPar), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology have the advantage of being able to detect a series of linked SNP alleles that constitute a haplotype. Haplotypes tend to be more informative (detect a higher level of polymorphism) than SNPs.

One such method is to use KASP system. The process uses an assay mix of three assay-specific oligonucleotides, including two alleles specific forward primers and one common reverse primer. The allele-specific primers have a unique tail sequence corresponding with a universal fluorescence resonant energy transfer cassette (FRET) where one is labeled with a dye (FAM™) and the other with a different dye (HEX™). A master mix has the universal FRET cassettes, a passive reference dye (ROX™) and TAQ polymerase. The allele-specific primer binds and elongates the template during thermal cycling which includes the tail in the produced strand. When the complement of the tail sequence is produced in subsequent PCR rounds the FRET cassette can bind to the DNA. Since the FRET cassette is no longer quenched it will fluoresce. A homozygous SNP presence will produce one of the fluorescent signals, if it is heterozygous, a mixed fluorescent signal is produced.

Producing primers and probes that amplify or detect the presence of a sequence can be readily accomplished by a person of skill in the art. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook, J., Fritsch, E. F. and Maniatis, T. (2001) Molecular Cloning: A Laboratory Manual, 3rd Edition. Cold Spring Harbor Laboratory Press, Plainview, N. Y; Innis, M., Gelfand, D. and Sninsky, J. (1995) PCR Strategies. Academic Press, New York; Innis, M., Gelfand, D. and Sninsky, J. (1999) PCR Applications: Protocols for Functional Genomics, Academic Press, New York. Indeed, computer programs can determine primers that hybridize with targeted sequences.

By way of further example, without limitation, hybridization probes may be genomic DNA fragments, cDNA fragments, RNA fragments, or other oligonucleotides, and may be labeled with a detectable group such as 32P, or any other detectable marker. Thus, for example, probes for hybridization can be made by labeling synthetic oligonucleotides based on the DNA sequences. Methods for preparation of probes for hybridization and for construction of cDNA and genomic libraries are generally known in the art and are disclosed (Sambrook et al., (2001) *Molecular Cloning: A Laboratory Manual* ($3^{rd}$ ed., Cold Spring Harbor Laboratory Press, Plainview, N.Y.). For example, the sequence disclosed herein, or one or more portions thereof, may be used as a probe capable of specifically hybridizing to corresponding sequences. To achieve specific hybridization under a variety of conditions, such probes include sequences that are unique among the sequences to be screened and can be at least about 10 nucleotides in length, and can be at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 2001).

It will be evident to one of skill in the art that the above sequences may be introduced into a plant not comprising the sequences, using techniques such as those described herein.

When producing a line or variety, choice of breeding or selection methods depends on the mode of plant reproduction, the heritability of the trait(s) being improved, and the type of cultivar used commercially (e.g., $F_1$ hybrid cultivar, pureline cultivar, etc.). Popular selection methods commonly include pedigree selection, modified pedigree selection, mass selection, and recurrent selection.

The goal of a commercial triticale breeding program is to develop new, unique and superior triticale cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new triticale cultivars.

Pureline cultivars of triticale are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self-pollinated crops such as triticale. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an F (filial generation 1). An $F_2$ population is produced by selfing $F_1$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

One method of breeding utilizes the single seed descent procedure which the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using off-season nurseries.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs). Such techniques are described further supra.

Molecular markers, which include markers identified through the use of techniques such as Starch Gel Electrophoresis, Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation breeding is another method of introducing new traits into triticale varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Allard, 1960; Simmonds, 1979; Sneep, et al. 1979; Fehr, 1987).

Triticale is an important and valuable field crop. Thus, a continuing goal of triticale plant breeders is to develop stable, high yielding triticale cultivars that are agronomically sound. The reasons for this goal are to maximize yield and the quality of the final product for forage, silage, and human consumption. To accomplish this goal, the triticale breeder must select and develop plants that have the traits that result in superior cultivars. The development of new triticale cultivars requires the evaluation and selection of parents and the crossing of these parents. The lack of predictable success of a given cross requires that a breeder, in any given year, make several crosses with the same or different breeding objectives.

The foregoing examples of the related art and limitations related therewith are intended to be illustrative and not exclusive. Other limitations of the related art will become apparent to those of skill in the art upon a reading of the specification. References cited herein are incorporated herein by reference.

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Awn. Awn is intended to mean the elongated needle-like appendages on the flower and seed-bearing "head" at the top of the cereal grain plant (e.g., triticale, common wheat, rye). These awns are attached to the lemmas. Lemmas enclose the stamen and the stigma as part of the florets. These florets are grouped in spikelets, which in turn together comprise the head.

Backcrossing. Backcrossing is a process in which a breeder repeatedly crosses hybrid progeny back to one of the parents, for example, a first generation hybrid $F_1$ with one of the parental genotypes of the $F_1$ hybrid.

Disease Resistance. As used herein, the term "disease resistance" is defined as the ability of plants to restrict the activities of a specified pest or pathogen, such as an insect, fungus, virus, or bacterial.

Disease Tolerance. As used herein, the term "disease tolerance" is defined as the ability of plants to endure a specified pest or pathogen (such as an insect, fungus, virus or bacteria) or an adverse environmental condition and still perform and produce in spite of this disorder.

Essentially all of the physiological and morphological characteristics. A plant having essentially all of the physiological and morphological characteristics means a plant having the physiological and morphological characteristics of the recurrent parent, except for the characteristics derived from the converted trait.

Head. As used herein, the term "head" refers to a group of spikelets at the top of one plant stem. The term "spike" also refers to the head of a plant located at the top of one plant stem.

Maturity. As used herein, the term "maturity" refers to the stage of plant growth at which the development of the kernels is complete.

As used herein, the term plant includes reference to an immature or mature whole plant, including a plant from which seed, grain, or anthers have been removed. A seed or embryo that will produce the plant is also considered to be a plant. Reference to a plant is used broadly herein to include any plant at any stage of development.

A plant part refers to any part of a plant, including a plant cutting, a plant cell, a plant cell culture, a plant organ, a plant seed, and a plantlet. Examples include, without limitation, protoplasts, callus, leaves, stems, roots, root tips, anthers, pistils, seed, grain, pericarp, embryo, pollen, ovules, cotyledon, hypocotyl, spike, floret, awn, lemma, shoot, tissue, petiole, cells, and meristematic cells. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. A plant part includes plant tissue or any other groups of plant cells that is organized into a structural or functional unit.

Plant Height (Hgt). As used herein, the term "plant height" is defined as the average height in inches or centimeters of a group of plants.

Stripe Rust. A disease of triticale, common wheat, durum wheat, and barley characterized by elongated rows of yellow spores on the affected parts, caused by a rust fungus, *Puccinia striiformis*.

Single Trait Converted (Conversion). Single trait converted (conversion) plant refers to plants which are developed by a plant breeding technique called backcrossing or via genetic engineering wherein essentially all of the desired morphological and physiological characteristics of a variety are recovered in addition to the single trait transferred into the variety via the backcrossing technique or via genetic engineering.

343CMS

343CMS is a cytoplasmic male sterile (CMS) facultative, awned, semidwarf hexaploidy triticale. The variety is CMS stable and sterile. 343CMS (and its maintainer line 3-4-4) is a medium tall triticale ranging in plant height from 32-42" depending upon the environment. It is a facultative triticale with good enough winterhardiness to survive Kansas winter conditions but capable of being planted as a spring type. It is medium early in maturity. 343CMS is awned. At maturity it has black awns and purple seed. It is resistant to local races of stripe rust in Kansas but susceptible to local races of leaf rust. 343CMS (and its maintainer line 3-4-4) has been stable since 2012. Less than 0.1% of the plants were rogued from the Breeder seed increase in 2017. Approximately 80% of the variant plants were taller height plants and approximately 20% were awnletted plants. Up to 1.0% variant plants may be encountered in subsequent generations.

343CSM has been selected for uniform and stable sterility, significantly improved outcrossing ability and flexibility to be planted both in the winter and spring environments. It is a medium plant height, medium early triticale that has resistance to stripe rust but is susceptible to leaf rust.

The variety is uniform, has stable sterility and significantly improved outcrossing ability and flexibility. It has been tested for uniformity and stability for five years growth. Up to 1% variant plants can be observed or expected during reproduction and multiplication. Expression of both black awns and purple seed is affected by cooler night time temperatures during grain filling. Cooler temperatures at night increase the expression of both traits. 343CMS is maintained by a fertile maintainer line (3-4-4) which contains a normal Durum cytoplasm and is self-fertile. Both 343CMS and 3-4-4 are identical in phenotype and have been stable and uniform for 5 years.

343CMS can be produced using 3-4-4 as a male donator of pollen. Ratios used to produce the CMS sterile 343CMS will generally be three parts 343CMS and one part fertile and pollen producing 3-4-4 planted in a strip planting design. 3-4-4 is derived from the cross BX 10356 which was the combination of 3 experimental selections. 343CMS has been back-crossed (maintained) by 3-4-4 for 8 generations (BC8).

The following is a botanical description of the new variety of triticale based on observations of various specimens grown in Junction City, Kans., Yuma, Ariz., Bozeman, Mont., and Moses Lake, Wash.

TABLE 1

| Growth Habit | |
| --- | --- |
| Spring/intermediate/winter | Spring/intermediate/winter |
| Juvenile plant growth | Semi-prostrate |
| Photoperiod | Insensitive |
| Use | Dual grain, feed and forage |
| Ploidy | Hexaploid, 42 2n chromosome number |
| Maturity | Early, same as PVP 946802617 |
| Height | Mid-tall, same as PVP 946802617 |
| Plant color at boot stage | Green |
| Stem | |
| Anthocyanin | Absent |
| Neck hairiness | Moderate |
| Shape of neck | Straight |
| Leaves | |
| Flag leaf | Not twisted |
| Waxy bloom on leaf at boot | Absent |
| Leaf carriage | Recurved |
| Leaf length | 28 cm (1$^{st}$ leaf below flag leaf) |
| leaf width | 1.5 mm (1$^{st}$ leaf below flag leaf) |
| Auricle color | Purple |
| Head | |
| Density | Mid-dense |
| Shape | Oblong |
| Awnedness | Awned |
| Awn color | Tan |
| Head length | 10 cm |
| Head width | 15 mm |
| Glumes at maturity | |
| Pubescence | Slightly pubescent |
| Color | Tan |
| Length | Mid-long |
| Width | Mid-wide |
| Shoulder | Oblique |
| Apiculate | Obtuse |
| Coleoptile color | Purple |
| Seed | |
| Shape | Oval |
| Smoothness | Slightly wrinkled |
| Brush area | Large |
| Brush length | Long |
| Color | Purple |
| GMS per 1,000 seed | 35 |
| Disease | |
| Stripe Rust | Resistant to Kansas races |
| Powdery mildew | Resistant |
| Septoria | Susceptible |
| Leaf rust | Susceptible |
| Ergot | Susceptible |
| Bacterial stripe | Susceptible |

343CMS is most similar to variety PVP 946802617, in plant tillering, winter hardiness, area of adaptation and seed shape. In qualitative traits, winter hardiness was tested in Kansas. 343CMS survived the winters in Kansas. Seed of 343CMS was purple in color, where seed of PVP 946802617 was tan.

This invention is also directed to methods for producing a triticale plant by crossing a first parent triticale plant with a second parent triticale plant, wherein the first or second triticale plant is the triticale plant from the cultivar 343CMS. Further, the first or second parent may be a common wheat cultivar. Therefore, any methods using the cultivar 343CMS are part of this invention: backcrosses, hybrid breeding, and crosses to populations. Any plants produced using cultivar 343CMS as a parent are within the scope of this invention. As used herein, the term "plant" includes plant cells, plant protoplasts, plant cells of tissue culture from which triticale plants can be regenerated, plant calli, plant clumps, and plant cells that are intact in plants or parts of plants, such as pollen, flowers, embryos, ovules, seeds, leaves, stems, roots, anthers and the like. Thus, another aspect of this invention is to provide for cells which upon growth and differentiation produce a cultivar having essentially all of the physiological and morphological characteristics of 343CMS.

The present compositions and methods contemplate a triticale plant regenerated from a tissue culture of a cultivar (e.g., 343CMS) or hybrid plant of the present invention. As is well known in the art, tissue culture of triticale can be used for the in vitro regeneration of a triticale plant. Tissue culture of various tissues of plants and regeneration of plants therefrom is well known and widely published.

Further Embodiments and Methods

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Many methods for producing transgenic plants have been developed, and the present invention, in particular embodiments, also relates to transformed versions of the claimed cultivar.

When referring to a transgene is meant to include a heterologous nucleic acid molecule which may be a heterologous polynucleotide or a heterologous nucleic acid or an exogenous DNA and includes a polynucleotide, nucleic acid or DNA segment that originates from a source foreign to the particular host cell, or, if from the same source, is modified from its original form in composition and/or genomic locus by human intervention. When referring to a gene or transgene that may be introduced into the plant is intended to include portions of the gene, and it may not include the entire gene, and may not include the native promoter or other components. By way of example without limitation, it can include sequences that are duplicates of those already in the plant cell, may be a modified version of the sequence, or its expression or function modified. A heterologous gene in a host cell includes a gene that is endogenous to the particular host cell, but has been modified or introduced into the plant. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides. As noted, a heterologous nucleic acid molecule may be introduced into the plant by any convenient methods. In one embodiment the heterologous nucleic acid molecule may be a transgene that is introduced by transformation.

The term introduced in the context of inserting a nucleic acid or polypeptide into a cell, includes transfection or transformation or transduction and includes reference to the incorporation of a nucleic acid into a cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleic acid sequence into a plant is meant to include transformation into the cell, as well as crossing a plant having the sequence with another plant, so that the second plant contains the heterologous sequence or transgene, as in conventional plant breeding techniques. Such breeding techniques are well known to one skilled in the art and examples are discussed herein. For a discussion of plant breeding techniques, see Poehlman (1995) *Breeding Field Crops*. AVI Publication Co., Westport Conn., 4th Edit. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent. Examples of such techniques and variations are set forth in further detail herein.

Various genetic elements can be introduced into the plant genome using transformation. These elements include, but are not limited to genes, coding sequences, inducible, constitutive, and tissue-specific promoters, enhancing sequences, and signal and targeting sequences.

In some embodiments, the invention comprises a CMS343 plant that has been developed using both genetic engineering and traditional breeding techniques. For example, a genetic trait may have been engineered into the genome of a particular wheat plant may then be moved into the genome of a CMS343 plant using traditional breeding techniques that are well known in the plant breeding arts. Likewise, a genetic trait that has been engineered into the genome of a CMS343 wheat plant may then be moved into the genome of another cultivar using traditional breeding techniques that are well known in the plant breeding arts. A backcrossing approach is commonly used to move a transgene or transgenes from a transformed wheat cultivar into an already developed wheat cultivar, and the resulting backcross conversion plant would then comprise the transgene(s).

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed triticale plants, using transformation methods as described below to incorporate transgenes into the genetic material of the triticale plant(s).

Expression Cassettes

A male-fertility polynucleotide disclosed herein can be provided in an expression cassette for expression in an organism of interest. The cassette can include 5' and 3' regulatory sequences operably linked to a male-fertility polynucleotide as disclosed herein. "Operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

The expression cassettes disclosed herein may include in the 5'-3' direction of transcription, a transcriptional and translational initiation region (i.e., a promoter), a polynucleotide of interest, and a transcriptional and translational termination region (i.e., termination region) functional in the host cell (e.g., a plant cell). Expression cassettes are also provided with a plurality of restriction sites and/or recombination sites for insertion of the male-fertility polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, "heterologous" in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, unless otherwise specified, a chimeric polynucleotide comprises a coding sequence operably linked to a transcription initiation region that is heterologous to the coding sequence.

In certain embodiments the polynucleotides disclosed herein can be stacked with any combination of polynucleotide sequences of interest or expression cassettes as disclosed elsewhere herein or known in the art. For example, the male-fertility polynucleotides disclosed herein may be stacked with any other polynucleotides encoding male-gamete-disruptive polynucleotides or polypeptides, cytotoxins, markers, or other male fertility sequences as disclosed elsewhere herein or known in the art. The stacked polynucleotides may be operably linked to the same promoter as the male-fertility polynucleotide, or may be operably linked to a separate promoter polynucleotide.

As described elsewhere herein, expression cassettes may comprise a promoter operably linked to a polynucleotide of interest, along with a corresponding termination region. The termination region may be native to the transcriptional initiation region, may be native to the operably linked male-fertility polynucleotide of interest or to the male-fertility promoter sequences, may be native to the plant host, or may be derived from another source (i.e., foreign or heterologous). Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acids Res. 15:9627-9639.

Where appropriate, the polynucleotides of interest may be optimized for increased expression in the transformed plant. That is, the polynucleotides can be synthesized or altered to use plant-preferred codons for improved expression. See, for example, Campbell and Gown (1990) Plant Physiol. 92:1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Johnson et al. (1986) Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In particular embodiments, the expression cassettes disclosed herein comprise a promoter operably linked to a male-fertility polynucleotide, or fragment or variant thereof, as disclosed herein. In certain embodiments, a male-fertility promoter is operably linked to a male-fertility polynucleotide disclosed herein, such as the male-fertility polynucleotide set forth in SEQ ID NO: NOs: 32, 48, 64, 66, or 68, or an active fragment or variant thereof.

Expression Vectors for Triticale Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., Plant Physiol. 86:1216 (1988), Jones et al., Mol. Gen. Genet, 210:86 (1987), Svab et al., Plant Mol. Biol. 14:197 (1990) Hille et al., Plant Mol. Biol. 7:171 (1986). Other selectable marker genes confer resistance to herbicides such as glyphosate, glufosinate or bromoxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation that are not of bacterial origin include, for example, mouse dihydrofolate reductase, plant 5-enolpyruvyl-shikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include .beta.-glucuronidase (GUS), .beta.-galactosidase, luciferase and chloramphenicol acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984).

In vivo methods for visualizing GUS activity that do not require destruction of plant tissue are available. Molecular Probes publication 2908, Imagene Green, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

The gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Expression Vectors for Triticale Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A constitutive promoter is operably linked to a gene for expression in wheat, or is operably linked to a nucleotide sequence encoding a signal sequence that is operably linked to a gene for expression in triticale. Many different constitutive promoters are available. Exemplary constitutive promoters include, but are not limited to, the promoters from plant viruses, such as the 35S promoter from CaMV and the promoters from such genes as rice actin; ubiquitin; pEMU; MAS, and maize H3 histone. The ALS promoter, Xbal/Ncol fragment 5' to the *Brassica napus* ALS3 structural gene (or a nucleotide sequence similarity to said Xbal/Ncol fragment), represents a particularly useful constitutive promoter.

A tissue-specific promoter or tissue-preferred promoter may be operably linked to a gene for expression in triticale. Plants transformed with a gene of interest operably linked to a tissue-specific promoter may produce the protein product of the transgene exclusively, or preferentially, in a specific tissue. Any tissue-specific or tissue-preferred promoter can be utilized in the present invention. Exemplary tissue-specific or tissue-preferred promoters include, but are not limited to, a root-preferred promoter, such as that from the phaseolin gene; a leaf-specific and light-induced promoter, such as that from cab or rubisco; an anther-specific promoter, such as that from LAT52; a pollen-specific promoter, such as that from Zml 3; or a microspore-preferred promoter, such as that from apg.

An inducible regulatory element is one that is capable of directly or indirectly activating transcription of one or more DNA sequences or genes in response to an inducer. In the absence of an inducer the DNA sequences or genes will not be transcribed. Any inducible promoter may be used in the present invention. Exemplary inducible promoters include, but are not limited to, those from the ACEI system, which respond to copper, and the In2 gene from maize, which responds to benzene-sulfonamide herbicide safeners. In an embodiment, the inducible promoter may be a promoter that responds to an inducing agent to which plants do not normally respond. An exemplary inducible promoter may be an inducible promoter from a steroid hormone gene, the transcriptional activity of which is induced by a glucocorticosteroid hormone.

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Fontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Heterologous Protein Genes and Agronomic Genes

With transgenic plants, a heterologous protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981). According to an embodiment, the transgenic plant provided for commercial production of foreign protein is a triticale plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269: 284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* RSP2 gene for resistance to *Pseudomonas syringae*).

B. A gene conferring resistance to a pest, such as nematodes. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding .delta.-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., Plant Molec. Biol. 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

L. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., Plant Sci 89:43 (1993), of heterologous expression of a cecropin-.beta. lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Taviadoraki et al., Nature 366:469 (1993), who show that transgenic plants expressing recombinant antibody genes are protected from virus attack.

R. A developmental-arrestive protein produced in nature by a pathogen or a parasite. Thus, fungal endo-.alpha.-1,4-D-polygalacturonases facilitate fungal colonization and plant nutrient release by solubilizing plant cell wall homo-.alpha.-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy proprionic acids and cyclohexens (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989), describe the production of transgenic plants that express chimeric bar genes coding for PAT activity. Exemplary of genes conferring resistance to phenoxy proprionic acids and cyclohexens, such as sethoxydim and haloxyfop are the Acc1-S1, Acc1-S2 and Acc1-S3 genes described by Marshall et al., Theor. Appl. Genet. 83:435 (1992).

C. An herbicide that inhibits photosynthesis, such as a triazine (psbA and gs+ genes) or a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Nat. Acad. Sci. U.S.A. 89:2624 (1992).

B. Decreased phytate content—1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis* .alpha.-amylase), Elliot et al., Plant Molec. Biol. 21:515 (1993) (nucleotide sequences of tomato invertase genes), SOgaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

E. The content of high-molecular weight gluten subunits (HMS-GS). Genomic clones have been isolated for different subunits (Anderson et al., In Proceedings of the 7.sup.th International Wheat Genetics Symposium, IPR, pp. 699-704, 1988; Shewry et al. In Oxford Surveys of Plant Molecular and Cell Biology, pp. 163-219, 1989; Shewry et al. Journal of Cereal Sci. 15:105-120, 1992). Blechl et al. (Journal of Plant Phys. 152 (6): 703-707, 1998) have transformed wheat with genes that encode a modified HMW-GS. See also U.S. Pat. Nos. 5,650,558; 5,914,450; 5,985,352; 6,174,725; and 6,252,134, which are incorporated herein by reference for this purpose.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Triticale Transformation

The methods disclosed herein comprise introducing a polypeptide or polynucleotide into a plant cell. "Introducing" is intended to mean presenting to the plant the polynucleotide or polypeptide in such a manner that the sequence gains access to the interior of a cell. The methods disclosed herein do not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods.

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide or polypeptide is introduced into the host (i.e., a plant) and expressed temporally.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J, 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-omithine has also been reported. Hain et al., Mol. Gen. Genet. 199:161 (1985) and Draper et al., Plant Cell Physiol. 23:451 (1982). Electroporation of protoplasts and whole cells and tissues has also been described. Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of triticale target tissues, expression of the above-described selectable marker genes allows for preferential selection of transformed cells, tissues and/or plants, using regeneration and selection methods now well known in the art.

In specific embodiments, the male-fertility polynucleotides or expression cassettes disclosed herein can be provided to a plant using a variety of transient transformation methods. Such transient transformation methods include, but are not limited to, the introduction of the male-fertility polypeptide or variants and fragments thereof directly into the plant or the introduction of a male fertility transcript into the plant. Such methods include, for example, microinjection or particle bombardment. See, for example, Crossway et al. (1986) Mol Gen. Genet. 202:179-185; Nomura et al. (1986) Plant Sci. 44:53-58; Hepler et al. (1994) Proc. Natl. Acad. Sci. 91: 2176-2180 and Hush et al. (1994) The Journal of Cell Science 107:775-784, all of which are herein incorporated by reference. Alternatively, the male-fertility polynucleotide or expression cassettes disclosed herein can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the male-fertility polynucleotides or expression cassettes disclosed herein may be introduced into plants by contacting plants with a virus or viral nucleic acids. Generally, such methods involve incorporating a nucleotide construct disclosed herein within a viral DNA or RNA molecule. It is recognized that a male fertility sequence disclosed herein may be initially synthesized as part of a viral polyprotein, which later may be processed by proteolysis in vivo or in vitro to produce the desired recombinant protein. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) Molecular Biotechnology 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, a polynucleotide disclosed herein can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) Plant Cell Reports 5:81-84. These plants may then be pollinated with either the same transformed strain or a different strain, and the resulting progeny having desired expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a male-fertility polynucleotide disclosed herein, for example, an expression cassette disclosed herein, stably incorporated into their genome.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular triticale cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Genome Editing

The terms "target site", "target sequence", "target DNA", "target locus", "genomic target site", "genomic target sequence", and "genomic target locus" are used interchangeably herein and refer to a polynucleotide sequence in the genome (including chloroplast and mitochondrial DNA) of a cell at which a double-strand break is induced in the cell genome. The target site can be an endogenous site in the genome of a cell or organism, or alternatively, the target site can be heterologous to the cell or organism and thereby not be naturally occurring in the genome, or the target site can be found in a heterologous genomic location compared to where it occurs in nature. As used herein, terms "endogenous target sequence" and "native target sequence" are used interchangeably herein to refer to a target sequence that is endogenous or native to the genome of a cell or organism and is at the endogenous or native position of that target sequence in the genome of a cell or organism. Cells include plant cells as well as plants and seeds produced by the methods described herein.

In one embodiments, the target site, in association with the particular gene editing system that is being used, can be similar to a DNA recognition site or target site that is specifically recognized and/or bound by a double-strand-break-inducing agent, such as but not limited to a Zinc Finger endonuclease, a meganuclease, a TALEN endonuclease, a CRISPR-Cas guideRNA or other polynucleotide guided double strand break reagent.

The terms "artificial target site" and "artificial target sequence" are used interchangeably herein and refer to a target sequence that has been introduced into the genome of a cell or organism. Such an artificial target sequence can be identical in sequence to an endogenous or native target sequence in the genome of a cell but be located in a different position (i.e., a non-endogenous or non-native position) in the genome of a cell or organism.

The terms "altered target site", "altered target sequence", "modified target site", and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Certain embodiments comprise polynucleotides disclosed herein which are modified using endonucleases. Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Endonucleases also include meganucleases, also known as homing endonucleases (HEases). Like restriction endonucleases, HEases bind and cut at a specific recognition site. However, the recognition sites for meganucleases are typically longer, about 18 bp or more. (See patent publication WO2012/129373 filed on Mar. 22, 2012). Meganucleases have been classified into four families based on conserved sequence motifs (Belfort M, and Perlman P S J. Biol. Chem. 1995; 270:30237-30240). These motifs participate in the coordination of metal ions and hydrolysis of phosphodiester bonds. HEases are notable for their long recognition sites, and for tolerating some sequence polymorphisms in their DNA substrates.

The naming convention for meganucleases is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr. Op. Biotechnol. 5:521-7; and Sadowski (1993) FASEB 7:760-7. In some examples the recombinase is from the Integrase or Resolvase families.

TAL effector nucleases are a class of sequence-specific nucleases that can be used to make double-strand breaks at specific target sequences in the genome of a plant or other organism. (Miller et al. (2011) Nature Biotechnology 29:143-148). Zinc finger nucleases (ZFNs) are engineered double-strand-break-inducing agents comprised of a zinc finger DNA binding domain and a double-strand-break-inducing agent domain. Recognition site specificity is conferred by the zinc finger domain, which typically comprises two, three, or four zinc fingers, for example having a C2H2 structure; however other zinc finger structures are known and have been engineered. Zinc finger domains are amenable for designing polypeptides which specifically bind a selected polynucleotide recognition sequence. ZFNs include engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognizes a sequence of 9 contiguous nucleotides;

with a dimerization requirement of the nuclease, two sets of zinc finger triplets are used to bind an 18-nucleotide recognition sequence.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene relates to a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. Provisional Application No. 62/023,239, filed Jul. 11, 2014). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence.

The Cas endonuclease gene can be Cas9 endonuclease, or a functional fragment thereof, such as but not limited to, Cas9 genes listed in SEQ ID NOs: 462, 474, 489, 494, 499, 505, and 518 of WO2007/025097 published Mar. 1, 2007. The Cas endonuclease gene can be a plant, maize or soybean optimized Cas9 endonuclease, such as but not limited to a plant codon optimized *Streptococcus pyogenes* Cas9 gene that can recognize any genomic sequence of the form N(12-30)NGG. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. Provisional Application No. 62/023,239, filed Jul. 11, 2014). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In certain embodiments the nucleotide sequence to be modified can be a regulatory sequence such as a promoter, wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers; see e.g. U.S. Pat. No. 5,837,850 issued Nov. 17, 1998), a mutation of DNA binding elements and/or deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or SulphonylUrea (Su) repressor/operator/inducer elements. The dehydration-responsive element (DRE) was first identified as a cis-acting promoter element in the promoter of the drought-responsive gene rd29A, which contains a 9 bp conserved core sequence, TACCGACAT (Yamaguchi-Shinozaki, K., and Shinozaki, K. (1994) Plant Cell 6, 251-264). Insertion of DRE into an endogenous promoter may confer a drought inducible expression of the downstream gene. Another example is ABA-responsive elements (ABREs) which contain a (C/T)ACGTGGC consensus sequence found to be present in numerous ABA and/or stress-regulated genes (Busk P. K., Pages M. (1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

Single-Gene Conversion

When the term "triticale plant" is used in the context of the present invention, this also includes any single gene conversions of that variety. The term "single gene converted plant" as used herein refers to those triticale plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental triticale plant which contributes the gene for the desired characteristic is termed the "nonrecurrent" or "donor parent". This terminology refers to the fact that the nonrecurrent parent is used one time in the backcross protocol and therefore does not recur. The parental triticale plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a triticale plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is made for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

Further reproduction of the variety can occur by tissue culture and regeneration. Tissue culture of various tissues of triticale and regeneration of plants therefrom is well known and widely published. For example, reference may be had to Komatsuda, T. et al., Crop Sci. 31:333-337 (1991); Stephens, P. A., et al., Theor. Appl. Genet 82:633-635 (1991); Komatsuda, T. et al., Plant Cell, Tissue and Organ Culture, 28:103-113 (1992); Dhir, S. et al. Plant Cell Reports 11:285-289 (1992); Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce triticale plants having the physiological and morphological characteristics of triticale cultivar 343CMS.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikes, seeds, leaves, stems, roots, root tips, anthers, awns, stems, and the like. Means for preparing and maintaining plant tissue culture are well known in the art. By way of example, a tissue culture comprising organs has been used to produce regenerated plants. U.S. Pat. Nos. 5,959, 185, 5,973,234 and 5,977,445, describe certain techniques.

Also provided are methods for producing a triticale plant by crossing a first parent triticale plant with a second parent triticale plant wherein the first or second parent triticale plant is a triticale plant of the cultivar 343CMS. Thus, any such methods using the triticale cultivar 343CMS are part of this invention: backcrosses, hybrid production, crosses to populations, and the like. All plants produced using triticale cultivar 343CMS as a parent are within the scope of this invention, including those developed from varieties derived from triticale cultivar 343CMS. Advantageously, the triticale cultivar could be used in crosses with other, different, triticale plants to produce first generation ($F_1$) triticale hybrid seeds and plants with superior characteristics. The cultivar of the invention can also be used for transformation where exogenous genes are introduced and expressed by the cultivar of the invention. Genetic variants created either through traditional breeding methods using cultivar 343CMS or through transformation of 343CMS by any of a number of protocols known to those of skill in the art are intended to be within the scope of this invention.

The following describes breeding methods that may be used with cultivar 343CMS in the development of further triticale plants. One such embodiment is a method for developing an 343CMS progeny triticale plant in a triticale plant breeding program comprising: obtaining the triticale plant, or a part thereof, of cultivar 343CMS utilizing said plant or plant part as a source of breeding material and selecting an 343CMS progeny plant with molecular markers in common with 343CMS and/or with morphological and/or physiological characteristics selected from those described above. Breeding steps that may be used in the triticale plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar 343CMS progeny triticale plants, comprising crossing cultivar 343CMS with another triticale plant, thereby producing a population of triticale plants, which, on average, derive 50% of their alleles from cultivar 343CMS. A plant of this population may be selected and repeatedly selfed or sibbed with a triticale cultivar resulting from these successive filial generations. One embodiment of this invention is the triticale cultivar produced by this method and that has obtained at least 50% of its alleles from cultivar 343CMS.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes triticale cultivar 343CMS progeny triticale plants comprising a combination of at least two 343CMS traits selected from the group consisting of those listed here so that said progeny triticale plant is not significantly different for said traits than triticale cultivar 343CMS as determined at the 5% significance level when grown in the same environment. Using techniques described herein, molecular markers may be used to identify said progeny plant as a 343CMS progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar 343CMS may also be characterized through their filial relationship with triticale cultivar 343CMS, as for example, being within a certain number of breeding crosses of triticale cultivar 343CMS. A breeding cross is a cross made to introduce new genetics into the progeny, and is distinguished from a cross, such as a self or a sib cross, made to select among existing genetic alleles. The lower the number of breeding crosses in the pedigree, the closer the relationship between triticale cultivar 343CMS and its progeny. For example, progeny produced by the methods described herein may be within 1, 2, 3, 4 or 5 breeding crosses of triticale cultivar 343CMS.

Further, testing was completed showing changes in the genes Atp8-1, NAD9 and NAD4L that differentiate the cytoplasm as outlined below. The following is presented by way of exemplification and is not intended to limit the scope of the invention.

Example 1

Methodology: Mitochondrial genome and mitochondrial specific genes (Coxa, Atp8-1, NAD9, and NAD4L) of the triticale line of the disclosure and other 15 lines with known cytoplasm were used in the study (details regarding the lines is provided in Table 1). Multiple sequence alignment of nucleotide sequences was performed using sequence alignment tool of CLC sequence viewer software with default settings (gap open cost=10 and gap extension cost=1).

Figure 2:
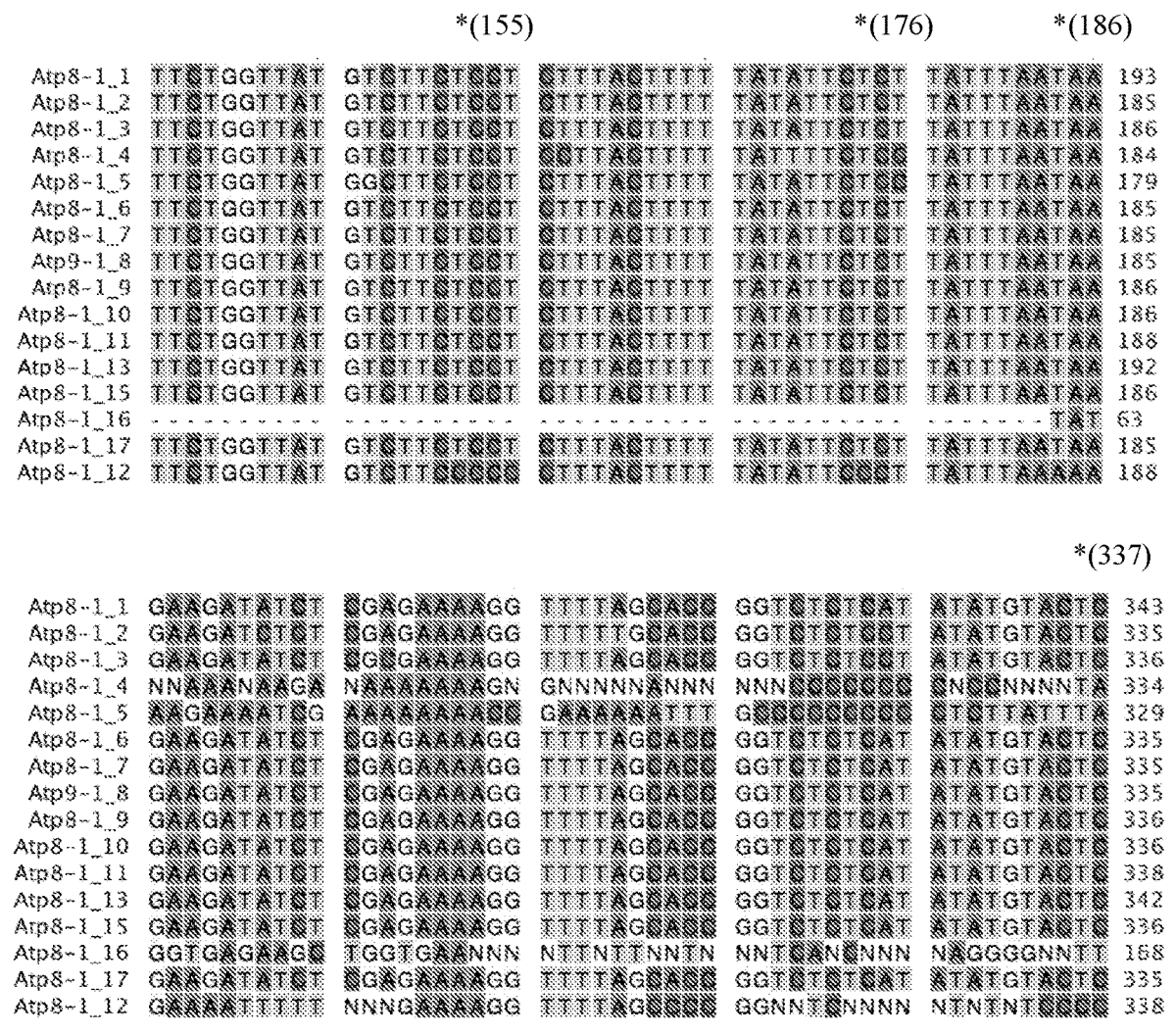

Results: Cytoplasmic diversity of Triticale line 343CMS with unknown cytoplasm from cytoplasm of known cytoplasmic male sterile lines/sources (Table 2) was studied by mitochondrial genome of all those lines that carry mitochondrial specific genes. Multiple sequence alignment of four known mitochondrial genes (Cox3, Atp8-1, NAD9, NAD4L) from the mitochondrial genome revealed that there is specific sequence change at nucleotide level that differentiates cytoplasm of two lines from the cytoplasm of known sources of male sterility. See FIGS. 1-4 where each of the compared sequences in the figures are numbered 1-11 and 13-17 and correspond to Table 2. Based on sequence comparison of Cox3 gene, cytoplasm of line 343CMS didn't carry any distinct sequence change that differentiated it's Cox3 gene from other accessions under study (FIG. 1). Similar comparison for gene Atp8-1, revealed that line 3-4-3 carried sequence change at positions 155, 176, 186, 286, 295, and 337 bp that differentiated its cytoplasm from other accessions under study. (FIG. 2). Sequence comparison of gene NAD9 revealed that cytoplasmic gene NAD9 of lines 3-4-3 is distinct from all the known sources of cytoplasm sterility due to sequence change at position 170 and 338 bp. Further sequence comparison based on gene NAD4L for all the accessions under study revealed that line 343CMS was carried sequence change at position 51, 54, 57, 89, 99, 106, 159, 181, 185, 199, 220, 226, and 425 to 429 bp.

Conclusion: Sequence comparison at nucleotide level between known male cytoplasmic sterile lines and Triticale line 343CMS suggests that cytoplasm of the line is distinct from known male sterile lines. The line can be differentiated from cytoplasm of other known sources of male sterility using sequence diversity present in the gene NAD9, that is unique to only these two lines. Further, uniqueness of the line's cytoplasm from all the accessions under study is revealed by presence of sequence change specific to this accession in gene Atp8-1 and NAD4L.

Marker development: KASP markers can be developed around these sequence changes for detection of cytoplasm of line 343CMS.

Figure 3:
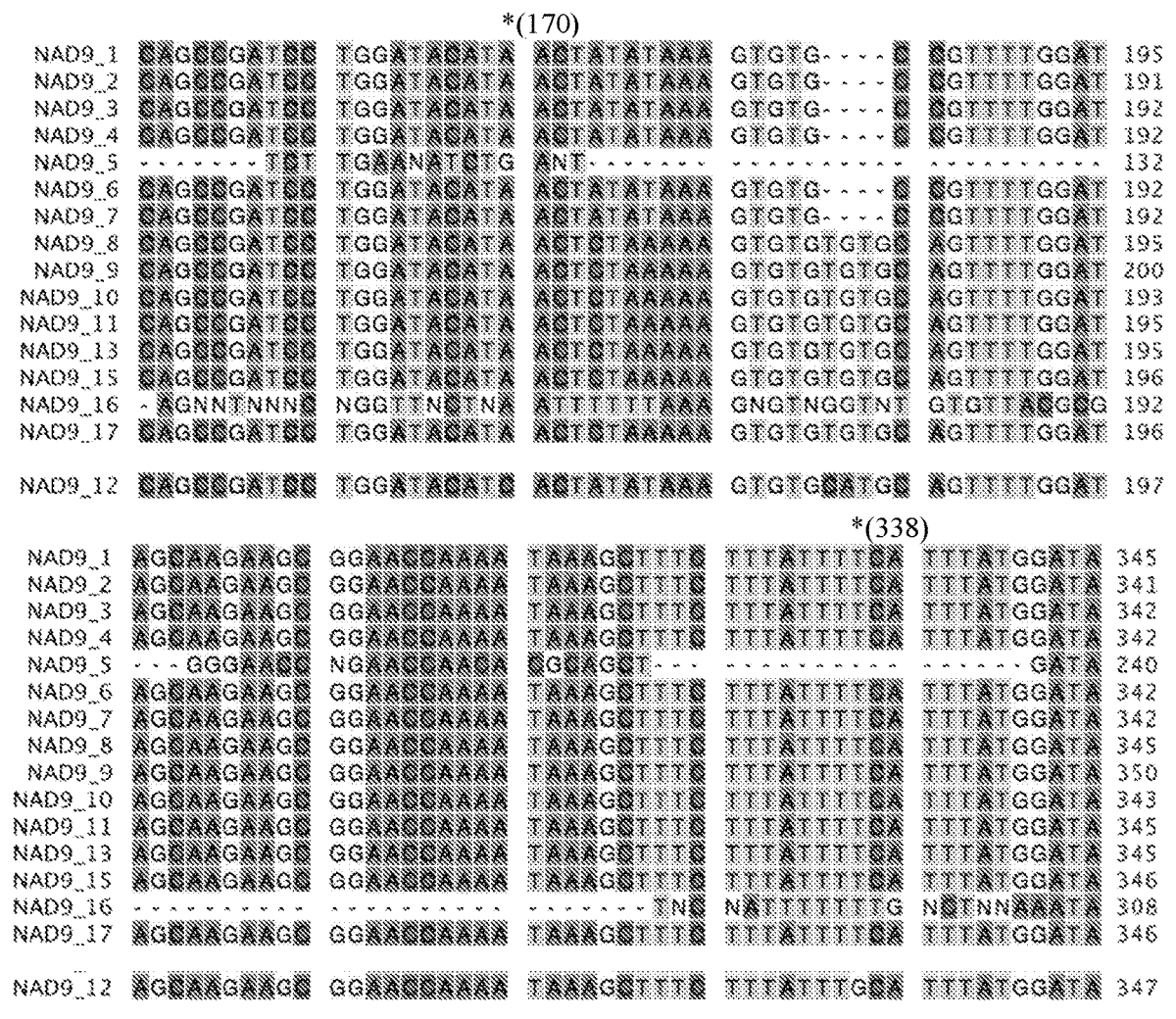
Figure 4:
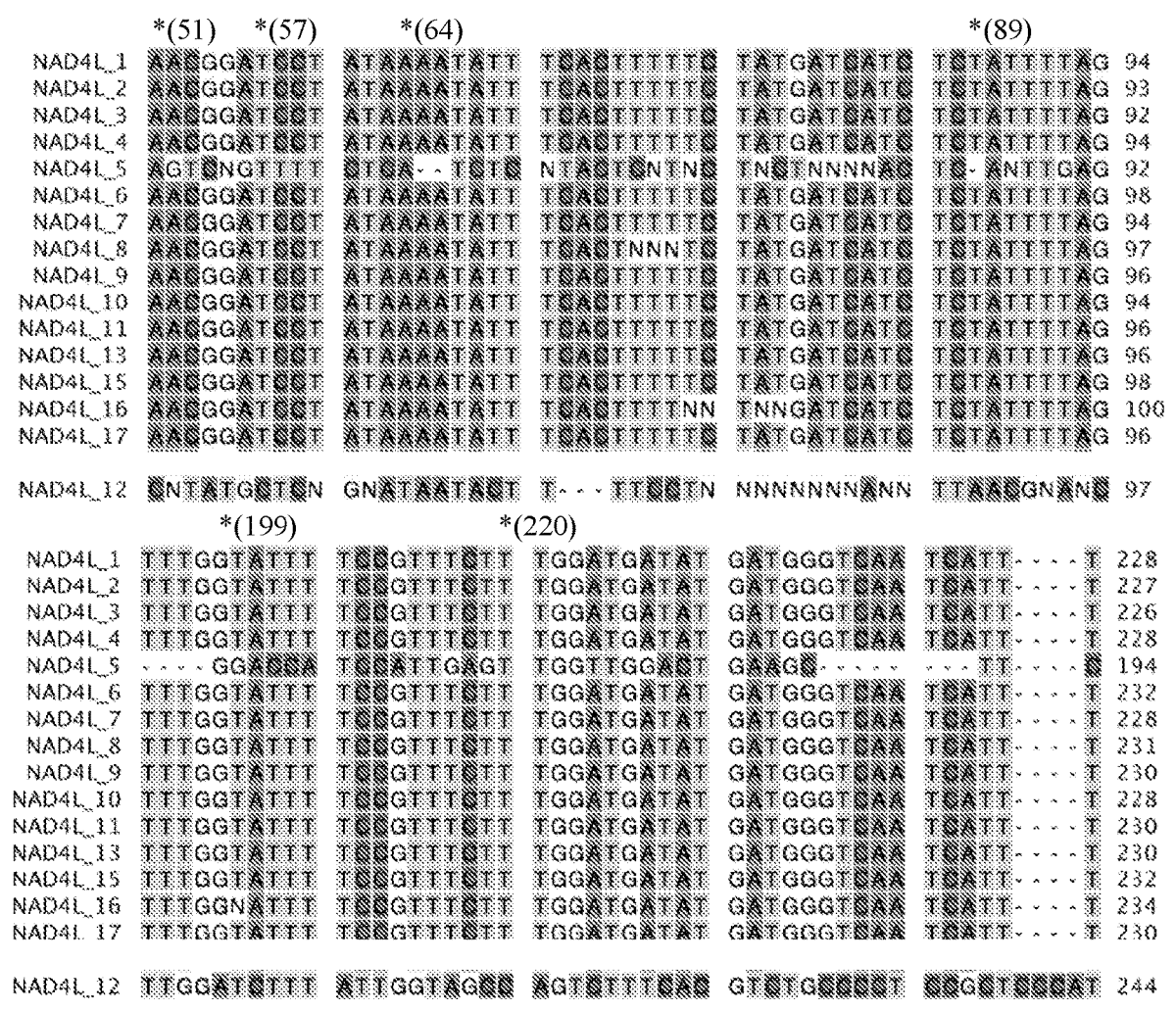

The sequences of FIG. 1 are, respectively SEQ ID NOS 1-16; in FIG. 2 are respectively SEQ ID NOS 17-32 and FIG. 3 are respectively 33-48; and in FIG. 4 are respectively 49-64. Based on sequence comparison of Cox3 gene, cytoplasm of line 343CMS didn't carry any distinct sequence change that differentiated it's Cox3 gene from other accessions under study (FIG. 1). Similar comparison for gene Atp8-1, revealed that line 3-4-3 carried sequence change at positions 155, 176, 186, 286, 295, and 337 bp (see SEQ ID NO: 32) that differentiated its cytoplasm from other accessions under study. (FIG. 2). Sequence comparison of gene NAD9 revealed that cytoplasmic gene NAD9 of lines 3-4-3 is distinct from all the known sources of cytoplasm sterility due to sequence change at position 170 and 338 bp. (SEQ ID NO 48 NAD 9-12 FIG. 3). Further sequence comparison based on gene NAD4L for all the accessions under study revealed that line 343CMS was carried sequence change at position 51, 54, 57, 89, 99, 106, 159, 181, 185, 199, 220, 226, and 425 to 429 bp. SEQ ID NO: 64).

TABLE 2

Accessions used to study the cytoplasmic diversity of Triticale line 343CMS

| | Material | Accession | Remarks |
|---|---|---|---|
| 1 | *Aegilops sharonensis* | TA#1996 | |
| 2 | *Ae. sharonensis* | TA#1998 | |
| 3 | *Ae. sharonensis* | TA#2174 | |
| 4 | *Ae. sharonensis* | TA#10414 | |
| 5 | *Ae. sharonensis* cytoplasm | TA#6003 | alloplasmic lines, Selkirk nucleus |
| 6 | *Ae. sharonensis* cytoplasm | TA#6005 | alloplasmic lines, Selkirk nucleus |
| 7 | *Ae. sharonensis* cytoplasm | TA#6006 | alloplasmic lines, Selkirk nucleus |
| 8 | *Triticum zhukovskyi* | TA#2610 | |
| 9 | *T. zhukovskyi* | TA#10866 | |
| 10 | Wheat A line | A 385-5 | *T. timopheevii* cytoplasm |
| 11 | Wheat B line | B 385-5 | *T. aestivum* cytoplasm |
| 12 | Triticale A line | 3-4-3 | Unknown cytoplasm |
| 13 | Triticale B line | 3-4-4 | Durum wheat cytoplasm |
| 16 | 718S | | *Ae. sharonensis* |
| 17 | SY718 | | Durum wheat cytoplasm |

A CLUSTAL, multiple sequence alignment by MUSCLE (3.8) of a wild type reference NAD9 nucleotide sequence (SEQ ID NO: 67; see GenBank AP008982.1) and the 434CMS NAD9 nucleotide sequence (SEQ:11) NO: 68) is shown below:

```
67 ATGCTCTGTATAATACTTTTCCCCGAGCGATGGTTTAGCGGATTCGGAATTGTAACCAAG
68 ATGCTCTGTATAATACTTTTCCCCGAGCGATGGTTTAGCGGATTCGGAATTGTAACCAAG
   ************************************************************

67 CATCCTGGGTTCTATACCCGATTCAACACTAGAGCATGCAGCCGATCCTGGATACATAAC
68 CATCCTGGGTTCTATACCCGATTCAACACTAGAGCATGCAGCCGATCCTGGATACATCAC
   ********************************************************** **

67 TCTAAAAAGTGTGTGTGCAGTTTTGGATCTTTATTGGTAGCCAGTCTTTCACTTCTGCCT
68 TATATAAAGTGTGCATGCAGTTTTGGATCTTTATTGGTAGCCAGTCTTTCACTTCTGCCT
   * ** ******* ***********************************************

67 CTCCACTCCCATGCCTTTCTTGGTCGGACCAACCCAACCGGCGATTTCCGACAAGTCTTT
68 CTCCACTCCCATGCCTTTCTTGGTCGGACCAACCCAACCGGCGATTTCCGACAAGTCTTT
   ************************************************************

67 CTGCTTAGAGCAAGAAGCGGAACCAAAATAAAGCTTTCTTTATTTTCATTTATGGATAAC
68 CTGCTTAGAGCAAGAAGCGGAACCAAAATAAAGCTTTCTTTATTTGCATTTATGGATAAC
   ********************************************* **************

67 CAATCCATTTTCCAATATAGTTGGGAGATTTTACCCAAGAAATGGGTACATAAAATGAAA
68 CAATCCATTTTCCAATATAGTTGGGAGATTTTACCCAAGAAATGGGTACATAAAATGAAA
   ************************************************************

67 AGATCGGAACATGGGAATAGATCTTATACCAATACTGACTACCCATTTCCATTGTTGTGC
68 AGATCGGAACATGGGAATAGATCTTATACCAATACTGACTACCCATTTCCATTGTTGTGC
   ************************************************************

67 TTTCTAAAATGGCATACCTATACAAGGGTTCAAGTTTCGATCGATATTTGCGGAGTGGAT
68 TTTCTAAAATGGCATACCTATACAAGGGTTCAAGTTTCGATCGATATTTGCGGAGTGGAT
   ************************************************************

67 CATCCCTCTCGAAAACGAAGATTTGAAGTTGTCCATAATTTACTGAGTACTCGGTATAAC
68 CATCCCTCTCGAAAACGAAGATTTGAAGTTGTCCATAATTTACTGAGTACTCGGTATAAC
   ************************************************************

67 TCACGCATTCGTGTACAAACAAGTGCAGACGAAGTAACACGAATATCTCCGGTAGTCAGT
68 TCACGCATTCGTGTACAAACAAGTGCAGACGAAGTAACACGAATATCTCCGGTAGTCAGT
   ************************************************************

67 CTATTTCCATCAGCCGGCCGGTGGGAGCGAGAAGTATGGGATATGTCTGGTGTTTCTTCC
68 CTATTTCCATCAGCCGGCCGGTGGGAGCGAGAAGTATGGGATATGTCTGGTGTTTCTTCC
   ************************************************************

67 ATCAATCATCCGGATTTACGCCGTATATCAACAGATTATGGTTTCGAGGGTCATCCATTA
68 ATCAATCATCCGGATTTACGCCGTATATCAACAGATTATGGTTTCGAGGGTCATCCATTA
   ************************************************************

67 CGAAAAGACTTTCCTCTGAGTGGATATGTGGAAGTACGCTATGATGATCCAGAGAAACGT
68 CGAAAAGACTTTCCTCTGAGTGGATATGTGGAAGTACGCTATGATGATCCAGAGAAACGT
   ************************************************************

67 GTGGTTTCTGAACCCATTGAGATGACCCAAGAATTTCGCTATTTCGATTTTGCTAGTCCT
68 GTGGTTTCTGAACCCATTGAGATGACCCAAGAATTTCGCTATTTCGATTTTGCTAGTCCT
   ************************************************************
```

```
67 TGGGAACAGCGTAGCGACGGATAA
68 TGGGAACAGCGTAGCGACGGATAA
   ************************
```

A CLUSTAL multiple sequence alignment by MUSCLE (3.8) of a wild type reference NAD9 protein (SEQ ID NO: 71; see GenBank AP008982.1) and the 434CMS NAD9 protein sequence (SEQ ID NO: 72) is shown below:

```
71 MLCIILFPERWFSGFGIVTKHPGFYTRFNTRACSRSWIHNSKKCVCSFGSLLVASLSLLP
72 MLCIILFPERWFSGFGIVTKHPGFYTRFNTRACSRSWIHHYIKCACSFGSLLVASLSLLP
   **************************************: **.****************

71 LHSHAFLGRTNPTGDFRQVFLLRARSGTKIKLSLFSFMDNQSIFQYSWEILPKKWVHKMK
72 LHSHAFLGRTNPTGDFRQVFLLRARSGTKIKLSLFAFMDNQSIFQYSWEILPKKWVHKMK
   ***********************************:************************

71 RSEHGNRSYTNTDYPFPLLCFLKWHTYTRVQVSIDICGVDHPSRKRRFEVVHNLLSTRYN
72 RSEHGNRSYTNTDYPFPLLCFLKWHTYTRVQVSIDICGVDHPSRKRRFEVVHNLLSTRYN
   ************************************************************

71 SRIRVQTSADEVTRISPVVSLFPSAGRWEREVWDMSGVSSINHPDLRRISTDYGFEGHPL
72 SRIRVQTSADEVTRISPVVSLFPSAGRWEREVWDMSGVSSINHPDLRRISTDYGFEGHPL
   ************************************************************

71 RKDFPLSGYVEVRYDDPEKRVVSEPIEMTQEFRYFDFASPWEQRSDG
72 RKDFPLSGYVEVRYDDPEKRVVSEPIEMTQEFRYFDFASPWEQRSDG
   ***********************************************
```

DEPOSIT

Applicant(s) have made a deposit of at least 625 seeds of triticale variety 343CMS with the American Type Culture Collection (ATCC), Manassas, Va. 20110 USA, ATCC Deposit No. PTA-126905. The seeds deposited with the ATCC on Nov. 24, 2020 were taken from the deposit maintained by Northern Agri Brands, LLC, 205 9$^{th}$ Ave. S., Suite 205, Great Falls, Mont. 59405, since prior to the filing date of this application. Access to this deposit will be available during the pendency of the application to the Commissioner of Patents and Trademarks and persons determined thereby to be entitled thereto upon request. Upon issue of claims, the Applicant(s) will make available to the public, pursuant to 37 CFR 1.808(2), a deposit of at least 625 seeds of variety 343CMS with the American type Culture Collection (ATCC), 10801 University Boulevard, Manassas, Va. 20110-2209. Additionally, Applicant(s) have satisfied all the requirements of 37 C.F.R. § 1.801-1.809, including providing an indication of the viability of the sample. These deposits will be maintained in the ATCC Depository, which is a public depository, for a period of 30 years, or 5 years after the most recent request, or for the enforceable life of the patent, whichever is longer, and will be replaced if it ever becomes nonviable during that period. Applicant has no authority to waive any restrictions imposed by law on the transfer of biological material or its transportation in commerce. Applicant does not waive any infringement of its rights granted under this patent or under the Plant Variety Protection Act (7 USC 2321 et seq.).

What is claimed is:

1. A seed of triticale cultivar 343CMS, wherein a representative sample of seed of said cultivar has been deposited under ATCC Accession No. PTA-126905.

2. A triticale plant, or a part thereof, produced by growing the seed of claim 1.

3. A tissue culture of cells produced from the plant of claim 2, wherein said cells of the tissue culture are produced from a plant part selected from the group consisting of heads, awns, leaves, pollen, embryos, cotyledons, hypocotyls, meristematic cells, roots, root tips, pistils, anthers, flowers, stems, and calli.

4. A protoplast produced from the plant of claim 2.

5. A protoplast produced from the tissue culture of claim 3.

6. A triticale plant regenerated from the tissue culture of claim 3, wherein the plant has all of the morphological and physiological characteristics of cultivar 343CMS wherein a representative sample of seed was deposited under ATCC Accession No. PTA-126905.

7. A method for producing an $F_1$ triticale seed, wherein the method comprises crossing the plant of claim 2 with a different triticale plant or a plant of 343CMS having restored male fertility and harvesting the resultant $F_1$ hybrid triticale seed.

8. A The $F_1$ hybrid triticale seed produced by the method of claim 7.

9. A triticale plant, or a part thereof, produced by growing said seed of claim 8.

10. An $F_1$ hybrid triticale plant or part thereof produced by crossing the triticale plant of claim 2, with a different triticale plant.

11. A method of introducing a desired trait into triticale cultivar 343CMS wherein the method comprises: (a) crossing a 343CMS plant, wherein a representative sample of seed was deposited under ATCC Accession No. PTA-126905, with a plant of another triticale cultivar that comprises a desired trait to produce progeny plants wherein the desired trait is selected from the group consisting of male sterility, herbicide resistance, insect resistance, modified fatty acid metabolism, modified carbohydrate metabolism, modified phytic metabolism, modified waxy starch content, modified gluten content and resistance to bacterial disease, fungal disease or viral disease; (b) selecting one or more progeny plants that have the desired trait to produce selected progeny plants; (c) crossing the selected progeny plants with the 343CMS plants to produce backcross progeny plants; (d) selecting for backcross progeny plants that have the desired trait and are otherwise phenotypically indistinguishable from triticale cultivar 343CMS listed in Table 1 to produce selected backcross progeny plants; and (e) repeating steps (c) and (d) three or more times in succession to produce selected fourth or higher backcross progeny plants that comprise the desired trait and are otherwise phenotypically indistinguishable from triticale cultivar 343CMS.

12. A triticale plant or plant part produced by the method of claim 11, wherein the plant has the desired trait and is otherwise phenotypically indistinguishable from triticale cultivar 343CMS.

13. A method of introducing male sterility into a desired triticale or wheat plant wherein the method comprises: (a) crossing a 343CMS plant, wherein a representative sample of seed was deposited under ATCC Accession No. PTA-126905, with the triticale or wheat plant to produce at least one progeny plant.

14. An $F_1$ male sterile plant produced by the method of claim 13.

15. The $F_1$ male sterile plant of claim 14, wherein the plant comprises the polynucleotide of SEQ ID NO: 64, 66, or 68.

16. The $F_1$ male sterile plant of claim 14, wherein the plant is a triticale plant.

17. The $F_1$ male sterile plant of claim 14, wherein the plant is a wheat plant.

18. The method of claim 13, further comprising the steps of: (b) selecting one or more progeny plants that have the male sterility trait to produce selected progeny plants; and (c) using the selected progeny plants as a source of breeding material to develop further progeny plants.

19. The method of claim 13, further comprising: assaying one or more progeny plants for the presence of the polynucleotide of SEQ ID NO: 64, 66, or 68.

20. A triticale or wheat plant comprising a mitochondrial polynucleotide associated with cytoplasmic male sterility as present in triticale cultivar 343CMS, wherein a representative sample of seed of the cultivar has been deposited under ATCC Accession No. PTA-126905, and wherein the plant is an $F_1$ progeny of triticale cultivar 343CMS.

21. The triticale or wheat plant of claim 20, wherein the plant comprises the polynucleotide of SEQ ID NO: 64, 66, or 68.

* * * * *

UNITED STATES PATENT AND TRADEMARK OFFICE
CERTIFICATE OF CORRECTION

PATENT NO. : 11,700,810 B2
APPLICATION NO. : 16/949918
DATED : July 18, 2023
INVENTOR(S) : Rollin George Sears It is certified that error appears in the above-identified patent and that said Letters Patent is hereby corrected as shown below:

In the Claims

In Claim 11, Column 262, at Line 34:
DELETE: "in Table 1"

Signed and Sealed this
Third Day of October, 2023

Katherine Kelly Vidal
*Director of the United States Patent and Trademark Office*

SEQUENCE LISTING

```
<160> NUMBER OF SEQ ID NOS: 72

<210> SEQ ID NO 1
<211> LENGTH: 1005
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
```

```
<222> LOCATION: (868)..(869)
<223> OTHER INFORMATION: n is a, c, g, or t
<220> FEATURE:
<221> NAME/KEY: misc_feature
<222> LOCATION: (872)..(872)
<223> OTHER INFORMATION: n is a, c, g, or t
<220> FEATURE:
<221> NAME/KEY: misc_feature
<222> LOCATION: (885)..(886)
<223> OTHER INFORMATION: n is a, c, g, or t
<220> FEATURE:
<221> NAME/KEY: misc_feature
<222> LOCATION: (917)..(917)
<223> OTHER INFORMATION: n is a, c, g, or t
<220> FEATURE:
<221> NAME/KEY: misc_feature
<222> LOCATION: (924)..(926)
<223> OTHER INFORMATION: n is a, c, g, or t
<220> FEATURE:
<221> NAME/KEY: misc_feature
<222> LOCATION: (948)..(953)
<223> OTHER INFORMATION: n is a, c, g, or t
<220> FEATURE:
<221> NAME/KEY: misc_feature
<222> LOCATION: (957)..(958)
<223> OTHER INFORMATION: n is a, c, g, or t
<220> FEATURE:
<221> NAME/KEY: misc_feature
<222> LOCATION: (964)..(967)
<223> OTHER INFORMATION: n is a, c, g, or t
<220> FEATURE:
<221> NAME/KEY: misc_feature
<222> LOCATION: (969)..(970)
<223> OTHER INFORMATION: n is a, c, g, or t
<220> FEATURE:
<221> NAME/KEY: misc_feature
<222> LOCATION: (991)..(994)
<223> OTHER INFORMATION: n is a, c, g, or t
<220> FEATURE:
<221> NAME/KEY: misc_feature
<222> LOCATION: (996)..(998)
<223> OTHER INFORMATION: n is a, c, g, or t
<220> FEATURE:
<221> NAME/KEY: misc_feature
<222> LOCATION: (1004)..(1004)
<223> OTHER INFORMATION: n is a, c, g, or t

<400> SEQUENCE: 1
nnnnnnnnnn nagnttctac cgganagtca ngacgaaaac gtgtgccaac ccctatgcat      60
aagttcattg aacccgcaag ttgatcacca aaacatacat caagtagatc acgtgaatat     120
cccattgtca ccacggataa gacgcgagac aatttatcct ttataccatg ttcgtatggt     180
ggcgggatgt tctacgtgaa tccatgttgg aagggcatca tacaaaagct gtacaattag     240
gacctcgata tggttctatt ctcttcatag tctcggaggt tatgttcctt tttgcttttt     300
ttgggcttct tctcattctt ctttggcacc tacggtagag atcggaggta tttggccccc     360
aaaagggatt ggggttttag atccttggga aatccctctt cttaatacccc ctattctccc     420 ttcatccgga gctgtcgtaa cttgggctca tcatgctata ctcgcgggga aggaaaaacg     480
agcagtttac gctttagtag caaccgtttc actggctcta gtatccactg gtttcaaggt     540
atggaatatt accaagcacc ctccactatt tcggatagta tttatggttc tacctttttc     600
ttagcaactg gctttcatgg gtttcatgtg attataggta ctcttttctt gatcgtatgt     660
ggtattcgcc aatatcttgg tcagatgacc aagaagcatc acgttggctt tgaagcagct     720
gcatggtact ggcattttgt agacgtggtt cggttattcc catttgtctc tatctattgg     780
tggggaggta tatgaaagaa gggaacgaat aagtggattg aggaataaaa gctcgaagac     840
aaagagaact tctccgggta ctcaagannt tntgtttgga gaggnntaga ttgtagattc     900
```

```
cagccgagcc agacccngga agannntgaa gtccaatttc ctcaaccnnn nnncggnnag    960
aacnnnngnn aaaagggaa aaccggaacc nnnntnnnaa aatng                    1005
```

<210> SEQ ID NO 2
<211> LENGTH: 1011
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (13)..(19)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t
<220> FEATURE:
<221> NAME/KEY: misc_feature
<222> LOCATION: (956)..(957)
<223> OTHER INFORMATION: n is a, c, g, or t
<220> FEATURE:
<221> NAME/KEY: misc_feature
<222> LOCATION: (959)..(964)
<223> OTHER INFORMATION: n is a, c, g, or t
<220> FEATURE:
<221> NAME/KEY: misc_feature
<222> LOCATION: (968)..(968)
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t
<220> FEATURE:
<221> NAME/KEY: misc_feature
<222> LOCATION: (982)..(983)
<223> OTHER INFORMATION: n is a, c, g, or t
<220> FEATURE:
<221> NAME/KEY: misc_feature
<222> LOCATION: (998)..(1000)
<223> OTHER INFORMATION: n is a, c, g, or t
<220> FEATURE:
<221> NAME/KEY: misc_feature
<222> LOCATION: (1002)..(1004)
<223> OTHER INFORMATION: n is a, c, g, or t
<220> FEATURE:
<221> NAME/KEY: misc_feature
<222> LOCATION: (1007)..(1009)
<223> OTHER INFORMATION: n is a, c, g, or t

<400> SEQUENCE: 2

```
nnnnnnnnnn ngnnnnnnnt atcatttggt agatccaagt ccatggccta tttcgggttc    60 actcggggt ttggcaacca ccgtaggagg tgtgatgtac atgcactcat ttcaaggggg    120
tgcaacactt ctcagtttgg gcctaatatt tatcctttat accatgttcg tatggtggcg    180
ggatgttcta cgtgaatcca cgttggaagg gcatcataca aaagctgtac aattaggacc    240
tcaatatggt tctattctct tcatagtctc ggaggttatg ttccctttg cttttttttg     300 ggcttcttct cattcttctt tggcacctac ggtagagatc ggaggtattt ggcccccaaa    360
```

```
agggattggt gttttagatc cttgggaaat ccctcttctt aatacccta ttctcccttc    420 atccggagct gccgtaactt gggctcatca tgctatactc gcggggaagg aaaaacgagc    480
agtttatgct ttagtagcaa ccgtttcact ggctctagta tccactggct ttcaaggaat    540
ggaatattac caagcaccct ccactatttc ggatagtatt tatggttcta cctttttctt    600
agcaactggc tttcatggtt ttcatgtgat tataggtact cttttcttga tcgtatgtgg    660
tattcgccaa tatcttggtc atctgaccaa gaagcatcac gttggctttg aagcagctgc    720
atggtactgg cattttatag acgtggttcg gttattccca tttgtctcta tctattggng    780
gggaggtata tgaaagaagg gaacgaataa gtggattgag gaataaaagc tcgaagacaa    840
agagaacttc tccgggtact caagatattg tgtttggaga ggtgtagatt gtagattcca    900
gccgagccag acccaggaan atacaaagtc catttcctca acncnnnacg atagannghn    960
nnnnaaangg gaanaccgaa cnnggccaaa aaaggcannn cnnnggnnnt t            1011
```

<210> SEQ ID NO 3
<211> LENGTH: 1032
<212> TYPE: DNA
<213> ORGANISM: Aegilops sharonensis
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (953)..(954)
<223> OTHER INFORMATION: n is a, c, g, or t
<220> FEATURE:
<221> NAME/KEY: misc_feature
<222> LOCATION: (962)..(963)
<223> OTHER INFORMATION: n is a, c, g, or t
<220> FEATURE:
<221> NAME/KEY: misc_feature
<222> LOCATION: (965)..(970)
<223> OTHER INFORMATION: n is a, c, g, or t
<220> FEATURE:
<221> NAME/KEY: misc_feature
<222> LOCATION: (978)..(979)
<223> OTHER INFORMATION: n is a, c, g, or t
<220> FEATURE:
<221> NAME/KEY: misc_feature
<222> LOCATION: (983)..(984)
<223> OTHER INFORMATION: n is a, c, g, or t
<220> FEATURE:
<221> NAME/KEY: misc_feature
<222> LOCATION: (996)..(1001)
<223> OTHER INFORMATION: n is a, c, g, or t
<220> FEATURE:
<221> NAME/KEY: misc_feature
<222> LOCATION: (1005)..(1006)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1012)..(1013)
<223> OTHER INFORMATION: n is a, c, g, or t
<220> FEATURE:
<221> NAME/KEY: misc_feature
<222> LOCATION: (1016)..(1031)
<223> OTHER INFORMATION: n is a, c, g, or t

<400> SEQUENCE: 3

-continued

| | |
|---|---|
| nnnnnnnnnn nngnggcatt cttatcattt ggtagatcca agtccatggc ctatttcggg | 60 |
| ttcactcgga gctttggcaa ccaccgtagg aggtgtgatg tacatgcact catttcaagg | 120 |
| gggtgcaaca cttctcagtt tgggcctaat atttatcctt tataccatgt tcgtatggtg | 180 |
| gcgggatgtt ctacgtgaat ccatgttgga agggcatcat acaaaagctg tacaattagg | 240 |
| acctcgatat ggttctattc tcttcatagt ctcggaggtt atgttccttt ttgcttttt | 300 |
| tgggcttctt ctcattcttc tttggcacct acggtagaga tcggaggtat ttggccccca | 360 |
| aaagggattg gggttttaga tccttgggaa atccctcttc ttaatacccc tattctccct | 420 |
| tcatccggag ctgccgtaac ttgggctcat catgctatac tcgcggggaa ggaaaaacga | 480 |
| gcagtttatg ctttagtagc aaccgtttca ctggctctag tatccactgg cttcaaggt | 540 |
| atggaatatt accaagcacc ctccactatt tcggatagta tttatggttc tacctttttc | 600 |
| ttagcaactg gctttcatgg ttttcatgtg attataggta ctcttttctt gatcgtatgt | 660 |
| ggtattcgcc aatatcttgg tcagatgacc aagaagcatc acgttggctt tgaagcagct | 720 |
| gcatggtact ggcattttgt agacgtggtt cggttattcc catttgtctc tatctattgg | 780 |
| tggggaggta tatgaaagaa gggaacgaat aagtggattg aggaataaaa gctcgaagac | 840 |
| aaagagaact tctccgggta ctcaagatat tgtgtttgga gaggtgtaga ttgtagattc | 900 |
| cagccgagcc agacccagga agaatatgaa gtccaatttc ctcaaccgcg canncgtaga | 960 |
| anngnnnnnn acaaaggnng aannacggaa ccacgnnnnn naaanngccn gnnccnnnnn | 1020 |
| nnnnnnnnnn ng | 1032 |

```
<210> SEQ ID NO 4
<211> LENGTH: 1024
<212> TYPE: DNA
<213> ORGANISM: Aegilops sharonensis
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (8)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (952)..(955)
<223> OTHER INFORMATION: n is a, c, g, or t
<220> FEATURE:
<221> NAME/KEY: misc_feature
<222> LOCATION: (963)..(971)
<223> OTHER INFORMATION: n is a, c, g, or t
<220> FEATURE:
<221> NAME/KEY: misc_feature
<222> LOCATION: (987)..(988)
<223> OTHER INFORMATION: n is a, c, g, or t
<220> FEATURE:
<221> NAME/KEY: misc_feature
<222> LOCATION: (992)..(998)
<223> OTHER INFORMATION: n is a, c, g, or t
<220> FEATURE:
<221> NAME/KEY: misc_feature
<222> LOCATION: (1009)..(1011)
<223> OTHER INFORMATION: n is a, c, g, or t
<220> FEATURE:
<221> NAME/KEY: misc_feature
```

```
<222> LOCATION: (1015)..(1015)
<223> OTHER INFORMATION: n is a, c, g, or t
<220> FEATURE:
<221> NAME/KEY: misc_feature
<222> LOCATION: (1017)..(1018)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t

<400> SEQUENCE: 4
nnnnnntnnn nnnnnggcnt tcttatcatt tggtagatcc aagtccatgg cctatttcgg      60
gttcacntcg ggggtttggc aaccaccgta ggaggtgtga tgtacatgca ctcatttcaa     120 ggggtgcaa cacttctcag tttgggccta atatttatcc tttataccat gttcgtatgg     180
tggcgggatg ttctacgtga atccacgttg aagggcatc atacaaaagc tgtacaatta     240
ggacctcaat atggttctat tctcttcata gtctcggagg ttatgttccc ttttgctttt     300
ttttgggctt cttctcattc ttctttggca cctacggtag agatcggagg tatttggccc     360
ccaaaaggga ttggtgtttt agatccttgg gaaatccctc ttcttaatac ccctattctc     420
ccttcatccg gagctgccgt aacttgggct catcatgcta tactcgcggg gaaggaaaaa     480
cgagcagttt atgctttagt agcaaccgtt tcactggctc tagtatccac tggctttcaa     540
ggaatggaat attaccaagc accctccact atttcggata gtatttatgg ttctaccttt     600
ttcttagcaa ctggctttca tggttttcat gtgattatag gtactctttt cttgatcgta     660
tgtggtattc gccaatatct tggtcatctg accaagaagc atcacgttgg ctttgaagca     720
gctgcatggt actggcattt tatagacgtg gttcggttat tcccatttgt ctctatctat     780
tggtggggag gtatatgaaa gaagggaacg aataagtgga ttgaggaata aaagctcgaa     840
gacaaagaga acttctccgg gtactcaaga tattgtgttt ggagaggtgt agattgtaga     900
ttccagccga gccagaccca ggaagaatac aaagtccaat ttcctcaacg cnnnncgtag     960
aannnnnnnn naaaaagggg aataccnnac cnnnnnnnaa aaatgccann nccangnngn    1020
gggg                                                                 1024

<210> SEQ ID NO 5
<211> LENGTH: 1089
<212> TYPE: DNA
<213> ORGANISM: Aegilops sharonensis
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (836)..(837)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
```

```
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (867)..(869)
<223> OTHER INFORMATION: n is a, c, g, or t
<220> FEATURE:
<221> NAME/KEY: misc_feature
<222> LOCATION: (890)..(891)
<223> OTHER INFORMATION: n is a, c, g, or t
<220> FEATURE:
<221> NAME/KEY: misc_feature
<222> LOCATION: (899)..(900)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (904)..(904)
<223> OTHER INFORMATION: n is a, c, g, or t
<220> FEATURE:
<221> NAME/KEY: misc_feature
<222> LOCATION: (912)..(913)
<223> OTHER INFORMATION: n is a, c, g, or t
<220> FEATURE:
<221> NAME/KEY: misc_feature
<222> LOCATION: (916)..(917)
<223> OTHER INFORMATION: n is a, c, g, or t
<220> FEATURE:
<221> NAME/KEY: misc_feature
<222> LOCATION: (919)..(921)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (927)..(928)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (932)..(938)
<223> OTHER INFORMATION: n is a, c, g, or t
<220> FEATURE:
<221> NAME/KEY: misc_feature
<222> LOCATION: (941)..(942)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t
<220> FEATURE:
<221> NAME/KEY: misc_feature
<222> LOCATION: (946)..(956)
<223> OTHER INFORMATION: n is a, c, g, or t
<220> FEATURE:
<221> NAME/KEY: misc_feature
<222> LOCATION: (959)..(961)
<223> OTHER INFORMATION: n is a, c, g, or t
<220> FEATURE:
<221> NAME/KEY: misc_feature
<222> LOCATION: (964)..(967)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (971)..(972)
<223> OTHER INFORMATION: n is a, c, g, or t
```

```
<220> FEATURE:
<221> NAME/KEY: misc_feature
<222> LOCATION: (974)..(975)
<223> OTHER INFORMATION: n is a, c, g, or t
<220> FEATURE:
<221> NAME/KEY: misc_feature
<222> LOCATION: (977)..(981)
<223> OTHER INFORMATION: n is a, c, g, or t
<220> FEATURE:
<221> NAME/KEY: misc_feature
<222> LOCATION: (984)..(985)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (989)..(990)
<223> OTHER INFORMATION: n is a, c, g, or t
<220> FEATURE:
<221> NAME/KEY: misc_feature
<222> LOCATION: (992)..(993)
<223> OTHER INFORMATION: n is a, c, g, or t
<220> FEATURE:
<221> NAME/KEY: misc_feature
<222> LOCATION: (995)..(996)
<223> OTHER INFORMATION: n is a, c, g, or t
<220> FEATURE:
<221> NAME/KEY: misc_feature
<222> LOCATION: (998)..(999)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1022)
<223> OTHER INFORMATION: n is a, c, g, or t
<220> FEATURE:
<221> NAME/KEY: misc_feature
<222> LOCATION: (1024)..(1024)
<223> OTHER INFORMATION: n is a, c, g, or t
<220> FEATURE:
<221> NAME/KEY: misc_feature
<222> LOCATION: (1026)..(1038)
<223> OTHER INFORMATION: n is a, c, g, or t
<220> FEATURE:
<221> NAME/KEY: misc_feature
<222> LOCATION: (1040)..(1054)
<223> OTHER INFORMATION: n is a, c, g, or t
<220> FEATURE:
<221> NAME/KEY: misc_feature
<222> LOCATION: (1056)..(1058)
<223> OTHER INFORMATION: n is a, c, g, or t
<220> FEATURE:
<221> NAME/KEY: misc_feature
<222> LOCATION: (1060)..(1060)
<223> OTHER INFORMATION: n is a, c, g, or t
<220> FEATURE:
<221> NAME/KEY: misc_feature
<222> LOCATION: (1062)..(1069)
<223> OTHER INFORMATION: n is a, c, g, or t
<220> FEATURE:
<221> NAME/KEY: misc_feature
<222> LOCATION: (1071)..(1072)
<223> OTHER INFORMATION: n is a, c, g, or t
<220> FEATURE:
<221> NAME/KEY: misc_feature
<222> LOCATION: (1074)..(1078)
<223> OTHER INFORMATION: n is a, c, g, or t
<220> FEATURE:
<221> NAME/KEY: misc_feature
<222> LOCATION: (1081)..(1089)
<223> OTHER INFORMATION: n is a, c, g, or t

<400> SEQUENCE: 5
```

| | |
|---|---|
| nnnnnnnnnn nnnnngnnnn ntatcatttg gtagatccaa gtccatggcc tatttcgggt | 60 |
| tcactcgggg gtttggcaac caccgtagga ggtgtgatgt acatgcactc atttcaaggg | 120 |
| ggtgcaacac ttctcagttt gggcctaata tttatccttt ataccatgtt cgtatggtgg | 180 |
| cgggatgttc tacgtgaatc cacgttggaa gggcatcata caaaagctgt acaattagga | 240 |
| cctcaatatg gttctattct cttcatagtc tcggaggtta tgttcccttt tgctttttt | 300 |
| tgggcttctt ctcattcttc tttggcacct acggtagaga tcggaggtat ttggccccca | 360 |
| aaagggattg gtgttttaga tccttgggaa atccctcttc ttaataccc tattctccct | 420 |
| tcatccggag ctgccgtaac ttgggctcat catgctatac tcgcggggaa ggaaaaacga | 480 |
| gcagtttatg ctttagtagc aaccgtttca ctggctctag tatccactgg cttttcaagga | 540 |
| atggaatatt accaagcacc ctccactatt tcggatagta tttatggttc tacctttttc | 600 |
| ttagcaactg gctttcatgg ttttcatgtg attataggta ctctttctt gatcgtatgt | 660 |
| ggtattcgcc aatatcttgg tcatctgacc aagaagcatc acgttggctt tgaagcagct | 720 |
| gcatggtact ggcattttat agacgtggtt cggttattcc catttgtctc tatctattgg | 780 |
| tggggaggta tatgaaagaa ggnacgaata agtggattga ggaataaaag ctcgannaca | 840 |
| aagagaactt cnncggnac tcaagannnt gtgtttggag aggtgtagan ntagattcnn | 900 |
| cnancagacc cnngannann naantcnntn cnnnnnnnca nngnannnnn nnnnnnaann | 960 |
| nggnnnncng nncnngnnnn naanncgnn cnngnngnng ntnnnnnnnn nnnnnnnnn | 1020 |
| nntntnnnnn nnnnnnntn nnnnnnnnnn nnnncnnnan annnnnnnnt nntnnnnnca | 1080 |
| nnnnnnnnn | 1089 |

```
<210> SEQ ID NO 6
<211> LENGTH: 889
<212> TYPE: DNA
<213> ORGANISM: Aegilops sharonensis
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (307)..(308)
<223> OTHER INFORMATION: n is a, c, g, or t
<220> FEATURE:
<221> NAME/KEY: misc_feature
<222> LOCATION: (310)..(311)
<223> OTHER INFORMATION: n is a, c, g, or t
<220> FEATURE:
<221> NAME/KEY: misc_feature
<222> LOCATION: (313)..(317)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (329)..(330)
<223> OTHER INFORMATION: n is a, c, g, or t
<220> FEATURE:
<221> NAME/KEY: misc_feature
<222> LOCATION: (333)..(338)
<223> OTHER INFORMATION: n is a, c, g, or t
```

```
<220> FEATURE:
<221> NAME/KEY: misc_feature
<222> LOCATION: (340)..(347)
<223> OTHER INFORMATION: n is a, c, g, or t
<220> FEATURE:
<221> NAME/KEY: misc_feature
<222> LOCATION: (349)..(351)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (377)..(378)
<223> OTHER INFORMATION: n is a, c, g, or t
<220> FEATURE:
<221> NAME/KEY: misc_feature
<222> LOCATION: (388)..(391)
<223> OTHER INFORMATION: n is a, c, g, or t
<220> FEATURE:
<221> NAME/KEY: misc_feature
<222> LOCATION: (394)..(396)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (403)..(404)
<223> OTHER INFORMATION: n is a, c, g, or t
<220> FEATURE:
<221> NAME/KEY: misc_feature
<222> LOCATION: (409)..(411)
<223> OTHER INFORMATION: n is a, c, g, or t
<220> FEATURE:
<221> NAME/KEY: misc_feature
<222> LOCATION: (414)..(415)
<223> OTHER INFORMATION: n is a, c, g, or t
<220> FEATURE:
<221> NAME/KEY: misc_feature
<222> LOCATION: (419)..(421)
<223> OTHER INFORMATION: n is a, c, g, or t
<220> FEATURE:
<221> NAME/KEY: misc_feature
<222> LOCATION: (426)..(429)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (443)..(444)
<223> OTHER INFORMATION: n is a, c, g, or t
<220> FEATURE:
<221> NAME/KEY: misc_feature
<222> LOCATION: (447)..(450)
<223> OTHER INFORMATION: n is a, c, g, or t
<220> FEATURE:
<221> NAME/KEY: misc_feature
<222> LOCATION: (453)..(462)
<223> OTHER INFORMATION: n is a, c, g, or t
<220> FEATURE:
<221> NAME/KEY: misc_feature
<222> LOCATION: (474)..(478)
<223> OTHER INFORMATION: n is a, c, g, or t
<220> FEATURE:
<221> NAME/KEY: misc_feature
<222> LOCATION: (481)..(481)
<223> OTHER INFORMATION: n is a, c, g, or t
<220> FEATURE:
<221> NAME/KEY: misc_feature
<222> LOCATION: (485)..(487)
<223> OTHER INFORMATION: n is a, c, g, or t
<220> FEATURE:
<221> NAME/KEY: misc_feature
<222> LOCATION: (491)..(495)
```

```
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (508)..(509)
<223> OTHER INFORMATION: n is a, c, g, or t
<220> FEATURE:
<221> NAME/KEY: misc_feature
<222> LOCATION: (511)..(512)
<223> OTHER INFORMATION: n is a, c, g, or t
<220> FEATURE:
<221> NAME/KEY: misc_feature
<222> LOCATION: (514)..(515)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (575)..(577)
<223> OTHER INFORMATION: n is a, c, g, or t
<220> FEATURE:
<221> NAME/KEY: misc_feature
<222> LOCATION: (587)..(588)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t
<220> FEATURE:
<221> NAME/KEY: misc_feature
```

```
<222> LOCATION: (648)..(650)
<223> OTHER INFORMATION: n is a, c, g, or t
<220> FEATURE:
<221> NAME/KEY: misc_feature
<222> LOCATION: (658)..(664)
<223> OTHER INFORMATION: n is a, c, g, or t
<220> FEATURE:
<221> NAME/KEY: misc_feature
<222> LOCATION: (694)..(695)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t
<220> FEATURE:
<221> NAME/KEY: misc_feature
<222> LOCATION: (765)..(766)
<223> OTHER INFORMATION: n is a, c, g, or t
<220> FEATURE:
<221> NAME/KEY: misc_feature
<222> LOCATION: (768)..(771)
<223> OTHER INFORMATION: n is a, c, g, or t
<220> FEATURE:
<221> NAME/KEY: misc_feature
<222> LOCATION: (780)..(782)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (795)..(797)
<223> OTHER INFORMATION: n is a, c, g, or t
<220> FEATURE:
<221> NAME/KEY: misc_feature
<222> LOCATION: (799)..(800)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (826)..(828)
<223> OTHER INFORMATION: n is a, c, g, or t
<220> FEATURE:
<221> NAME/KEY: misc_feature
<222> LOCATION: (841)..(843)
<223> OTHER INFORMATION: n is a, c, g, or t
<220> FEATURE:
<221> NAME/KEY: misc_feature
<222> LOCATION: (847)..(848)
<223> OTHER INFORMATION: n is a, c, g, or t
<220> FEATURE:
<221> NAME/KEY: misc_feature
<222> LOCATION: (850)..(857)
<223> OTHER INFORMATION: n is a, c, g, or t
<220> FEATURE:
```

```
<221> NAME/KEY: misc_feature
<222> LOCATION: (873)..(874)
<223> OTHER INFORMATION: n is a, c, g, or t
<220> FEATURE:
<221> NAME/KEY: misc_feature
<222> LOCATION: (877)..(878)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (884)..(885)
<223> OTHER INFORMATION: n is a, c, g, or t
<220> FEATURE:
<221> NAME/KEY: misc_feature
<222> LOCATION: (887)..(887)
<223> OTHER INFORMATION: n is a, c, g, or t

<400> SEQUENCE: 6
nnnnnnnnnn nnnngnggca ttcttatcat ttggtagatc caagtccatg gcctatttcg      60
ggttcactcg gagctttggc aaccaccgta ggaggtgtga tgtacatgca ctcatttcaa     120
gggggtgcaa cacttctcag tttgggccta atatttatcc tttataccat gttcgtatgg     180
tggcgggatg ttctacgtga atccacgttg gaagggcatc atacaaaagc tgtacaatta     240
ggacctcgat atggttctat tctcttcata gtctcggagg ttatgttcct ttttgctttt     300
tttgggnntn ntnnnnntcn tcnttggcnn ctnnnnnngn nnnnnnngnn nttggccccc     360
aaaagggang gggtttnnat ccttgggnnn nccnnntctt nanncccnn ntcnncctnn      420 nccgnnnng ccnnaacttg ggnncannnn gcnnnnnnnn nngggaagaa aaannnnnag      480
nttannnttt nnnnnaccgt ttnctggnnc nngnntncct ggctttnaag gaaggaaatt     540
accaancccc tncntatttc ggaagnattn ggttnnncct tttttnnaa cngtttnngg      600 tttctgnntt nnggnctctt tttgacgatg ggnntcccaa ttttggcnnn gacaaaannn     660
nnnntggctt gagcactgct ggactggatt tganncgggt tggtattcca ttgttcttct    720 ntgnggagt nttgaanagg acgatagtga tgagaaaaag nngannannn nactctcggn     780
nncannatgt gttgnnngnn aatgtaatcn gcnagcaacc agaganwnag tcattctcac    840
nnnacgnnan nnnnnnnaag ggaaacgacc ggnnaanncg gncnngngg                889

<210> SEQ ID NO 7
<211> LENGTH: 1045
<212> TYPE: DNA
<213> ORGANISM: Aegilops sharonensis
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (8)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
```

<222> LOCATION: (340)..(341)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (846)..(848)
<223> OTHER INFORMATION: n is a, c, g, or t
<220> FEATURE:
<221> NAME/KEY: misc_feature
<222> LOCATION: (870)..(871)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (949)..(955)
<223> OTHER INFORMATION: n is a, c, g, or t
<220> FEATURE:
<221> NAME/KEY: misc_feature
<222> LOCATION: (964)..(973)
<223> OTHER INFORMATION: n is a, c, g, or t
<220> FEATURE:
<221> NAME/KEY: misc_feature
<222> LOCATION: (978)..(979)
<223> OTHER INFORMATION: n is a, c, g, or t
<220> FEATURE:
<221> NAME/KEY: misc_feature
<222> LOCATION: (986)..(988)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (996)..(997)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1007)..(1008)
<223> OTHER INFORMATION: n is a, c, g, or t
<220> FEATURE:
<221> NAME/KEY: misc_feature
<222> LOCATION: (1014)..(1017)
<223> OTHER INFORMATION: n is a, c, g, or t
<220> FEATURE:
<221> NAME/KEY: misc_feature
<222> LOCATION: (1020)..(1021)
<223> OTHER INFORMATION: n is a, c, g, or t
<220> FEATURE:
<221> NAME/KEY: misc_feature
<222> LOCATION: (1023)..(1025)
<223> OTHER INFORMATION: n is a, c, g, or t
<220> FEATURE:
<221> NAME/KEY: misc_feature
<222> LOCATION: (1027)..(1033)
<223> OTHER INFORMATION: n is a, c, g, or t

<400> SEQUENCE: 7
nnnnnntnnn nncngnngcn ttcttatcat ttggtagatc caagtccatg gcctatttcg      60
ggttcactcg gagctttggc aaccaccgta ggaggtgtga tgtacatgca ctcatttcaa     120 ggggggtgcaa cacttctcag tttgggccta atatttatcc tttataccat gttcgtatgg    180
tggcgggatg ttctacgtga atccacgttg gaagggcatc atacaaaagc tgtacaatta    240
ggacctcgat atggttctat tctcttcata gtctcggagg ttatgttcct ttttgctttt    300

-continued

```
tttgggcttc ttctcattct tctttggcac ctacggtagn natcggaggt atttggcccc    360
caaaagggat tggggtttta natccttggg aaatccctct tcttaatacc cctattctcc    420
cttcatccgg agctgccgta acttgggctc atcatgctat actcgcgggg aaggaaaaac    480
gagcagttta cgctttagta gcaaccgttt cactggctct agtatccact ggctttcaag    540
gaatggaata ttaccaagca ccctccacta tttcggatag tatttatggt tctaccttt    600 tcttagcaac tggctttcat ggttttcatg tgattatagg tactcttttc ttgatcgtat    660
gtggtattcg ccaatatctt ggtcatctga ccaagaagca tcacgttggc tttgaagcag    720
ctgcatggta ctggcatttt gtagacgtgg ttcggttatt cccatttgtc tctatctatt    780
ggtggggagg tatatgaaag aagggaacga ataagtggat tgaggaataa aagctcgaag    840
acaaannnaa cttctccggg tactcaagan nttgtntttg gagaggtgta gattgtagat    900
tccagccgag ccagacccag gaagaatacg aagtccaatt tcctcaacnn nnnncgtag    960 aaannnnnnn nnnaaaanng gggaannncg gaancnnggt tnaaaanngg ccannnncan   1020
ngnnngnnnn nnnaggcccc ccccc                                          1045
```

<210> SEQ ID NO 8
<211> LENGTH: 1047
<212> TYPE: DNA
<213> ORGANISM: Triticum zhukovskyi
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (949)..(951)
<223> OTHER INFORMATION: n is a, c, g, or t
<220> FEATURE:
<221> NAME/KEY: misc_feature
<222> LOCATION: (963)..(969)
<223> OTHER INFORMATION: n is a, c, g, or t
<220> FEATURE:
<221> NAME/KEY: misc_feature
<222> LOCATION: (977)..(977)
<223> OTHER INFORMATION: n is a, c, g, or t
<220> FEATURE:
<221> NAME/KEY: misc_feature
<222> LOCATION: (995)..(996)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t
<220> FEATURE:
<221> NAME/KEY: misc_feature
<222> LOCATION: (1010)..(1014)
<223> OTHER INFORMATION: n is a, c, g, or t
<220> FEATURE:
<221> NAME/KEY: misc_feature
<222> LOCATION: (1016)..(1018)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1026)..(1028)
<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1039)..(1041)
<223> OTHER INFORMATION: n is a, c, g, or t
<220> FEATURE:
<221> NAME/KEY: misc_feature
<222> LOCATION: (1043)..(1046)
<223> OTHER INFORMATION: n is a, c, g, or t

<400> SEQUENCE: 8

| | | | | | |
|---|---|---|---|---|---|
| nnnnnnnnnn | nnnnnnnnnt | tcttancant | tggtagatcc | aagtccatgg | cctatttcgg | 60 |
| gttcactcgg | agctttggca | accaccgtag | gaggtgtgat | gtacatgcac | tcatttcaag | 120 |
| ggggtgcaac | acttctcagt | ttgggcctaa | tatttatcct | ttataccatg | ttcgtatggt | 180 |
| ggcgggatgt | tctacgtgaa | tccacgttgg | aagggcatca | tacaaaagct | gtacaattag | 240 |
| gacctcgata | tggttctatt | ctcttcatag | tctcggaggt | tatgttcctt | tttgcttttt | 300 |
| tttgggcttc | ttctcattct | tctttggcac | ctacggtaga | gatcggaggt | atttggcccc | 360 |
| caaaagggat | tggggtttta | gatccttggg | aaatccctct | tcttaatacc | cctattctcc | 420 |
| cttcatccgg | agctgccgta | acttgggctc | atcatgctat | actcgcgggg | aaggaaaaac | 480 |
| gagcagttta | cgctttagta | gcaaccgttt | cactggctct | agtatccact | ggctttcaag | 540 |
| gaatggaata | ttaccaagca | ccctccacta | tttcggatag | tatttatggt | tctacctttt | 600 |
| tcttagcaac | tggctttcat | ggttttcatg | tgattatagg | tactcttttc | ttgatcgtat | 660 |
| gtggtattcg | ccaatatctt | ggtcatctga | ccaagaagca | tcacgttggc | tttgaagcag | 720 |
| ctgcatggta | ctggcatttt | gtagacgtgg | ttcggttatt | cccatttgtc | tctatctatt | 780 |
| ggtggggagg | tatatgaaag | aagggaacga | ataagtggat | tgaggaataa | aagctcgaag | 840 |
| acaaagagaa | cttctccggg | tactcaagat | attgtgtttg | gagaggtgta | gattgtagat | 900 |
| tccagccgag | ccagacccag | gaagaatacg | aagtccaatt | tcctcaacnn | ncaacgtaaa | 960 |
| aannnnnnna | aaaaaanggg | gaaaaaccga | acccnntttn | aaaaaaggcn | nnncnnnggg | 1020 |
| nggggnnngn | ggggcnccnn | ncnnnnc | | | | 1047 |

<210> SEQ ID NO 9
<211> LENGTH: 1028
<212> TYPE: DNA
<213> ORGANISM: Triticum zhukovskyi
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (924)..(925)
<223> OTHER INFORMATION: n is a, c, g, or t
<220> FEATURE:
<221> NAME/KEY: misc_feature
<222> LOCATION: (948)..(953)
<223> OTHER INFORMATION: n is a, c, g, or t
<220> FEATURE:
<221> NAME/KEY: misc_feature
<222> LOCATION: (961)..(969)

```
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t
<220> FEATURE:
<221> NAME/KEY: misc_feature
<222> LOCATION: (978)..(980)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (989)..(996)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t
<220> FEATURE:
<221> NAME/KEY: misc_feature
<222> LOCATION: (1006)..(1008)
<223> OTHER INFORMATION: n is a, c, g, or t
<220> FEATURE:
<221> NAME/KEY: misc_feature
<222> LOCATION: (1014)..(1015)
<223> OTHER INFORMATION: n is a, c, g, or t
<220> FEATURE:
<221> NAME/KEY: misc_feature
<222> LOCATION: (1018)..(1021)
<223> OTHER INFORMATION: n is a, c, g, or t
<220> FEATURE:
<221> NAME/KEY: misc_feature
<222> LOCATION: (1024)..(1027)
<223> OTHER INFORMATION: n is a, c, g, or t

<400> SEQUENCE: 9
nnnnnnnnnn nnnngaggca ttcttatcan ttggtagatc caagtccatg gcctatttcg      60
ggttcactcg gagctttggc aaccaccgta ggaggtgtga tgtacatgca ctcatttcaa     120
gggggtgcaa cacttctcag tttgggccta atatttatcc tttataccat gttcgtatgg     180
tggcgggatg ttctacgtga atccacgttg gaagggcatc atacaaaagc tgtacaatta     240
ggacctcgat atggttctat tctcttcata gtctcggagg ttatgttcct tttgctttt      300
ttttgggctt cttctcattc ttctttggca cctacggtag agatcggagg tatttggccc     360
ccaaaaggga ttggggtttt agatccttgg gaaatccctc ttcttaatac ccctattctc     420
ccttcatccg gagctgccgt aacttgggct catcatgcta tactcgcggg gaaggaaaaa     480
cgagcagttt acgctttagt agcaaccgtt tcactggctc tagtatccac tggctttcaa     540
ggaatggaat attaccaagc ccctccact atttcggata gtatttatgg ttctacctt      600
ttcttagcaa ctggctttca tggttttcat gtgattatag gtactctttt cttgatcgta     660
tgtggtattc gccaatatct tggtcatctg accaagaagc atcacgttgg ctttgaagca     720
gctgcatggt actggcattt tgtagacgtg gttcggttat cccatttgt ctctatctat      780
tggtggggag gtatatgaaa gaagggaacg aataagtgga ttgaggaata aaagctcgaa     840
gacaaagaga acttctccgg gtactcaaga tattgtgttt ggagaggtgt agattgtaga     900
ttccagccga gccagaccca ggannatacg aagtccattt cctcaacnnn nncgtagaa     960
nnnnnnnna aaangggnnn acngaancnn nnnnnnaaan ggccgnnnca tggnnggnnn    1020
nagnnnng                                                           1028
```

<210> SEQ ID NO 10
<211> LENGTH: 1046
<212> TYPE: DNA
<213> ORGANISM: Triticum timopheevii
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (955)..(960)
<223> OTHER INFORMATION: n is a, c, g, or t
<220> FEATURE:
<221> NAME/KEY: misc_feature
<222> LOCATION: (965)..(966)
<223> OTHER INFORMATION: n is a, c, g, or t
<220> FEATURE:
<221> NAME/KEY: misc_feature
<222> LOCATION: (968)..(973)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (999)..(1002)
<223> OTHER INFORMATION: n is a, c, g, or t
<220> FEATURE:
<221> NAME/KEY: misc_feature
<222> LOCATION: (1011)..(1015)
<223> OTHER INFORMATION: n is a, c, g, or t
<220> FEATURE:
<221> NAME/KEY: misc_feature
<222> LOCATION: (1017)..(1019)
<223> OTHER INFORMATION: n is a, c, g, or t
<220> FEATURE:
<221> NAME/KEY: misc_feature
<222> LOCATION: (1022)..(1023)
<223> OTHER INFORMATION: n is a, c, g, or t
<220> FEATURE:
<221> NAME/KEY: misc_feature
<222> LOCATION: (1027)..(1031)
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1036)..(1042)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t

<400> SEQUENCE: 10
nnnnnnnnnn nnnngnggca ttcttatcat tggtagatc caagtccatg gcctatttcg      60
ggttcactcg gagctttggc aaccaccgta ggaggtgtga tgtacatgca ctcatttcaa    120
gggggtgcaa cacttctcag tttgggccta atatttatcc tttataccat gttcgtatgg    180

| | |
|---|---|
| tggcgggatg ttctacgtga atccacgttg aagggcatc atacaaaagc tgtacaatta | 240 |
| ggacctcgat atggttctat tctcttcata gtctcggagg ttatgttcct ttttgctttt | 300 |
| ttttgggctt cttctcattc ttctttggca cctacggtag agatcggagg tatttggccc | 360 |
| ccaaaaggga ttggggtttt agatccttgg gaaatccctc ttcttaatac ccctattctc | 420 |
| ccttcatccg gagctgccgt aacttgggct catcatgcta tactcgcggg gaaggaaaaa | 480 |
| cgagcagttt acgctttagt agcaaccgtt tcactggctc tagtatccac tggcttcaa | 540 |
| ggaatggaat attaccaagc accctccact atttcggata gtatttatgg ttctaccttt | 600 |
| ttcttagcaa ctggctttca tggttttcat gtgattatag gtactctttt cttgatcgta | 660 |
| tgtggtattc gccaatatct tggtcatctg accaagaagc atcacgttgg ctttgaagca | 720 |
| gctgcatggt actggcattt tgtagacgtg gttcggttat tcccatttgt ctctatctat | 780 |
| tggtggggag gtatatgaaa aagggaacg aataagtgga ttgaggaata aaagctcgaa | 840 |
| gacaaagaga acttctccgg gtactcaaga tattgtgttt ggagaggtgt agattgtaga | 900 |
| ttccagccga gccagaccca ggaagaatac gaagtccaat ttcctcaacc gcgcnnnnnn | 960 |
| agaanngnnn nnnaaaaagg ggaanaacng gaaccnggnn ncaaaatgc nnnnncnnng | 1020 |
| gnngggnnnn nanggnnnnn nngngg | 1046 |

```
<210> SEQ ID NO 11
<211> LENGTH: 622
<212> TYPE: DNA
<213> ORGANISM: Triticum aestivum
<220> FEATURE:
<221> NAME/KEY: misc_feature
<222> LOCATION: (1)..(21)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
```

-continued

```
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (96)..(97)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (210)..(211)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (236)..(241)
<223> OTHER INFORMATION: n is a, c, g, or t
<220> FEATURE:
<221> NAME/KEY: misc_feature
<222> LOCATION: (243)..(245)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (260)..(264)
<223> OTHER INFORMATION: n is a, c, g, or t
<220> FEATURE:
<221> NAME/KEY: misc_feature
<222> LOCATION: (271)..(273)
<223> OTHER INFORMATION: n is a, c, g, or t
<220> FEATURE:
<221> NAME/KEY: misc_feature
<222> LOCATION: (276)..(280)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (286)..(288)
<223> OTHER INFORMATION: n is a, c, g, or t
<220> FEATURE:
<221> NAME/KEY: misc_feature
<222> LOCATION: (292)..(295)
```

```
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (307)..(308)
<223> OTHER INFORMATION: n is a, c, g, or t
<220> FEATURE:
<221> NAME/KEY: misc_feature
<222> LOCATION: (311)..(312)
<223> OTHER INFORMATION: n is a, c, g, or t
<220> FEATURE:
<221> NAME/KEY: misc_feature
<222> LOCATION: (314)..(315)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (321)..(324)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (330)..(333)
<223> OTHER INFORMATION: n is a, c, g, or t
<220> FEATURE:
<221> NAME/KEY: misc_feature
<222> LOCATION: (336)..(337)
<223> OTHER INFORMATION: n is a, c, g, or t
<220> FEATURE:
<221> NAME/KEY: misc_feature
<222> LOCATION: (339)..(347)
<223> OTHER INFORMATION: n is a, c, g, or t
<220> FEATURE:
<221> NAME/KEY: misc_feature
<222> LOCATION: (351)..(353)
<223> OTHER INFORMATION: n is a, c, g, or t
<220> FEATURE:
<221> NAME/KEY: misc_feature
<222> LOCATION: (355)..(356)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (362)..(364)
<223> OTHER INFORMATION: n is a, c, g, or t
<220> FEATURE:
<221> NAME/KEY: misc_feature
<222> LOCATION: (367)..(370)
<223> OTHER INFORMATION: n is a, c, g, or t
<220> FEATURE:
<221> NAME/KEY: misc_feature
<222> LOCATION: (373)..(375)
<223> OTHER INFORMATION: n is a, c, g, or t
<220> FEATURE:
<221> NAME/KEY: misc_feature
<222> LOCATION: (380)..(381)
<223> OTHER INFORMATION: n is a, c, g, or t
<220> FEATURE:
<221> NAME/KEY: misc_feature
<222> LOCATION: (385)..(393)
<223> OTHER INFORMATION: n is a, c, g, or t
<220> FEATURE:
<221> NAME/KEY: misc_feature
```

```
<222> LOCATION: (397)..(398)
<223> OTHER INFORMATION: n is a, c, g, or t
<220> FEATURE:
<221> NAME/KEY: misc_feature
<222> LOCATION: (400)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (415)..(417)
<223> OTHER INFORMATION: n is a, c, g, or t
<220> FEATURE:
<221> NAME/KEY: misc_feature
<222> LOCATION: (421)..(438)
<223> OTHER INFORMATION: n is a, c, g, or t
<220> FEATURE:
<221> NAME/KEY: misc_feature
<222> LOCATION: (440)..(450)
<223> OTHER INFORMATION: n is a, c, g, or t
<220> FEATURE:
<221> NAME/KEY: misc_feature
<222> LOCATION: (452)..(455)
<223> OTHER INFORMATION: n is a, c, g, or t
<220> FEATURE:
<221> NAME/KEY: misc_feature
<222> LOCATION: (458)..(461)
<223> OTHER INFORMATION: n is a, c, g, or t
<220> FEATURE:
<221> NAME/KEY: misc_feature
<222> LOCATION: (463)..(472)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (477)..(500)
<223> OTHER INFORMATION: n is a, c, g, or t
<220> FEATURE:
<221> NAME/KEY: misc_feature
<222> LOCATION: (503)..(509)
<223> OTHER INFORMATION: n is a, c, g, or t
<220> FEATURE:
<221> NAME/KEY: misc_feature
<222> LOCATION: (511)..(518)
<223> OTHER INFORMATION: n is a, c, g, or t
<220> FEATURE:
<221> NAME/KEY: misc_feature
<222> LOCATION: (520)..(535)
<223> OTHER INFORMATION: n is a, c, g, or t
<220> FEATURE:
<221> NAME/KEY: misc_feature
<222> LOCATION: (537)..(559)
<223> OTHER INFORMATION: n is a, c, g, or t
<220> FEATURE:
<221> NAME/KEY: misc_feature
<222> LOCATION: (561)..(563)
<223> OTHER INFORMATION: n is a, c, g, or t
<220> FEATURE:
<221> NAME/KEY: misc_feature
<222> LOCATION: (565)..(597)
<223> OTHER INFORMATION: n is a, c, g, or t
<220> FEATURE:
<221> NAME/KEY: misc_feature
<222> LOCATION: (599)..(609)
<223> OTHER INFORMATION: n is a, c, g, or t
<220> FEATURE:
<221> NAME/KEY: misc_feature
<222> LOCATION: (611)..(622)
<223> OTHER INFORMATION: n is a, c, g, or t

<400> SEQUENCE: 11
nnnnnnnnnn nnnnnnnnnn nannncattn ngnagatcca agnccanggc cnntttcggg    60
```

```
ttcactcggn ncttnggcna ccaccgtagg nggngnnatg tacatgcact catttcaagg        120
gggngcaaca nttctcagtt ngggccctaa tatttatcct ttataccatg ttcgtatngn        180
tggcggggat gttnnacgng aatccacgtn nggangggc atcatacaaa agctgnnnnn         240
ntnnnggacc tcgatatngn nnnnatttct nnncannnnn ctcgnnngg tnnnntncct         300 tttttgnntt nntnngncnt nnnnctcntn nnnctnngnn nnnnnnnggt nnnannatcn        360
gnnnggnnnn ttnnnccccn naaannnnnn nnnggnntn nnnnnnnncc ntggnnaaa         420 nnnnnnnnnn nnnnnnnncn nnnnnnnnnn tnnnnccnnn ngnnnnnnnn nnttngnnnn        480
nnnnnnnnnn nnnnnnnnnn ggnnnnnnna nnnnnnnntn nnnnnnnnnn nnnnncnnnn        540
nnnnnnnnnn nnnnnnnng nnntnnnnnn nnnnnnnnnn nnnnnnnnnn nnnnnngnn        600 nnnnnnnng nnnnnnnnnn nn                                                  622
```

```
<210> SEQ ID NO 12
<211> LENGTH: 1022
<212> TYPE: DNA
<213> ORGANISM: x Triticosecale
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(16)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (951)..(953)
<223> OTHER INFORMATION: n is a, c, g, or t
<220> FEATURE:
<221> NAME/KEY: misc_feature
<222> LOCATION: (960)..(971)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t
<220> FEATURE:
<221> NAME/KEY: misc_feature
<222> LOCATION: (990)..(995)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1004)..(1012)
<223> OTHER INFORMATION: n is a, c, g, or t
<220> FEATURE:
<221> NAME/KEY: misc_feature
<222> LOCATION: (1015)..(1019)
<223> OTHER INFORMATION: n is a, c, g, or t

<400> SEQUENCE: 12
nnnnnnnnna nnnnnnggca ttcttatcan ttggtagatc caagtccatg gcctatttcg        60
ggttcactcg gagctttggc aaccaccgta ggaggtgtga tgtacatgca ctcatttcaa       120
gggggtgcaa cacttctcag tttgggccta atatttatcc tttataccat gttcgtatgg       180
tggcgggatg ttctacgtga atccacgttg gaagggcatc atacaaaagc tgtacaatta      240
ggacctcgat atggttctat tctcttcata gtctcggagg ttatgttcct ttttgctttt      300 tttttgggctt cttctcattc ttctttggca cctacggtag agatcggagg tatttggccc     360
```

```
ccaaaaggga ttggggtttt agatccttgg gaaatccctc ttcttaatac ccctattctc    420
ccttcatccg gagctgccgt aacttgggct catcatgcta tactcgcggg gaaggaaaaa    480
cgagcagttt acgctttagt agcaaccgtt tcactggctc tagtatccac tggcttttcaa   540 ggaatggaat attaccaagc accctccact atttcggata gtatttatgg ttctacctttt   600 ttcttagcaa ctggctttca tggttttcat gtgattatag gtactctttt cttgatcgta    660
tgtggtattc gccaatatct tggtcagatg accaagaagc atcacgttgg ctttgaagca    720
gctgcatggt actggcattt tgtagacgtg gttcggttat cccatttgt ctctatctat     780 tggtggggag gtatatgaaa gaagggaacg aataagtgga ttgaggaata aaagctcgaa    840
gacaaagaga acttctccgg gtactcaaga tattgtgttt ggagaggtgt agattgtaga    900
ttccagccga gccagaccca ggaagaatac gaagtccatt tcctcaacgc nnnacgatan    960
nnnnnnnnnn naaaggggaa aaccngaacn nnnnacnaa aggnnnnnnn nnggnnnnnt    1020
tt                                                                  1022

<210> SEQ ID NO 13
<211> LENGTH: 1017
<212> TYPE: DNA
<213> ORGANISM: x Triticosecale
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (950)..(956)
<223> OTHER INFORMATION: n is a, c, g, or t
<220> FEATURE:
<221> NAME/KEY: misc_feature
<222> LOCATION: (964)..(966)
<223> OTHER INFORMATION: n is a, c, g, or t
<220> FEATURE:
<221> NAME/KEY: misc_feature
<222> LOCATION: (968)..(970)
<223> OTHER INFORMATION: n is a, c, g, or t
<220> FEATURE:
<221> NAME/KEY: misc_feature
<222> LOCATION: (972)..(973)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t
<220> FEATURE:
<221> NAME/KEY: misc_feature
<222> LOCATION: (990)..(999)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
```

<221> NAME/KEY: misc_feature
<222> LOCATION: (1005)..(1013)
<223> OTHER INFORMATION: n is a, c, g, or t

<400> SEQUENCE: 13

```
nnnnnnnnnn nncngnngca ttcttancan ttggtagatc caagtccatg gcctatttcg      60
ggttcactcg gagctttggc aaccaccgta ggaggtgtga tgtacatgca ctcatttcaa     120
gggggtgcaa cacttctcag tttgggccta atatttatcc tttataccat gttcgtatgg     180
tggcgggatg ttctacgtga atccacgttg gaagggcatc atacaaaagc tgtacaatta     240
ggacctcgat atggttctat tctcttcata gtctcggagg ttatgttcct ttttgctttt     300
ttttgggctt cttctcattc ttctttggca cctacggtag agatcggagg tatttggccc     360
ccaaaaggga ttggggtttt agatccttgg gaaatccctc ttcttaatac ccctattctc     420
ccttcatccg gagctgccgt aacttgggct catcatgcta tactcgcggg gaaggaaaaa     480
cgagcagttt acgctttagt agcaaccgtt tcactggctc tagtatccac tggctttcaa     540
ggaatggaat attaccaagc accctccact atttcggata gtatttatgg ttctaccttt     600
ttcttagcaa ctggctttca tggttttcat gtgattatag gtactctttt cttgatcgta     660
tgtggtattc gccaatatct tggtcagatg accaagaagc atcacgttgg ctttgaagca     720
gctgcatggt actggcattt tgtagacgtg gttcggttat tcccatttgt ctctatctat     780
tggtggggag gtatatgaaa gaagggaacg aataagtgga ttgaggaata aaagctcgaa     840
gacaaagaga acttctccgg gtactcaaga tattgtgttt ggagaggtgt agattgtaga     900
ttccagccga gccagaccca ggaagaatac gaagtccaat ttcctcaacn nnnnnncgat     960
aganngnnn annaaagggg aaaancgaan nnnnnnnna anggnnnnnn nngggg        1017
```

<210> SEQ ID NO 14
<211> LENGTH: 576
<212> TYPE: DNA
<213> ORGANISM: x Triticosecale
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (203)..(204)
<223> OTHER INFORMATION: n is a, c, g, or t
<220> FEATURE:
<221> NAME/KEY: misc_feature

```
<222> LOCATION: (206)..(206)
<223> OTHER INFORMATION: n is a, c, g, or t
<220> FEATURE:
<221> NAME/KEY: misc_feature
<222> LOCATION: (208)..(209)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (231)..(232)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (254)..(256)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (277)..(282)
<223> OTHER INFORMATION: n is a, c, g, or t
<220> FEATURE:
<221> NAME/KEY: misc_feature
<222> LOCATION: (284)..(285)
<223> OTHER INFORMATION: n is a, c, g, or t
<220> FEATURE:
<221> NAME/KEY: misc_feature
<222> LOCATION: (291)..(294)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
```

```
<221> NAME/KEY: misc_feature
<222> LOCATION: (339)..(340)
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (367)..(368)
<223> OTHER INFORMATION: n is a, c, g, or t
<220> FEATURE:
<221> NAME/KEY: misc_feature
<222> LOCATION: (372)..(374)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (404)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (416)..(417)
<223> OTHER INFORMATION: n is a, c, g, or t
<220> FEATURE:
<221> NAME/KEY: misc_feature
<222> LOCATION: (419)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(427)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
```

<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (484)..(484)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (504)..(505)
<223> OTHER INFORMATION: n is a, c, g, or t
<220> FEATURE:
<221> NAME/KEY: misc_feature
<222> LOCATION: (507)..(508)
<223> OTHER INFORMATION: n is a, c, g, or t
<220> FEATURE:
<221> NAME/KEY: misc_feature
<222> LOCATION: (513)..(515)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (545)..(546)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t

<400> SEQUENCE: 14

```
nnnnnnnnna ntnctaccgn nnngtcaaga cgaaaacgtg tgccaacccc tatgcataag      60
ttcattgaac ccgcaagttg atcaccaaaa catacatcaa gtagatcacg tgaatatccc     120
attgtcacca cggataagac gcgagacaat gggatattcn cgtgatctac ttgatgtatg     180
ttttggtgat caacttgngn nannantnng gtangggggg gagcctncng nngnntntcg     240
```

```
gtgaacatgg gngnnnattn gnnntttgnc nggtgannnn nncnntagga nnnntgaatt    300
ttccttnctt tttgaanctt ggaatanaga agatcttcnn tccnnanaag ggttactgtt    360
anagatnnat gnnnaantcc ttttctaaag acccttattg gccnncgngc tttggnngnn    420
tanttnngtc atcntgccnt ntccggggga tggnaaanga tctgtttanc cntngtataa    480
ctgntntntt ggctctgnaa tncnngnntt tannnaatgn anaacnaccc agcnccttc     540 acttnntntg atantatntc tggtcccctt atttct                             576
```

```
<210> SEQ ID NO 15
<211> LENGTH: 1043
<212> TYPE: DNA
<213> ORGANISM: x Triticosecale
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (950)..(950)
<223> OTHER INFORMATION: n is a, c, g, or t
<220> FEATURE:
<221> NAME/KEY: misc_feature
<222> LOCATION: (952)..(953)
<223> OTHER INFORMATION: n is a, c, g, or t
<220> FEATURE:
<221> NAME/KEY: misc_feature
<222> LOCATION: (963)..(970)
<223> OTHER INFORMATION: n is a, c, g, or t
<220> FEATURE:
<221> NAME/KEY: misc_feature
<222> LOCATION: (987)..(988)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (994)..(995)
<223> OTHER INFORMATION: n is a, c, g, or t
<220> FEATURE:
<221> NAME/KEY: misc_feature
<222> LOCATION: (998)..(1000)
<223> OTHER INFORMATION: n is a, c, g, or t
<220> FEATURE:
<221> NAME/KEY: misc_feature
<222> LOCATION: (1011)..(1014)
<223> OTHER INFORMATION: n is a, c, g, or t
<220> FEATURE:
<221> NAME/KEY: misc_feature
<222> LOCATION: (1016)..(1017)
<223> OTHER INFORMATION: n is a, c, g, or t
<220> FEATURE:
<221> NAME/KEY: misc_feature
<222> LOCATION: (1019)..(1021)
<223> OTHER INFORMATION: n is a, c, g, or t
<220> FEATURE:
<221> NAME/KEY: misc_feature
<222> LOCATION: (1026)..(1040)
<223> OTHER INFORMATION: n is a, c, g, or t

<400> SEQUENCE: 15
nnnnnnnnnn nnnngannca ttcttatcat ttggtagatc caagtccatg gcctatttcg     60
ggttcactcg gagctttggc aaccaccgta ggaggtgtga tgtacatgca ctcatttcaa    120
gggggtgcaa cacttctcag tttgggccta atatttatcc tttataccat gttcgtatgg    180
tggcgggatg ttctacgtga atccacgttg gaagggcatc atacaaaagc tgtacaatta    240
```

```
ggacctcgat atggttctat tctcttcata gtctcggagg ttatgttcct ttttgctttt      300
ttttgggctt cttctcattc ttctttggca cctacggtag agatcggagg tatttggccc      360
ccaaaaggga ttggggtttt agatccttgg gaaatccctc ttcttaatac ccctattctc      420
ccttcatccg gagctgccgt aacttgggct catcatgcta tactcgcggg gaaggaaaaa      480
cgagcagttt acgctttagt agcaaccgtt tcactggctc tagtatccac tggctttcaa      540
ggaatggaat attaccaagc accctccact atttcggata gtatttatgg ttctacctttt     600 ttcttagcaa ctggctttca tggttttcat gtgattatag gtactctttt cttgatcgta      660
tgtggtattc gccaatatct tggtcagatg accaagaagc atcacgttgg ctttgaagca      720
gctgcatggt actggcattt tgtagacgtg gttcggttat tcccatttgt ctctatctat      780
tggtggggag gtatatgaaa gaagggaacg aataagtgga ttgaggaata aaagctcgaa      840
gacaaagaga acttctccgg gtactcaaga tattgtgttt ggagaggtgt agattgtaga      900
ttccagccga gccagaccca ggaagaatac gaagtccaat ttcctcaacn cnnaacgtag      960
aannnnnnnn gaaaaagggg aaacccnnan cccnngcnnn aaaaaggccg nnnnanngnn     1020 ngggggnnnnn nnnnnnnnnn aaa                                            1043

<210> SEQ ID NO 16
<211> LENGTH: 1011
<212> TYPE: DNA
<213> ORGANISM: x Triticosecale
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (217)..(222)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (230)..(231)
<223> OTHER INFORMATION: n is a, c, g, or t
<220> FEATURE:
<221> NAME/KEY: misc_feature
<222> LOCATION: (338)..(339)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
```

-continued

```
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (684)..(685)
<223> OTHER INFORMATION: n is a, c, g, or t
<220> FEATURE:
<221> NAME/KEY: misc_feature
<222> LOCATION: (717)..(718)
<223> OTHER INFORMATION: n is a, c, g, or t
<220> FEATURE:
<221> NAME/KEY: misc_feature
<222> LOCATION: (774)..(775)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (791)..(792)
<223> OTHER INFORMATION: n is a, c, g, or t
<220> FEATURE:
<221> NAME/KEY: misc_feature
<222> LOCATION: (807)..(808)
<223> OTHER INFORMATION: n is a, c, g, or t
<220> FEATURE:
<221> NAME/KEY: misc_feature
<222> LOCATION: (827)..(828)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (841)..(842)
<223> OTHER INFORMATION: n is a, c, g, or t
<220> FEATURE:
<221> NAME/KEY: misc_feature
<222> LOCATION: (845)..(848)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (869)..(870)
<223> OTHER INFORMATION: n is a, c, g, or t
<220> FEATURE:
<221> NAME/KEY: misc_feature
<222> LOCATION: (873)..(874)
<223> OTHER INFORMATION: n is a, c, g, or t
<220> FEATURE:
<221> NAME/KEY: misc_feature
<222> LOCATION: (881)..(884)
<223> OTHER INFORMATION: n is a, c, g, or t
<220> FEATURE:
<221> NAME/KEY: misc_feature
<222> LOCATION: (887)..(889)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
```

```
<220> FEATURE:
<221> NAME/KEY: misc_feature
<222> LOCATION: (913)..(914)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (926)..(928)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t
<220> FEATURE:
<221> NAME/KEY: misc_feature
<222> LOCATION: (950)..(953)
<223> OTHER INFORMATION: n is a, c, g, or t
<220> FEATURE:
<221> NAME/KEY: misc_feature
<222> LOCATION: (955)..(955)
<223> OTHER INFORMATION: n is a, c, g, or t
<220> FEATURE:
<221> NAME/KEY: misc_feature
<222> LOCATION: (964)..(969)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t
<220> FEATURE:
<221> NAME/KEY: misc_feature
<222> LOCATION: (988)..(988)
<223> OTHER INFORMATION: n is a, c, g, or t
<220> FEATURE:
<221> NAME/KEY: misc_feature
<222> LOCATION: (997)..(998)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t
<220> FEATURE:
<221> NAME/KEY: misc_feature
<222> LOCATION: (1002)..(1004)
<223> OTHER INFORMATION: n is a, c, g, or t
<220> FEATURE:
<221> NAME/KEY: misc_feature
<222> LOCATION: (1008)..(1009)
<223> OTHER INFORMATION: n is a, c, g, or t

<400> SEQUENCE: 16
nnnnnnnnnn nnnaggcntt cttatcantt ggtagntcca agtccatggc ctatttcggg      60
ttcactcgga gctttggcaa ccaccgtagg aggtgtgatg tacatgcact catttcaagg     120
gggtgcaaca cttctcagtt tgggcctaat atttatcctt tataccatgt tcgtatggtg     180
gcgggatgtt ctacgtgaat ccacgttgga agggcannnn nnaaangctn nacaattagg     240
acctcgatat ggttctattc tcttcatagt ctcggaggtt atgttccttt ttgctttttt     300
tgggcttctt ctcattcttc tttggcacct acggtagnna tcggaggtat ttggccccca     360
aaagggattg gggttttana tccttgggaa atccctnttc ttaataccccc tattctccct     420 tcatccggag ctgccgtaac ttgggctcat catgctatac tcncggggaa ggaaaaacga     480
```

```
gcagtttacg ctttagtagc aaccgtttca ctggctctag tatccactgg ctttcaagga      540
atggaatatt accaagcacc ctccactatt tcgganagta tttatggttc tacctttttc      600
ttagcaactg gctttcatgg ttttcatgtg attataggta ctcttttctt gatcgtatgt      660
ggtattcgcc aatntcttgg tcanntgacc aagaagcatc acgttggctt tgaagcnnct      720
gcatggtact ggcattttgt agacgtggtt cggttattcc catttgtctc tatnnattgg      780 nggggaggt nnatgaaaga agggaannaa taagtggatt gaggaannaa agctcgaana      840
nnaannnnan tncnccgggt actcaagann ttnngtttgg nnnnggnnna gattgtagat      900
tccagccnag ccnnacccag gaanannncg aagtcnaatt tccncaaccn nnnancggaa      960
aaannnnnna aaaaaaangg ggaanaancc gaacccnngn cnnnaaanng g              1011
```

<210> SEQ ID NO 17
<211> LENGTH: 870
<212> TYPE: DNA
<213> ORGANISM: Aegilops sharonensis
<220> FEATURE:
<221> NAME/KEY: misc_feature
<222> LOCATION: (1)..(26)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (555)..(558)
<223> OTHER INFORMATION: n is a, c, g, or t
<220> FEATURE:
<221> NAME/KEY: misc_feature
<222> LOCATION: (590)..(592)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (610)..(611)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t

```
<220> FEATURE:
<221> NAME/KEY: misc_feature
<222> LOCATION: (664)..(665)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (741)..(744)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (782)..(786)
<223> OTHER INFORMATION: n is a, c, g, or t
<220> FEATURE:
<221> NAME/KEY: misc_feature
<222> LOCATION: (789)..(791)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (795)..(795)
```

<223> OTHER INFORMATION: n is a, c, g, or t
<220> FEATURE:
<221> NAME/KEY: misc_feature
<222> LOCATION: (798)..(814)
<223> OTHER INFORMATION: n is a, c, g, or t
<220> FEATURE:
<221> NAME/KEY: misc_feature
<222> LOCATION: (816)..(826)
<223> OTHER INFORMATION: n is a, c, g, or t
<220> FEATURE:
<221> NAME/KEY: misc_feature
<222> LOCATION: (828)..(831)
<223> OTHER INFORMATION: n is a, c, g, or t
<220> FEATURE:
<221> NAME/KEY: misc_feature
<222> LOCATION: (833)..(839)
<223> OTHER INFORMATION: n is a, c, g, or t
<220> FEATURE:
<221> NAME/KEY: misc_feature
<222> LOCATION: (842)..(843)
<223> OTHER INFORMATION: n is a, c, g, or t
<220> FEATURE:
<221> NAME/KEY: misc_feature
<222> LOCATION: (845)..(857)
<223> OTHER INFORMATION: n is a, c, g, or t
<220> FEATURE:
<221> NAME/KEY: misc_feature
<222> LOCATION: (859)..(864)
<223> OTHER INFORMATION: n is a, c, g, or t
<220> FEATURE:
<221> NAME/KEY: misc_feature
<222> LOCATION: (866)..(870)
<223> OTHER INFORMATION: n is a, c, g, or t

<400> SEQUENCE: 17

| | | | | | |
|---|---|---|---|---|---|
| nnnnnnnnnn | nnnnnnnnnn | nnnnnngagt | cttcctctng | atgctttcga | acgactccta | 60 |
| aatttcacaa | aatcctttt | ttcttatttg | aaatccaaat | caaaatgcct | caacttgata | 120 |
| aattaactta | tttctcacaa | ttcttctggt | tatgtcttct | cctctttact | ttttatattc | 180 |
| tcttatttaa | taataataat | ggaatacttg | gaattagtag | aattctcaaa | ctacggaacc | 240 |
| aactgctttc | gcaccggggg | ggggagatcc | ggagcaagga | ccctaagaat | ctggaagata | 300 |
| tctcgagaaa | aggttttagc | accggtctct | catatatgta | ctccagttta | tccgaagtat | 360 |
| cccaatggtg | taagaccgtc | gcctatttgg | gataaaggag | gaaaatcact | ctgatctctg | 420 |
| atttcagaga | aataagaggc | tcacgaggaa | tggagagaca | gattctctat | ttgatctcga | 480 |
| agtcctcata | taanacttct | tccagtcgga | tcacttgttg | gaaaaanata | ntgctcacac | 540 |
| atgttccncn | cgggnnnnng | aagcaaaata | tcatgaaagc | cgtctgatan | nntttntntn | 600 |
| ggttccccgn | ngagaatgga | aaaatcacaa | aaacactttc | tntatgttct | gttatttcga | 660 |
| gatnngaana | agnaagcaag | ttttttcata | tagctgtttn | cctgtgtngn | gatcgctgtt | 720 |
| cgngnagatc | atnaggcccc | nnnnataccc | ctntngntac | ggggggggng | naaaaaangg | 780 |
| gnnnnnggnn | ntntntcnnn | nnnnnnnnnn | nnnncnnnnn | nnnnnngnnn | ntnnnnnnnc | 840 |
| cnncnnnnnn | nnnnnnngnn | nnnngnnnnn | | | | 870 |

<210> SEQ ID NO 18
<211> LENGTH: 872
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t -continued

```
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (527)..(529)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (562)..(563)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (631)..(632)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (711)..(711)
```

-continued

```
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (723)..(724)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (748)..(749)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (757)..(758)
<223> OTHER INFORMATION: n is a, c, g, or t
<220> FEATURE:
<221> NAME/KEY: misc_feature
<222> LOCATION: (761)..(763)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t
<220> FEATURE:
<221> NAME/KEY: misc_feature
<222> LOCATION: (770)..(772)
<223> OTHER INFORMATION: n is a, c, g, or t
<220> FEATURE:
<221> NAME/KEY: misc_feature
<222> LOCATION: (774)..(775)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (783)..(784)
<223> OTHER INFORMATION: n is a, c, g, or t
<220> FEATURE:
<221> NAME/KEY: misc_feature
<222> LOCATION: (791)..(807)
<223> OTHER INFORMATION: n is a, c, g, or t
<220> FEATURE:
<221> NAME/KEY: misc_feature
<222> LOCATION: (809)..(810)
<223> OTHER INFORMATION: n is a, c, g, or t
<220> FEATURE:
<221> NAME/KEY: misc_feature
<222> LOCATION: (812)..(818)
<223> OTHER INFORMATION: n is a, c, g, or t
<220> FEATURE:
<221> NAME/KEY: misc_feature
<222> LOCATION: (821)..(821)
<223> OTHER INFORMATION: n is a, c, g, or t
<220> FEATURE:
<221> NAME/KEY: misc_feature
<222> LOCATION: (823)..(824)
<223> OTHER INFORMATION: n is a, c, g, or t
<220> FEATURE:
<221> NAME/KEY: misc_feature
<222> LOCATION: (827)..(829)
<223> OTHER INFORMATION: n is a, c, g, or t
<220> FEATURE:
<221> NAME/KEY: misc_feature
```

<222> LOCATION: (831)..(842)
<223> OTHER INFORMATION: n is a, c, g, or t
<220> FEATURE:
<221> NAME/KEY: misc_feature
<222> LOCATION: (844)..(852)
<223> OTHER INFORMATION: n is a, c, g, or t
<220> FEATURE:
<221> NAME/KEY: misc_feature
<222> LOCATION: (855)..(856)
<223> OTHER INFORMATION: n is a, c, g, or t
<220> FEATURE:
<221> NAME/KEY: misc_feature
<222> LOCATION: (858)..(864)
<223> OTHER INFORMATION: n is a, c, g, or t
<220> FEATURE:
<221> NAME/KEY: misc_feature
<222> LOCATION: (866)..(872)
<223> OTHER INFORMATION: n is a, c, g, or t

<400> SEQUENCE: 18

```
nnnnnnnnnn ntcttntgag tncttcnnct tgatgctttc gaacgactcc taaatttcac      60
aaaatccttt ttttcttatt tgaaatccaa atcgaaatgc ctcaacttga taaattaact     120
tatttctcac aattcttctg gttatgtctt ctcctcttta cttttatat tctcttattt      180
aataataata atggaatact tggaattagt agaattctca aactacgaa ccaactgctt      240
tcgcaccggg ggggggggg ggggagcaag accctaaga aactggaaga tctctcgaga      300
aaaggttttt gcaccggtct ctcctatatg tactccagtt tatccgaagt atcccaatgg    360
tgtaagaccg tcgactattt tggataaagg aggaaaaaaa ctctaatctc ttctttcata    420
gaaataagag gctcacaagg aatggagaga aagantctct atttgatctc gaagtcctca    480
tataacactt cttccanccg gatcacttgt tggaaaaana naaanannnc acatgttccn    540
cacgggccag gangggnaaa annatgaaag ccgtcngata atctttntnt attttccccc    600
gaggagaatg gaaaaaaaaa caaaaaacac nntctatatg tttctgttat tttcgagatt    660
cgnanaaaca agcaaagntt ttcatataga ttgtttcctg tgtagtgatc nctgttcntg    720
gannatcatg agncnccctg aaaccccnnt gntaccnngg nnnaanaagn nngnnangag    780
ggnntctttt nnnnnnnnnn nnnnnnnann annnnnnnca ngnntcnnnt nnnnnnnnnn    840
nncnnnnnnn nnaannannn nnnnannnnn nn                                  872
```

<210> SEQ ID NO 19
<211> LENGTH: 882
<212> TYPE: DNA
<213> ORGANISM: Aegilops sharonensis
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (31)..(33)
<223> OTHER INFORMATION: n is a, c, g, or t
<220> FEATURE:
<221> NAME/KEY: misc_feature
<222> LOCATION: (46)..(46)

```
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (497)..(498)
<223> OTHER INFORMATION: n is a, c, g, or t
<220> FEATURE:
<221> NAME/KEY: misc_feature
<222> LOCATION: (524)..(524)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (540)..(541)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (554)..(555)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(562)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (590)..(591)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
```

```
<222> LOCATION: (630)..(635)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (697)..(698)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (705)..(706)
<223> OTHER INFORMATION: n is a, c, g, or t
<220> FEATURE:
<221> NAME/KEY: misc_feature
<222> LOCATION: (708)..(709)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (725)..(726)
<223> OTHER INFORMATION: n is a, c, g, or t
<220> FEATURE:
<221> NAME/KEY: misc_feature
<222> LOCATION: (732)..(734)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
```

-continued

```
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (768)..(769)
<223> OTHER INFORMATION: n is a, c, g, or t
<220> FEATURE:
<221> NAME/KEY: misc_feature
<222> LOCATION: (780)..(781)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (788)..(790)
<223> OTHER INFORMATION: n is a, c, g, or t
<220> FEATURE:
<221> NAME/KEY: misc_feature
<222> LOCATION: (793)..(794)
<223> OTHER INFORMATION: n is a, c, g, or t
<220> FEATURE:
<221> NAME/KEY: misc_feature
<222> LOCATION: (796)..(811)
<223> OTHER INFORMATION: n is a, c, g, or t
<220> FEATURE:
<221> NAME/KEY: misc_feature
<222> LOCATION: (813)..(815)
<223> OTHER INFORMATION: n is a, c, g, or t
<220> FEATURE:
<221> NAME/KEY: misc_feature
<222> LOCATION: (817)..(817)
<223> OTHER INFORMATION: n is a, c, g, or t
<220> FEATURE:
<221> NAME/KEY: misc_feature
<222> LOCATION: (821)..(824)
<223> OTHER INFORMATION: n is a, c, g, or t
<220> FEATURE:
<221> NAME/KEY: misc_feature
<222> LOCATION: (826)..(831)
<223> OTHER INFORMATION: n is a, c, g, or t
<220> FEATURE:
<221> NAME/KEY: misc_feature
<222> LOCATION: (833)..(833)
<223> OTHER INFORMATION: n is a, c, g, or t
<220> FEATURE:
<221> NAME/KEY: misc_feature
<222> LOCATION: (835)..(838)
<223> OTHER INFORMATION: n is a, c, g, or t
<220> FEATURE:
<221> NAME/KEY: misc_feature
<222> LOCATION: (840)..(843)
<223> OTHER INFORMATION: n is a, c, g, or t
<220> FEATURE:
<221> NAME/KEY: misc_feature
<222> LOCATION: (846)..(848)
<223> OTHER INFORMATION: n is a, c, g, or t
<220> FEATURE:
<221> NAME/KEY: misc_feature
<222> LOCATION: (850)..(851)
<223> OTHER INFORMATION: n is a, c, g, or t
<220> FEATURE:
<221> NAME/KEY: misc_feature
<222> LOCATION: (854)..(864)
<223> OTHER INFORMATION: n is a, c, g, or t
<220> FEATURE:
<221> NAME/KEY: misc_feature
<222> LOCATION: (866)..(869)
<223> OTHER INFORMATION: n is a, c, g, or t
```

-continued

<220> FEATURE:
<221> NAME/KEY: misc_feature
<222> LOCATION: (871)..(882)
<223> OTHER INFORMATION: n is a, c, g, or t

<400> SEQUENCE: 19

```
nnnnnnnnnn nnnnnnntnt tctgngnctt nnncttgatg ctttcnacga ctccaatttc      60
caaaatcctt tttttcttat ttgaaatcca aatcgaaatg cctcaacttg ataaattaac     120
ttatttctca caattcttct ggttatgtct tctcctcttt acttttata ttctcttatt     180
taataataat aatggaatac ttggaattag tagaattctc aaactacgga accaactgct     240
ttcgcaccgg ggggggaga tccggagcaa ggacccaag aatctggaag atatctcgcg      300
aaaggtttt agcaccggtc tctcctatat gtactccact ttatccgaag tatcccaatg      360
gtgtgagacc gccgcctatt tgggataaag aaggaaaatc actctgatct ctgatttcag     420
agaaataaga ggctcacgag gaaaggagag acagattctc tntttgatct cgaagtcctc     480
ttataanact tcttccnncc ggatcacttg ttggaaaaaa aaantgntct cacatgttcn     540
ncacggggng aggnngnana nnatcatgaa agccgcctga tanatctttn ntntngnttc     600
cccccngaga angggaanaa tcacaaaaan nnnnnctnta tgttcgngtt ntttcgagat     660
gcgaagaagn aangcaagnt ttttcatata nctgttnncn tgngnngnna tcnctgttcg     720
ggggnnatca tnnnggcccc cncnanaccc ntcnggtang gggggggnna aaaaagggn     780
ntntgngnnn tcnntnnnnn nnnnnnnnnn nannnanggc nnnngnnnnn ngntnnnntn     840
nnnccnnncn nccnnnnnnn nnnnannnng nnnnnnnnnn nn                       882
```

<210> SEQ ID NO 20
<211> LENGTH: 816
<212> TYPE: DNA
<213> ORGANISM: Aegilops sharonensis
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (265)..(269)
<223> OTHER INFORMATION: n is a, c, g, or t
<220> FEATURE:
<221> NAME/KEY: misc_feature
<222> LOCATION: (271)..(278)
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (284)..(286)
<223> OTHER INFORMATION: n is a, c, g, or t
<220> FEATURE:

```
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (304)..(304)
<223> OTHER INFORMATION: n is a, c, g, or t
<220> FEATURE:
<221> NAME/KEY: misc_feature
<222> LOCATION: (306)..(310)
<223> OTHER INFORMATION: n is a, c, g, or t
<220> FEATURE:
<221> NAME/KEY: misc_feature
<222> LOCATION: (312)..(317)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (329)..(332)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (347)..(348)
<223> OTHER INFORMATION: n is a, c, g, or t
<220> FEATURE:
<221> NAME/KEY: misc_feature
<222> LOCATION: (350)..(352)
<223> OTHER INFORMATION: n is a, c, g, or t
<220> FEATURE:
<221> NAME/KEY: misc_feature
<222> LOCATION: (357)..(358)
<223> OTHER INFORMATION: n is a, c, g, or t
<220> FEATURE:
<221> NAME/KEY: misc_feature
<222> LOCATION: (360)..(362)
<223> OTHER INFORMATION: n is a, c, g, or t
<220> FEATURE:
<221> NAME/KEY: misc_feature
<222> LOCATION: (372)..(375)
<223> OTHER INFORMATION: n is a, c, g, or t
<220> FEATURE:
<221> NAME/KEY: misc_feature
<222> LOCATION: (378)..(383)
<223> OTHER INFORMATION: n is a, c, g, or t
<220> FEATURE:
<221> NAME/KEY: misc_feature
<222> LOCATION: (385)..(394)
<223> OTHER INFORMATION: n is a, c, g, or t
<220> FEATURE:
<221> NAME/KEY: misc_feature
<222> LOCATION: (397)..(398)
<223> OTHER INFORMATION: n is a, c, g, or t
<220> FEATURE:
<221> NAME/KEY: misc_feature
<222> LOCATION: (400)..(402)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (410)..(411)
<223> OTHER INFORMATION: n is a, c, g, or t
```

```
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(418)
<223> OTHER INFORMATION: n is a, c, g, or t
<220> FEATURE:
<221> NAME/KEY: misc_feature
<222> LOCATION: (421)..(423)
<223> OTHER INFORMATION: n is a, c, g, or t
<220> FEATURE:
<221> NAME/KEY: misc_feature
<222> LOCATION: (429)..(430)
<223> OTHER INFORMATION: n is a, c, g, or t
<220> FEATURE:
<221> NAME/KEY: misc_feature
<222> LOCATION: (433)..(437)
<223> OTHER INFORMATION: n is a, c, g, or t
<220> FEATURE:
<221> NAME/KEY: misc_feature
<222> LOCATION: (443)..(445)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (449)..(452)
<223> OTHER INFORMATION: n is a, c, g, or t
<220> FEATURE:
<221> NAME/KEY: misc_feature
<222> LOCATION: (454)..(457)
<223> OTHER INFORMATION: n is a, c, g, or t
<220> FEATURE:
<221> NAME/KEY: misc_feature
<222> LOCATION: (459)..(460)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (479)..(480)
<223> OTHER INFORMATION: n is a, c, g, or t
<220> FEATURE:
<221> NAME/KEY: misc_feature
<222> LOCATION: (483)..(494)
<223> OTHER INFORMATION: n is a, c, g, or t
<220> FEATURE:
<221> NAME/KEY: misc_feature
<222> LOCATION: (496)..(499)
<223> OTHER INFORMATION: n is a, c, g, or t
<220> FEATURE:
<221> NAME/KEY: misc_feature
<222> LOCATION: (501)..(502)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (506)..(514)
<223> OTHER INFORMATION: n is a, c, g, or t
<220> FEATURE:
<221> NAME/KEY: misc_feature
<222> LOCATION: (521)..(525)
<223> OTHER INFORMATION: n is a, c, g, or t
<220> FEATURE:
<221> NAME/KEY: misc_feature
<222> LOCATION: (527)..(532)
<223> OTHER INFORMATION: n is a, c, g, or t
<220> FEATURE:
<221> NAME/KEY: misc_feature
<222> LOCATION: (540)..(540)
```

<223> OTHER INFORMATION: n is a, c, g, or t
<220> FEATURE:
<221> NAME/KEY: misc_feature
<222> LOCATION: (542)..(543)
<223> OTHER INFORMATION: n is a, c, g, or t
<220> FEATURE:
<221> NAME/KEY: misc_feature
<222> LOCATION: (547)..(549)
<223> OTHER INFORMATION: n is a, c, g, or t
<220> FEATURE:
<221> NAME/KEY: misc_feature
<222> LOCATION: (551)..(565)
<223> OTHER INFORMATION: n is a, c, g, or t
<220> FEATURE:
<221> NAME/KEY: misc_feature
<222> LOCATION: (567)..(569)
<223> OTHER INFORMATION: n is a, c, g, or t
<220> FEATURE:
<221> NAME/KEY: misc_feature
<222> LOCATION: (571)..(576)
<223> OTHER INFORMATION: n is a, c, g, or t
<220> FEATURE:
<221> NAME/KEY: misc_feature
<222> LOCATION: (591)..(592)
<223> OTHER INFORMATION: n is a, c, g, or t
<220> FEATURE:
<221> NAME/KEY: misc_feature
<222> LOCATION: (594)..(595)
<223> OTHER INFORMATION: n is a, c, g, or t
<220> FEATURE:
<221> NAME/KEY: misc_feature
<222> LOCATION: (598)..(613)
<223> OTHER INFORMATION: n is a, c, g, or t
<220> FEATURE:
<221> NAME/KEY: misc_feature
<222> LOCATION: (616)..(651)
<223> OTHER INFORMATION: n is a, c, g, or t
<220> FEATURE:
<221> NAME/KEY: misc_feature
<222> LOCATION: (653)..(666)
<223> OTHER INFORMATION: n is a, c, g, or t
<220> FEATURE:
<221> NAME/KEY: misc_feature
<222> LOCATION: (671)..(715)
<223> OTHER INFORMATION: n is a, c, g, or t
<220> FEATURE:
<221> NAME/KEY: misc_feature
<222> LOCATION: (717)..(723)
<223> OTHER INFORMATION: n is a, c, g, or t
<220> FEATURE:
<221> NAME/KEY: misc_feature
<222> LOCATION: (726)..(788)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (792)..(801)
<223> OTHER INFORMATION: n is a, c, g, or t
<220> FEATURE:
<221> NAME/KEY: misc_feature
<222> LOCATION: (803)..(816)
<223> OTHER INFORMATION: n is a, c, g, or t

<400> SEQUENCE: 20

```
nnnnnnnnnn nnttgtgagt ctncnctctt gatgctttcg aacgantcct aantttcaca    60
aaatcctttt tttcttaatt gaaatcccaa tctgaatgcc tccaccttcc caactaactt   120
ttttctgacg atgcttctgg ttatgtcttc tcctccttac tttttatttt ctcctattta   180
ataataataa tggaatactt ggaattagta gaattctcca actacggaac caactgcttt   240
cccccccggg ggggggggg ggggnnnnc nnnnnnnncn cccnnaaan aaganaaaaa      300 aagngnnnnn annnnnnccc ccccncnn nntatacttt cnccnanntn nnccaanncn     360
```

```
nngggggggg gnnnnccnnn nnntnnnnnn nnnnaannan nnaaancccn nctnttnntt    420
nnnttagann aannnnnggc ccnnnangnn nngnnnnann ttttttttt tttggcncnn     480 aannnnnnnn nnnncnnnnc nncngnnnnn nnnnggggg nnnnnannnn nntcccccn     540 cnngccnnng nnnnnnnnnn nnnnnannng nnnnntttt tttttttttt nntnnggnnn    600
nnnnnnnnnn nnnaannnnn nnnnnnnnnn nnnnnnnnnn nnnnnnnnnn nannnnnnnn   660 nnnnntttt nnnnnnnnnn nnnnnnnnnn nnnnnnnnnn nnnnnnnnnn nnnncnnnn    720 nnnggnnnnn nnnnnnnnnn nnnnnnnnnn nnnnnnnnnn nnnnnnnnnn nnnnnnnnnn   780
nnnnnnnncn cnnnnnnnnn ngnnnnnnnn nnnnn                              816

<210> SEQ ID NO 21
<211> LENGTH: 864
<212> TYPE: DNA
<213> ORGANISM: Aegilops sharonensis
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (450)..(451)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (509)..(510)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (521)..(525)
<223> OTHER INFORMATION: n is a, c, g, or t
<220> FEATURE:
```

```
<221> NAME/KEY: misc_feature
<222> LOCATION: (527)..(528)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t
<220> FEATURE:
<221> NAME/KEY: misc_feature
<222> LOCATION: (559)..(561)
<223> OTHER INFORMATION: n is a, c, g, or t
<220> FEATURE:
<221> NAME/KEY: misc_feature
<222> LOCATION: (574)..(575)
<223> OTHER INFORMATION: n is a, c, g, or t
<220> FEATURE:
<221> NAME/KEY: misc_feature
<222> LOCATION: (591)..(593)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (601)..(602)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (607)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (627)..(630)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
```

```
<220> FEATURE:
<221> NAME/KEY: misc_feature
<222> LOCATION: (668)..(668)
<223> OTHER INFORMATION: n is a, c, g, or t
<220> FEATURE:
<221> NAME/KEY: misc_feature
<222> LOCATION: (671)..(672)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (697)..(698)
<223> OTHER INFORMATION: n is a, c, g, or t
<220> FEATURE:
<221> NAME/KEY: misc_feature
<222> LOCATION: (702)..(705)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (713)..(716)
<223> OTHER INFORMATION: n is a, c, g, or t
<220> FEATURE:
<221> NAME/KEY: misc_feature
<222> LOCATION: (718)..(720)
<223> OTHER INFORMATION: n is a, c, g, or t
<220> FEATURE:
<221> NAME/KEY: misc_feature
<222> LOCATION: (722)..(746)
<223> OTHER INFORMATION: n is a, c, g, or t
<220> FEATURE:
<221> NAME/KEY: misc_feature
<222> LOCATION: (753)..(755)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (778)..(779)
<223> OTHER INFORMATION: n is a, c, g, or t
<220> FEATURE:
<221> NAME/KEY: misc_feature
<222> LOCATION: (781)..(781)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (788)..(804)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (808)..(812)
```

<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t
<220> FEATURE:
<221> NAME/KEY: misc_feature
<222> LOCATION: (820)..(842)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (851)..(852)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (861)..(862)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t

<400> SEQUENCE: 21

| | | | | | |
|---|---|---|---|---|---|
| nnnnnnnnnn | cttctgantc | tcnnttcctc | ctcctccggn | gantnggttg | ggcttctatc | 60 |
| naagaggtaa | ngataccgct | atcgctatgc | tcatatctcc | cttccctcct | ccaggtgaga | 120 |
| agctggtgat | tctggttatg | gcttctcctc | tttactttt | atattctcct | atttaataat | 180 |
| aataatggaa | tacttggaat | taggagaatt | ctccaaatac | ggaaccaact | gctttcccnc | 240 |
| cgggggggggg | gggggggggg | cgcgggagg | aacggcccga | agaaaatcga | aaaaaaaccg | 300 |
| aaaaaatttg | cccccccccc | tcttatttaa | tatttctcct | aagtaacccc | ttgccggggg | 360 |
| gggggggcca | cccctttgta | aaggggaaaa | aagaggaaaa | tccccctct | ttcttatatg | 420 |
| agaaaaattc | ccgacccgga | gaggaagggn | ngctctttt | tttcgtttag | ccccaataac | 480 |
| ccntatttcc | tttcctcccg | gtggggtgnn | gggaaanaaa | nnnnncnngn | cccccccgc | 540 |
| ncggggggggg | gaagaanann | naaagcgacg | gagnngcttt | tttttttttt | nnncnccncc | 600 |
| nnggngnnnn | nnnnnnnnnn | ncnnccnnnn | cttccttttn | ttntnngttt | tagaganaaa | 660 |
| ananaagnga | nncattttt | tttttttctn | tntttgnnga | gnnngntcc | ccnnngnnn | 720 |
| gnnnnnnnnn | nnnnnnnnnn | nnnnnngggg | ggnnaggng | nnaggaaaaa | ggggcncnnt | 780 |
| nctccntnnn | nnnnnnnnnn | nnnananann | nncctctntn | nnnnnnnnnn | nnnnnnnnnn | 840 |
| nnaanaggng | nngggngngg | nngn | | | | 864 |

<210> SEQ ID NO 22
<211> LENGTH: 864
<212> TYPE: DNA
<213> ORGANISM: Aegilops sharonensis
<220> FEATURE:
<221> NAME/KEY: misc_feature
<222> LOCATION: (1)..(10)
<223> OTHER INFORMATION: n is a, c, g, or t

```
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (723)..(724)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t
<220> FEATURE:
<221> NAME/KEY: misc_feature
<222> LOCATION: (769)..(770)
<223> OTHER INFORMATION: n is a, c, g, or t
<220> FEATURE:
<221> NAME/KEY: misc_feature
<222> LOCATION: (772)..(780)
<223> OTHER INFORMATION: n is a, c, g, or t
<220> FEATURE:
<221> NAME/KEY: misc_feature
<222> LOCATION: (785)..(797)
<223> OTHER INFORMATION: n is a, c, g, or t
<220> FEATURE:
<221> NAME/KEY: misc_feature
<222> LOCATION: (799)..(810)
<223> OTHER INFORMATION: n is a, c, g, or t
<220> FEATURE:
<221> NAME/KEY: misc_feature
<222> LOCATION: (812)..(821)
<223> OTHER INFORMATION: n is a, c, g, or t
<220> FEATURE:
<221> NAME/KEY: misc_feature
<222> LOCATION: (823)..(830)
<223> OTHER INFORMATION: n is a, c, g, or t
<220> FEATURE:
<221> NAME/KEY: misc_feature
<222> LOCATION: (833)..(835)
<223> OTHER INFORMATION: n is a, c, g, or t
<220> FEATURE:
<221> NAME/KEY: misc_feature
<222> LOCATION: (838)..(839)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (847)..(856)
<223> OTHER INFORMATION: n is a, c, g, or t
<220> FEATURE:
<221> NAME/KEY: misc_feature
<222> LOCATION: (862)..(864)
<223> OTHER INFORMATION: n is a, c, g, or t

<400> SEQUENCE: 22
nnnnnnnnnn tcttctgagt tcttccntct tgatgctttc gaacgactcc taaatttcac      60
aaaatccttt ttttcttatt tgaaatccaa atcgaaatgc ctcaacttga taaattaact     120
tatttctcac aattcttctg gttatgtctt ctcctcttta cttttatat tctcttattt     180 aataataata atggaatact tggaattagt agaattctca aactacggaa ccaactgctt     240
```

```
tcgcaccggg ggggcgagat ccggagcaag gaccctaaga atctggaaga tatctcgaga    300
aaaggtttta gcaccggtct ctcatatatg tactccagtt tatccgaagt atcccaatgg    360
tgtaagaccg tcgactattt gggaaaaagg aggaaaatca ctctgatctc tgatttcgga    420
gaaataagtg gctcacgagg aatggagaga cagattctct atttgatctc gaagtcctca    480
tataacactt cttccagtcg gatcacttgt tggaaaaaca taatgctcac acatgttcca    540
cacgggcaag gaagcataat atcatgaaag ccgtctgata atctttctat aggttccccg    600
aanagaatgg aaaaatcaca aaaacacttt ctatatgttc tgttatttcg agattcgaag    660
aagcaagcaa gtttttcata tagctgtttc ctgtgtagtg atctctgttc gtggagatca    720
tgnnggcccc tgatncccnt gtggtacggg gggggggaa nnaaaaaann gnnnnnnnnn    780
ctttnnnnnn nnnnnnnann nnnnnnnnnn cnnnnnnnnn ntnnnnnnnn ccnnnccnnc    840
ccccngnnnn nnnnnngggg gnnn                                          864
```

<210> SEQ ID NO 23
<211> LENGTH: 885
<212> TYPE: DNA
<213> ORGANISM: Aegilops sharonensis
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (769)..(773)
<223> OTHER INFORMATION: n is a, c, g, or t
<220> FEATURE:
<221> NAME/KEY: misc_feature
<222> LOCATION: (776)..(785)
<223> OTHER INFORMATION: n is a, c, g, or t
<220> FEATURE:
<221> NAME/KEY: misc_feature
<222> LOCATION: (791)..(793)
<223> OTHER INFORMATION: n is a, c, g, or t
<220> FEATURE:
<221> NAME/KEY: misc_feature
<222> LOCATION: (800)..(804)
<223> OTHER INFORMATION: n is a, c, g, or t
<220> FEATURE:
<221> NAME/KEY: misc_feature
<222> LOCATION: (806)..(811)
<223> OTHER INFORMATION: n is a, c, g, or t
<220> FEATURE:
<221> NAME/KEY: misc_feature
<222> LOCATION: (815)..(823)
<223> OTHER INFORMATION: n is a, c, g, or t
<220> FEATURE:
<221> NAME/KEY: misc_feature
<222> LOCATION: (827)..(830)
<223> OTHER INFORMATION: n is a, c, g, or t
<220> FEATURE:
<221> NAME/KEY: misc_feature
<222> LOCATION: (834)..(849)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t -continued
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (857)..(859)
<223> OTHER INFORMATION: n is a, c, g, or t
<220> FEATURE:
<221> NAME/KEY: misc_feature
<222> LOCATION: (861)..(880)
<223> OTHER INFORMATION: n is a, c, g, or t
<220> FEATURE:
<221> NAME/KEY: misc_feature
<222> LOCATION: (882)..(883)
<223> OTHER INFORMATION: n is a, c, g, or t

<400> SEQUENCE: 23

```
nnnnnnnnnn nnnntnctga gtcttcctct tgatgctttc gaacgactcc taaatttcac      60
aaaatccttt ttttcttatt tgaaatccaa atcgaaatgc ctcaacttga taaattaact     120
tatttctcac aattcttctg gttatgtctt ctcctcttta ctttttatat tctcttattt     180
aataataata atggaatact tggaattagt agaattctca aactacggaa ccaactgctt     240
tcgcaccggg ggggcgagat ccggagcaag gaccctaaga atctggaaga tatctcgaga     300
aaaggtttta gcaccggtct ctcatatatg tactccagtt tatccgaagt atcccaatgg     360
tgtaagaccg tcgactattt gggaaaaagg aggaaaatca ctctgatctc tgatttcgga     420
gaaataagtg gctcacnagg aatggagaga cagattctct atttgatctc gaagtcctca     480
tataacactt cttccagtcg gatcacttgt tggaaaaaca taatgctcac acatgttcca     540
cacgggcaag gaagcataat atcatgaaag ccgtctgata atctttctat aggttccccg     600
aagagaatgg aaaaatcaca aaacactttt ctatatgttc tgttatttcg agattcgaag     660
aagcaagcaa gttttttcata tagctgtttc ctgtgtagtg atctctgttc gtggagatca     720
tgaggcccct gatacccgt ggtacggggg ggggnaaaa aaagagggnn nnnggnnnnn     780
nnnnnaaaaa nnnaaaaaan nnncnnnnn ntttnnnnnn nnntcnnnnn cccnnnnnnn     840
nnnnnnnnng gngnaannng nnnnnnnnnn nnnnnnnnnn tnntt                      885
```

<210> SEQ ID NO 24
<211> LENGTH: 854
<212> TYPE: DNA
<213> ORGANISM: Triticum zhukovskyi
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (844)..(847)
<223> OTHER INFORMATION: n is a, c, g, or t

<400> SEQUENCE: 24

```
nnnnnnnnnn nntnctgagt cttccntct tgatgctttc gaacgactcc taaatttcac      60
aaaatccttt ttttcttatt tgaaatccaa atcgaaatgc ctcaacttga taaattaact     120
tatttctcac aattcttctg gttatgtctt ctcctcttta ctttttatat tctcttattt     180
```

| | | |
|---|---|---|
| aataataata atgaatact tggaattagt agaattctca aactacggaa ccaactgctt | 240 |
| tcgcaccggg ggggcgagat ccggagcaag gaccctaaga atctggaaga tatctcgaga | 300 |
| aaaggtttta gcaccggtct ctcatatatg tactccagtt tatccgaagt atcccaatgg | 360 |
| tgtaagaccg tcgactattt gggaaaaagg aggaaaatca ctctgatctc tgatttcgga | 420 |
| gaaataagtg gctcacgagg aatggagaga cagattctct atttgatctc gaagtcctca | 480 |
| tataacactt cttccagtcg gatcacttgt tggaaaaaca taatgctcac acatgttcca | 540 |
| cacgggcaag gaagcataat atcatgaaag ccgtctgata atctttctat aggttccccg | 600 |
| aagagaatgg aaaaatcaca aaaacacttt ctatatgttc tgttatttcg agattcgaag | 660 |
| aagcaagcaa gttttttcata tagcagtttc ctgtgtagtg atctctgttc gtggagatca | 720 |
| tgaggcccct gatacccctgt ggtacggggg ggggtagaag agtgggcatg tgggcttcta | 780 |
| tcaaaagagg aaaagatacc gctatcgcta tgctcatatc tcccttccct cctccagtga | 840 |
| gaannnnggt ggaa | 854 |

<210> SEQ ID NO 25
<211> LENGTH: 854
<212> TYPE: DNA
<213> ORGANISM: Triticum zhukovskyi
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (840)..(841)
<223> OTHER INFORMATION: n is a, c, g, or t
<220> FEATURE:
<221> NAME/KEY: misc_feature
<222> LOCATION: (844)..(848)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t

<400> SEQUENCE: 25

| | | |
|---|---|---|
| nnnnnnnnnn nnnctnntga gnnntccctc ttgatgcttt cgaacgactc ctaaatttca | 60 |
| caaaatcctt tttttcttat ttgaaatcca aatcgaaatg cctcaacttg ataaattaac | 120 |
| ttatttctca caattcttct ggttatgtct tctcctcttt acttttata ttctcttatt | 180 |
| taataataat aatggaatac ttggaattag tagaattctc aaactacgga accaactgct | 240 |
| ttcgcaccgg ggggcgaga tccggagcaa ggaccctaag aatctggaag atatctcgag | 300 |
| aaaaggtttt agcaccggtc tctcatatat gtactccagt ttatccgaag tatcccaatg | 360 |
| gtgtaagacc gtcgactatt tgggaaaaag gaggaaaatc actctgatct ctgatttcgg | 420 |
| agaaataagt ggctcacgag gaatggagag acagattctc tatttgatct cgaagtcctc | 480 |
| atataacact tcttccagtc ggatcacttg ttggaaaaac ataatgctca cacatgttcc | 540 |
| acacgggcaa ggaagcataa tatcatgaaa gccgtctgat aatctttcta taggttcccc | 600 |
| gaagagaatg gaaaaatcac aaaaacactt tctatatgtt ctgttatttc gagattcgaa | 660 |
| gaagcaagca agttttttcat atagcagttt cctgtgtagt gatctctgtt cgtggagatc | 720 |

| atgaggcccc tgatacctg tggtacgggg gggggtagaa gagtgggcat gtgggcttct | 780 |
| atcaaaagag gaaaagatac cgctatcgct atgctcatat ctcccttccc tcctccagtn | 840 |
| naannnnntg tnna | 854 |

<210> SEQ ID NO 26
<211> LENGTH: 888
<212> TYPE: DNA
<213> ORGANISM: Triticum timopheevii
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (839)..(841)
<223> OTHER INFORMATION: n is a, c, g, or t
<220> FEATURE:
<221> NAME/KEY: misc_feature
<222> LOCATION: (845)..(848)
<223> OTHER INFORMATION: n is a, c, g, or t
<220> FEATURE:
<221> NAME/KEY: misc_feature
<222> LOCATION: (856)..(863)
<223> OTHER INFORMATION: n is a, c, g, or t
<220> FEATURE:
<221> NAME/KEY: misc_feature
<222> LOCATION: (865)..(886)
<223> OTHER INFORMATION: n is a, c, g, or t

<400> SEQUENCE: 26

| nnnnnnnnnn nttntnctga gnnntccctc ttgatgcttt cgaacgactc ctaaatttca | 60 |
| caaaatcctt tttttcttat ttgaaatcca atcgaaatg cctcaacttg ataaattaac | 120 |
| ttatttctca caattcttct ggttatgtct tctcctcttt acttttata ttctcttatt | 180 |
| taataataat aatggaatac ttggaattag tagaattctc aaactacgga accaactgct | 240 |
| ttcgcaccgg gggggcgaga tccggagcaa ggaccctaag aatctggaag atatctcgag | 300 |
| aaaaggtttt agcaccggtc tctcatatat gtactccagt ttatccgaag tatcccaatg | 360 |
| gtgtaagacc gtcgactatt tgggaaaaag gaggaaaatc actctgatct ctgatttcgg | 420 |
| agaaataagt ggctcacgag gaatggagag acagattctc tatttgatct cgaagtcctc | 480 |
| atataacact tcttccagtc ggatcacttg ttggaaaaac ataatgctca cacatgttcc | 540 |
| acacgggcaa ggaagcataa tatcatgaaa gccgtctgat aatctttcta taggttcccc | 600 |
| gaagagaatg gaaaaatcac aaaaacactt tctatatgtt ctgttatttc gagattcgaa | 660 |
| gaagcaagca agttttttcat atagcagttt cctgtgtagt gatctctgtt cgtggagatc | 720 |
| atgaggcccc tgatacctg tggtacgggg gggggtagaa gagtgggcat gtgggcttct | 780 |
| atcaaaagag gaaaagatac cgctatcgct atgctcatat ctcccttccc tcctccagnn | 840 |
| nagannnngg tggagnnnnn nnannnnnn nnnnnnnnnn nnnnnggg | 888 |

<210> SEQ ID NO 27

```
<211> LENGTH: 858
<212> TYPE: DNA
<213> ORGANISM: Triticum aestivum
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (838)..(839)
<223> OTHER INFORMATION: n is a, c, g, or t
<220> FEATURE:
<221> NAME/KEY: misc_feature
<222> LOCATION: (841)..(843)
<223> OTHER INFORMATION: n is a, c, g, or t
<220> FEATURE:
<221> NAME/KEY: misc_feature
<222> LOCATION: (846)..(851)
<223> OTHER INFORMATION: n is a, c, g, or t

<400> SEQUENCE: 27
nnnnnnnnnn nnnnntnctg agttcttccc tcttgatgct ttcgaacgac tcctaaattt    60
cacaaaatcc ttttttcttt atttgaaatc caaatcgaaa tgcctcaact tgataaatta   120
acttatttct cacaattctt ctggttatgt cttctcctct ttacttttta tattctctta   180
tttaataata ataatggaat acttggaatt agtagaattc tcaaactacg gaaccaactg   240
ctttcgcacc gggggggcga gatccggagc aaggaccta agaatctgga agatatctcg    300
agaaaaggtt ttagcaccgg tctctcatat atgtactcca gtttatccga agtatcccaa   360
tggtgtaaga ccgtcgacta tttgggaaaa aggaggaaaa tcactctgat ctctgatttc   420
ggagaaataa gtggctcacg aggaatggag agacagattc tctatttgat ctcgaagtcc   480
tcatataaca cttcttccag tcggatcact tgttggaaaa acataatgct cacacatgtt   540
ccacacgggc aaggaagcat aatatcatga aagccgtctg ataatctttc tataggttcc   600
ccgaagagaa tggaaaaatc acaaaaacac tttctatatg ttctgttatt tcgagattcg   660
aagaagcaag caagtttttc atatagctgt ttcctgtgta gtgatctctg ttcgtggaga   720
tcatgaggcc cctgataccc tgtggtacgg ggggggtag aagagtgggc atgtgggctt    780
ctatcaaaag aggaaaagat accgctatcg ctatgctcat atctcccttc cctcctcnng   840
nnnaannnnn nggggaag                                                 858

<210> SEQ ID NO 28
<211> LENGTH: 858
<212> TYPE: DNA
<213> ORGANISM: x Triticosecale
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (15)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (33)..(36)
<223> OTHER INFORMATION: n is a, c, g, or t
<220> FEATURE:
<221> NAME/KEY: misc_feature
```

```
<222> LOCATION: (848)..(848)
<223> OTHER INFORMATION: n is a, c, g, or t
<220> FEATURE:
<221> NAME/KEY: misc_feature
<222> LOCATION: (851)..(852)
<223> OTHER INFORMATION: n is a, c, g, or t

<400> SEQUENCE: 28
nnnnnnnnnn nnnannnnnn nnnctgantc ttnnnnttga tgctttcgaa cgactcctaa      60
atttcacaaa atccttttt tcttatttga aatccaaatc gaaatgcctc aacttgataa      120
attaacttat ttctcacaat tcttctggtt atgtcttctc ctctttactt tttatattct    180
cttatttaat aataataatg gaatacttgg aattagtaga attctcaaac tacggaacca    240
actgctttcg caccggggg gcgagatccg gagcaaggac cctaagaatc tggaagatat     300
ctcgagaaaa ggttttagca ccggtctctc atatatgtac tccagtttat ccgaagtatc    360
ccaatggtgt aagaccgtcg actatttggg aaaaggagg aaaatcactc tgatctctga     420
tttcggagaa ataagtggct cacgaggaat ggagagacag attctctatt tgatctcgaa    480
gtcctcatat aacacttctt ccagtcggat cacttgttgg aaaaacataa tgctcacaca    540
tgttccacac gggcaaggaa gcataatatc atgaaagccg tctgataatc tttctatagg    600
ttccccgaag agaatggaaa aatcacaaaa acactttcta tatgttctgt tatttcgaga    660
ttcgaagaag caagcaagtt tttcatatag ctgtttcctg tgtagtgatc tctgttcgtg    720
gagatcatga ggcccctgat accctgtggt acggggggg gtagaagagt gggcatgtgg    780
gcttctatca aaagaggaaa agataccgct atcgctatgc tcatatctcc cttccctcct    840
ccaggganaa nnctggtg                                                    858

<210> SEQ ID NO 29
<211> LENGTH: 860
<212> TYPE: DNA
<213> ORGANISM: x Triticosecale
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (839)..(841)
<223> OTHER INFORMATION: n is a, c, g, or t
<220> FEATURE:
<221> NAME/KEY: misc_feature
<222> LOCATION: (844)..(848)
<223> OTHER INFORMATION: n is a, c, g, or t
<220> FEATURE:
<221> NAME/KEY: misc_feature
<222> LOCATION: (855)..(856)
<223> OTHER INFORMATION: n is a, c, g, or t

<400> SEQUENCE: 29
nnnnnnnnnt nnntnctgag nncttccctc ttgatgcttt cgaacgactc ctaaatttca      60
caaaatcctt tttttcttat ttgaaatcca atcgaaatg cctcaacttg ataaattaac     120
```

-continued

```
ttatttctca caattcttct ggttatgtct tctcctcttt acttttata ttctcttatt      180 taataataat aatggaatac ttggaattag tagaattctc aaactacgga accaactgct      240
ttcgcaccgg gggggcgaga tccggagcaa ggaccctaag aatctggaag atatctcgag      300
aaaaggtttt agcaccggtc tctcatatat gtactccagt ttatccgaag tatcccaatg      360
gtgtaagacc gtcgactatt tgggaaaaag gaggaaaatc actctgatct ctgatttcgg      420
agaaataagt ggctcacgag gaatggagag acagattctc tatttgatct cgaagtcctc      480
atataacact tcttccagtc ggatcacttg ttggaaaaac ataatgctca cacatgttcc      540
acacgggcaa ggaagcataa tatcatgaaa gccgtctgat aatctttcta taggttcccc      600
gaagagaatg gaaaaatcac aaaaacactt tctatatgtt ctgttatttc gagattcgaa      660
gaagcaagca agtttttcat atagctgttt cctgtgtagt gatctctgtt cgtggagatc      720
atgaggcccc tgatacccctg tggtacgggg gggggtagaa gagtgggcat gtgggcttct      780
atcaaaagag gaaagatac cgctatcgct atgctcatat ctcccttccc tcctccagnn      840
naannnnngg tgaannaaaa                                                  860
```

<210> SEQ ID NO 30
<211> LENGTH: 510
<212> TYPE: DNA
<213> ORGANISM: x Triticosecale
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: misc_feature
<222> LOCATION: (136)..(139)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (145)..(146)
<223> OTHER INFORMATION: n is a, c, g, or t
<220> FEATURE:
<221> NAME/KEY: misc_feature
<222> LOCATION: (148)..(150)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (156)..(159)
<223> OTHER INFORMATION: n is a, c, g, or t
<220> FEATURE:
<221> NAME/KEY: misc_feature
<222> LOCATION: (165)..(166)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t -continued

```
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (195)..(197)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (225)..(227)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (247)..(248)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (257)..(261)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (291)..(291)
```

-continued

```
<223> OTHER INFORMATION: n is a, c, g, or t
<220> FEATURE:
<221> NAME/KEY: misc_feature
<222> LOCATION: (306)..(307)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (342)..(343)
<223> OTHER INFORMATION: n is a, c, g, or t
<220> FEATURE:
<221> NAME/KEY: misc_feature
<222> LOCATION: (349)..(350)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (368)..(370)
<223> OTHER INFORMATION: n is a, c, g, or t
<220> FEATURE:
<221> NAME/KEY: misc_feature
<222> LOCATION: (377)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (410)..(412)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
```

```
<222> LOCATION: (423)..(423)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(433)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (468)..(470)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (484)..(485)
<223> OTHER INFORMATION: n is a, c, g, or t
<220> FEATURE:
<221> NAME/KEY: misc_feature
<222> LOCATION: (487)..(487)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t

<400> SEQUENCE: 30
nnnnnnnnnn nnnnntgata tctcccttnn ncctcctcca ggtgaattag gttgggcttc      60
tatcaaaaga ggaaaagata ccgctatcgc tatgctcata tctcccttcc ctcctccagg     120
tgagaagctg gtgaannnnt tnttnntnnn tcancnnnna ggggnnttcn nttttttgtng    180 gntggtccna ctatnnncng nggnnnnggn ggggagactt agccnnnaac ggntncttt     240 gngnngnntt tntntcnnnn nangacctgc tgnttgtcca antttctcnc ntaaaggctt    300 tataanncen ttncnttttt accctcngaa tanagganat cnnttttcnn tntnggggtt    360
actgtttnnn gttgaanngg gganaacatc ttnananacc tttatccggn nnatatgntg    420
```
tgncnagant gnncgnccat cgcnctattt tcctgcggng nacgcatnnn catnttntcc    480
attnngntca atttgctgca aangntttn                                     510

<210> SEQ ID NO 31
<211> LENGTH: 892
<212> TYPE: DNA
<213> ORGANISM: x Triticosecale
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (838)..(840)
<223> OTHER INFORMATION: n is a, c, g, or t
<220> FEATURE:
<221> NAME/KEY: misc_feature
<222> LOCATION: (844)..(847)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (856)..(891)
<223> OTHER INFORMATION: n is a, c, g, or t

<400> SEQUENCE: 31
nnnnnnnnnn nntnctgagt tcttccctct tgatgctttc gaacgactcc taaatttcac     60
aaaatccttt ttttcttatt tgaaatccaa atcgaaatgc ctcaacttga taaattaact    120
tatttctcac aatttcttctg gttatgtctt ctcctcttta cttttatat tctcttattt    180 aataataata atggaatact tggaattagt agaattctca aactacggaa ccaactgctt    240
tcgcaccggg ggggcgagat ccggagcaag gaccctaaga atctggaaga tatctcgaga    300
aaaggtttta gcaccggtct ctcatatatg tactccagtt tatccgaagt atcccaatgg    360
tgtaagaccg tcgactattt gggaaaaagg aggaaaatca ctctgatctc tgatttcgga    420
gaaataagtg gctcacgagg aatggagaga cagattctct atttgatctc gaagtcctca    480
tataacactt cttccagtcg gatcacttgt tggaaaaaca taatgctcac acatgttcca    540
cacgggcaag gaagcataat atcatgaaag ccgtctgata atctttctat aggttccccg    600
aagagaatgg aaaaatcaca aaaacacttt ctatatgttc tgttatttcg agattcgaag    660
aagcaagcaa gttttcata tagctgttc ctgtgtagtg atctctgttc gtggagatca    720
tgaggcccct gatacccctgt ggtacggggg ggggtagaag agtgggcatg tgggcttcta    780
tcaaaagagg aaaagatacc gctatcgcta tgctcatatc tcccttccct cctccagnnn    840
agannnnggt gnagannnnn nnnnnnnnnnn nnnnnnnnnn nnnnnnnnnn nt           892

<210> SEQ ID NO 32
<211> LENGTH: 854
<212> TYPE: DNA
<213> ORGANISM: x Triticosecale
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

```
-continued

<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (262)..(263)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (299)..(301)
<223> OTHER INFORMATION: n is a, c, g, or t
<220> FEATURE:
<221> NAME/KEY: misc_feature
<222> LOCATION: (321)..(322)
<223> OTHER INFORMATION: n is a, c, g, or t
<220> FEATURE:
<221> NAME/KEY: misc_feature
<222> LOCATION: (325)..(329)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (360)..(361)
```

```
<223> OTHER INFORMATION: n is a, c, g, or t
<220> FEATURE:
<221> NAME/KEY: misc_feature
<222> LOCATION: (366)..(367)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (404)..(406)
<223> OTHER INFORMATION: n is a, c, g, or t
<220> FEATURE:
<221> NAME/KEY: misc_feature
<222> LOCATION: (408)..(409)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (415)..(416)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (439)..(440)
<223> OTHER INFORMATION: n is a, c, g, or t
<220> FEATURE:
<221> NAME/KEY: misc_feature
<222> LOCATION: (449)..(453)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (472)..(474)
<223> OTHER INFORMATION: n is a, c, g, or t
<220> FEATURE:
<221> NAME/KEY: misc_feature
<222> LOCATION: (484)..(485)
<223> OTHER INFORMATION: n is a, c, g, or t
<220> FEATURE:
<221> NAME/KEY: misc_feature
<222> LOCATION: (490)..(491)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t
<220> FEATURE:
<221> NAME/KEY: misc_feature
<222> LOCATION: (508)..(509)
<223> OTHER INFORMATION: n is a, c, g, or t
<220> FEATURE:
<221> NAME/KEY: misc_feature
```

```
<222> LOCATION: (524)..(524)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (534)..(539)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (555)..(557)
<223> OTHER INFORMATION: n is a, c, g, or t
<220> FEATURE:
<221> NAME/KEY: misc_feature
<222> LOCATION: (559)..(560)
<223> OTHER INFORMATION: n is a, c, g, or t
<220> FEATURE:
<221> NAME/KEY: misc_feature
<222> LOCATION: (563)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (590)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(598)
<223> OTHER INFORMATION: n is a, c, g, or t
<220> FEATURE:
<221> NAME/KEY: misc_feature
<222> LOCATION: (605)..(606)
<223> OTHER INFORMATION: n is a, c, g, or t
<220> FEATURE:
```

```
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (707)..(708)
<223> OTHER INFORMATION: n is a, c, g, or t
<220> FEATURE:
<221> NAME/KEY: misc_feature
<222> LOCATION: (712)..(714)
<223> OTHER INFORMATION: n is a, c, g, or t
```

```
<220> FEATURE:
<221> NAME/KEY: misc_feature
<222> LOCATION: (725)..(726)
<223> OTHER INFORMATION: n is a, c, g, or t
<220> FEATURE:
<221> NAME/KEY: misc_feature
<222> LOCATION: (728)..(729)
<223> OTHER INFORMATION: n is a, c, g, or t
<220> FEATURE:
<221> NAME/KEY: misc_feature
<222> LOCATION: (733)..(735)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (741)..(744)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t
<220> FEATURE:
<221> NAME/KEY: misc_feature
<222> LOCATION: (748)..(749)
<223> OTHER INFORMATION: n is a, c, g, or t
<220> FEATURE:
<221> NAME/KEY: misc_feature
<222> LOCATION: (758)..(760)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (766)..(768)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (772)..(779)
<223> OTHER INFORMATION: n is a, c, g, or t
<220> FEATURE:
<221> NAME/KEY: misc_feature
<222> LOCATION: (782)..(783)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (788)..(823)
<223> OTHER INFORMATION: n is a, c, g, or t
<220> FEATURE:
<221> NAME/KEY: misc_feature
<222> LOCATION: (827)..(829)
<223> OTHER INFORMATION: n is a, c, g, or t
<220> FEATURE:
<221> NAME/KEY: misc_feature
<222> LOCATION: (833)..(854)
<223> OTHER INFORMATION: n is a, c, g, or t

<400> SEQUENCE: 32
nnnnnnnnnn nnnnctnctg agttcttccc tcttgatgct ttcgaacgac tcctaaattt      60
cacaaaatcc ttttttnntn ntttgaaatc caaatcgaaa tgcctcanct tgataaatta     120
acttatttcn cacaattctt ctggttatgt cttcccccct ttacttttta tattccctta     180
tttaaaaata anaatggaat acttggaatt agnagaattc tcaaactacg gaaccaactg     240
```

-continued

```
ctttcgcncc ggggggggggg gnnccggngc agggccccta aaaattngga aaattttttnn    300 ngaaaaggtt ttagccccgg nntcnnnnnt ntntccccccn gtttntccna agtntcccan    360 ngggggnnana ccgtcgnctt tttgggaaaa aggggggaaaa tccnnntnnt ctntnntttc    420
ggaaaaaaaa ggggcnccnn gggaagggnn nnncaaattc tnttttttgat cnnnaagccc    480 tcanntaacn nttntnccng ccggancnnt tgttggaaaa acanaangnt cncnnnnnnc    540
ccncncgggn aaggnnncnn aanntcntga aagccgncg anaatntttn natnggnncc    600
ccgannagaa tggaaaaanc ncaaaaacnc tttntntntn ttntgttntt tcnngattcn    660
aaaaancaag naagttttttc anatagctnt ttcctgnggn gngatcnntg tnnngggaga    720
tcatnngnnc ccnnnanccc nnnngnanng ggggggggnnn aaananngn gnnnnnnnnt    780 tnntnnannn nnnnnnnnn nnnnnnnnn nnnnnnnnn nnncccnnnc ccnnnnnnnn        840
nnnnnnnnnn nnnn    854
```

```
<210> SEQ ID NO 33
<211> LENGTH: 1046
<212> TYPE: DNA
<213> ORGANISM: Aegilops sharonensis
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (31)..(37)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (990)..(991)
<223> OTHER INFORMATION: n is a, c, g, or t
<220> FEATURE:
<221> NAME/KEY: misc_feature
<222> LOCATION: (1006)..(1009)
<223> OTHER INFORMATION: n is a, c, g, or t
<220> FEATURE:
<221> NAME/KEY: misc_feature
<222> LOCATION: (1013)..(1017)
<223> OTHER INFORMATION: n is a, c, g, or t
<220> FEATURE:
<221> NAME/KEY: misc_feature
<222> LOCATION: (1022)..(1024)
<223> OTHER INFORMATION: n is a, c, g, or t
<220> FEATURE:
<221> NAME/KEY: misc_feature
<222> LOCATION: (1026)..(1027)
<223> OTHER INFORMATION: n is a, c, g, or t
<220> FEATURE:
<221> NAME/KEY: misc_feature
<222> LOCATION: (1029)..(1031)
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1036)..(1037)
<223> OTHER INFORMATION: n is a, c, g, or t
<220> FEATURE:
<221> NAME/KEY: misc_feature
<222> LOCATION: (1040)..(1041)
<223> OTHER INFORMATION: n is a, c, g, or t
```

<400> SEQUENCE: 33

```
nnnnnnnnnn nnnnnnnnnt ctnnnataag nnnnnnncag aataagtact aatgctctgt      60
ataatacttt tccccgagcg atggtttagc ggattcggaa ttgtaaccaa gcatcctggg     120
ttctataccc gattcaacac tagagcatgc agccgatcct ggatacataa ctatataaag     180
tgtgccgttt tggatctta ttggtagcca gtctttcact tctgcctctc cactcccatg      240
cctttcttgg tcggaccaac ccaaccggcg atttccgaca agtctttctg cttagagcaa     300
gaagcggaac caaaataaag ctttctttat tttcatttat ggataaccaa tccatttcc      360
aatatagttg ggagatttta cccaagaaat gggtacataa aatgaaaaga tcggaacatg     420
ggaatagatc ttataccaat actgactacc catttccatt gttgtgcttt ctaaaatggc     480
atacctatac aagggttcaa gtttcgatcg atatttgcgg agtggatcat ccctctcgaa     540
aacgaagatt tgaagttgtc cataatttac tgagtactcg gtataactca cgcattcgtg     600
tacaaacaag tgcagacgaa gtaacacgaa tatctccggt agtcagtcta tttccatcag     660
ccggccggtg ggagcgagaa gtatgggata tgtctggtgt ttcttccatc aatcatccgg     720
atttacgccg tatatcaaca gattatggtt tcgagggtca tccattacga aaagactttc     780
ctctgagtgg atatgtggaa gtacgctatg atgatccaga gaaacgtgtg gtttctgaac     840
ccattgagat gacccaagaa tttcgctatt tcgattttgc tagtccttgg gaacagcgta     900
gcgacggata attccgaatc tacataggtc tagtccaggg gacaaatcaa tagaaatgct     960
atttgcttct tagaagaaga ntttttgaan ngaagagttc ccggcnnnng gannnnntta    1020
annnanntnn ngnccnncgn nagcaa                                         1046
```

<210> SEQ ID NO 34
<211> LENGTH: 1030
<212> TYPE: DNA
<213> ORGANISM: Aegilops sharonensis
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(14)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1016)..(1020)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t

<400> SEQUENCE: 34

-continued

```
nnnnnnnnnc nnnntctnnn ataaggaaag gancagaata agtactaatg ctctgtataa      60
tacttttccc cgagcgatgg tttagcggat tcggaattgt aaccaagcat cctgggttct     120
atacccgatt caacactaga gcatgcagcc gatcctggat acataactat ataaagtgtg     180
ccgttttgga tctttattgg tagccagtct ttcacttctg cctctccact cccatgcctt     240
tcttggtcgg accaacccaa ccggcgattt ccgacaagtc tttctgctta gagcaagaag     300
cggaaccaaa ataaagcttt ctttattttc atttatggat aaccaatcca ttttccaata     360
tagttgggag attttaccca agaaatgggt acataaaatg aaaagatcgg aacatgggaa     420
tagatcttat accaatactg actacccatt tccattgttg tgctttctaa aatggcatac     480
ctatacaagg gttcaagttt cgatcgatat ttgcggagtg gatcatccct ctcgaaaacg     540
aagatttgaa gttgtccata atttactgag tactcggtat aactcacgca ttcgtgtaca     600
aacaagtgca gacgaagtaa cacgaatatc tccggtagtc agtctatttc catcagccgg     660
ccggtgggag cgagaagtat gggatatgtc tggtgtttct tccatcaatc atccggattt     720
acgccgtata tcaacagatt atggtttcga gggtcatcca ttacgaaaag actttcctct     780
gagtggatat gtggaagtac gctatgatga tccagagaaa cgtgtggttt ctgaacccat     840
tgagatgacc caagaatttc gctatttcga ttttgctagt ccttgggaac agcgtagcga     900
cggataattc cgaatctaca taggtctagt ccagggggaca aatcaatagg aaatgctatt     960
tgcttcttaa gaagaagaac ttttttgaaa tgaaagagtt ccacggcgcg gggnannnnn    1020
tnaaanaaaa                                                            1030
```

<210> SEQ ID NO 35
<211> LENGTH: 1077
<212> TYPE: DNA
<213> ORGANISM: Aegilops sharonensis
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(15)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (977)..(977)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (1003)..(1006)
<223> OTHER INFORMATION: n is a, c, g, or t
<220> FEATURE:
<221> NAME/KEY: misc_feature
<222> LOCATION: (1010)..(1017)
<223> OTHER INFORMATION: n is a, c, g, or t
<220> FEATURE:
<221> NAME/KEY: misc_feature
<222> LOCATION: (1019)..(1021)
<223> OTHER INFORMATION: n is a, c, g, or t
<220> FEATURE:
<221> NAME/KEY: misc_feature
<222> LOCATION: (1023)..(1025)
<223> OTHER INFORMATION: n is a, c, g, or t
<220> FEATURE:
<221> NAME/KEY: misc_feature
<222> LOCATION: (1027)..(1068)
<223> OTHER INFORMATION: n is a, c, g, or t
<220> FEATURE:
<221> NAME/KEY: misc_feature
<222> LOCATION: (1073)..(1073)
<223> OTHER INFORMATION: n is a, c, g, or t

<400> SEQUENCE: 35

| | | | | | |
|---|---|---|---|---|---|
| nnnnnnnnnc | nnnnnctaan | tataaggaaa | ggatcagaat | aagtactaat | gctctgtata | 60 |
| atactttttcc | ccgagcgatg | gtttagcgga | ttcggaattg | taaccaagca | tcctgggttc | 120 |
| tatacccgat | tcaacactag | agcatgcagc | cgatcctgga | tacataacta | tataaagtgt | 180 |
| gccgttttgg | atctttattg | gtagccagtc | tttcacttct | gcctctccac | tcccatgcct | 240 |
| ttcttggtcg | gaccaaccca | accggcgatt | tccgacaagt | ctttctgctt | agagcaagaa | 300 |
| gcggaaccaa | aataaagctt | tctttatttt | catttatgga | taaccaatcc | attttccaat | 360 |
| atagttggga | gattttaccc | aagaaatggg | tacataaaat | gaaaagatcg | gaacatggga | 420 |
| atagatctta | taccaatact | gactacccat | ttccattgtt | gtgctttcta | aaatggcata | 480 |
| cctatacaag | ggttcaagtt | tcgatcgata | tttgcggagt | ggatcatccc | tctcgaaaac | 540 |
| gaagatttga | agttgtccat | aatttactga | gtactcggta | taactcacgc | attcgtgtac | 600 |
| aaacaagtgc | agacgaagta | acacgaatat | ctccggtagt | cagtctattt | ccatcagccg | 660 |
| gccggtggga | gcgagaagta | tgggatatgt | ctggtgtttc | ttccatcaat | catccggatt | 720 |
| tacgccgtat | atcaacagat | tatggtttcg | agggtcatcc | attacgaaaa | gactttcctc | 780 |
| tgagtggata | tgtggaagta | cgctatgatg | atccagagaa | acgtgtggtt | tctgaaccca | 840 |
| ttgagatgac | ccaagaattt | cgctatttcg | attttgctag | tccttgggaa | cagcgtagcg | 900 |
| acggataatt | ccgaatctac | ataggtctag | tccaggggac | aaatcaatag | gaaatgctat | 960 |
| ttgcttctta | gaagaanact | nttttgaaat | gaanagttca | cgnnnngggn | nnnnnnntnn | 1020 |
| nannnannnn | nnnnnnnnnn | nnnnnnnnnn | nnnnnnnnnn | nnnnnnntt | ttntttt | 1077 |

<210> SEQ ID NO 36
<211> LENGTH: 1028
<212> TYPE: DNA
<213> ORGANISM: Aegilops sharonensis
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (1006)..(1009)
<223> OTHER INFORMATION: n is a, c, g, or t
<220> FEATURE:
<221> NAME/KEY: misc_feature
<222> LOCATION: (1012)..(1012)
<223> OTHER INFORMATION: n is a, c, g, or t
<220> FEATURE:

```
<221> NAME/KEY: misc_feature
<222> LOCATION: (1014)..(1018)
<223> OTHER INFORMATION: n is a, c, g, or t

<400> SEQUENCE: 36
nnnnnnnnnn nnanntctnn ntataaggaa ggntcagaat aagtactaat gctctgtata      60
atactttccc ccgagcgatg gtttagcgga ttcggaattg taaccaagca tcctgggttc     120
tatacccgat tcaacactag agcatgcagc cgatcctgga tacataacta tataaagtgt     180
gccgttttgg atctttattg gtagccagtc tttcacttct gcctctccac tcccatgcct     240
ttcttggtcg gaccaaccca accggcgatt tccgacaagt ctttctgctt agagcaagaa     300
gcggaaccaa aataaagctt tctttatttt catttatgga taaccaatcc attttccaat     360
atagttggga gattttaccc aagaaatggg tacataaaat gaaagatcg gaacatggga      420
atagatctta taccaatact gactacccat ttccattgtt gtgctttcta aaatggcata     480
cctatacaag ggttcaagtt tcgatcgata tttgcggagt ggatcatccc tctcgaaaac     540
gaagatttga agttgtccat aatttactga gtactcggta taactcacgc attcgtgtac     600
aaacaagtgc agacgaagta acacgaatat ctccggtagt cagtctattt ccatcagccg     660
gccggtggga gcgagaagta tgggatatgt ctggtgtttc ttccatcaat catccggatt     720
tacgccgtat atcaacagat tatggtttcg agggtcatcc attacgaaaa gactttcctc     780
tgagtggata tgtggaagta cgctatgatg atccagagaa acgtgtggtt tctgaaccca     840
ttgagatgac ccaagaattt cgctatttcg attttgctag tccttgggaa cagcgtagcg     900
acggataatt ccgaatctac ataggtctag tccaggggac aaatcaatag gaaatgctat     960
ttgcttctta agaagaagaa ctttttgaa agaaagagtt tcacgnnnng gnannnnntt    1020
ttaataaa                                                            1028

<210> SEQ ID NO 37
<211> LENGTH: 522
<212> TYPE: DNA
<213> ORGANISM: Aegilops sharonensis
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (22)..(27)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
```

```
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (257)..(258)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (443)..(444)
```

```
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (458)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (478)..(479)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (487)..(491)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (517)..(519)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t

<400> SEQUENCE: 37
nnnnnnnnnn nnnnnncnnn tnnnnnncnn nctancncna atgtcagtcn gttttctcat      60
ctcanaatca tnccnacttt tgaaatcant tgagataatg agtttggaac tggagttctt     120
gaanatctga ntgactcata cacanatcgc aacacatcaa ctggaccatc cattgagttg     180
gttggactga aacttctctg tgagagattg tagggaaccn gaaccaacac gcagctgata    240
```

| | | |
|---|---|---|
| atgagatatt tttgccnnag agcaagagat gcttcttgtc caagttgctc anctagaatc | 300 | |
| gatgaanttc ctttactttt tgacccacgg aaaanagatg aacgactttc cntttgtggg | 360 | |
| ttactgtaac aatngnatat tagtttgata tttatagaca tttatgggta gntntaaaat | 420 | |
| gnctgcntac tttcctccaa agnnacntac tcctgnannt gnananatna tccngnannt | 480 | |
| ttngntnnnn nacantccgg ggngggtaa attcccnnnt nt | 522 | |

```
<210> SEQ ID NO 38
<211> LENGTH: 1041
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1004)..(1007)
<223> OTHER INFORMATION: n is a, c, g, or t
<220> FEATURE:
<221> NAME/KEY: misc_feature
<222> LOCATION: (1009)..(1011)
<223> OTHER INFORMATION: n is a, c, g, or t
<220> FEATURE:
<221> NAME/KEY: misc_feature
<222> LOCATION: (1013)..(1017)
<223> OTHER INFORMATION: n is a, c, g, or t
<220> FEATURE:
<221> NAME/KEY: misc_feature
<222> LOCATION: (1020)..(1021)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1030)..(1040)
<223> OTHER INFORMATION: n is a, c, g, or t

<400> SEQUENCE: 38
```

```
nnnnnnnnnn ngnatctaan tatnagnnaa ggancagaat aagtactaat gctctgtata      60
atacttttcc ccgagcgatg gtttagcgga ttcggaattg taaccaagca tcctgggttc     120
tatacccgat tcaacactag agcatgcagc cgatcctgga tacataacta tataaagtgt     180
gccgttttgg atctttattg gtagccagtc tttcacttct gcctctccac tcccatgcct     240
ttcttggtcg gaccaaccca accggcgatt tccgacaagt ctttctgctt agagcaagaa     300
gcggaaccaa aataaagctt tctttatttt catttatgga taaccaatcc attttccaat     360
atagttggga gattttaccc aagaaatggg tacataaaat gaaaagatcg aacatggga      420 atagatctta taccaatact gactacccat ttccattgtt gtgctttcta aaatggcata     480
cctatacaag ggttcaagtt tcgatcgata tttgcggagt ggatcatccc tctcgaaaac     540
gaagatttga agttgtccat aatttactga gtactcggta taactcacgc attcgtgtac     600
aaacaagtgc agacgaagta acacgaatat ctccggtagt cagtctattt ccatcagccg     660
gccggtggga gcgagaagta tgggatatgt ctggtgtttc ttccatcaat catccggatt     720
tacgccgtat atcaacagat tatggtttcg agggtcatcc attacgaaaa gactttcctc     780
tgagtggata tgtggaagta cgctatgatg atccagagaa acgtgtggtt tctgaaccca     840
ttgagatgac ccaagaattt cgctatttcg attttgctag tccttgggaa cagcgtagcg     900
acggataatt ccgaatctac ataggtctag tccaggggac aaatcaatag gaaatgctat     960
ttgcttctta agaagaagaa ctntttttaaa tgaagagttc ncgnnnngnn nannnnnttn    1020
ntnanaaaan nnnnnnnnnn c                                              1041

<210> SEQ ID NO 39
<211> LENGTH: 1032
<212> TYPE: DNA
<213> ORGANISM: Aegilops sharonensis
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (1007)..(1010)
<223> OTHER INFORMATION: n is a, c, g, or t
<220> FEATURE:
<221> NAME/KEY: misc_feature
<222> LOCATION: (1012)..(1015)
<223> OTHER INFORMATION: n is a, c, g, or t
<220> FEATURE:
<221> NAME/KEY: misc_feature
<222> LOCATION: (1017)..(1020)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1030)..(1031)
<223> OTHER INFORMATION: n is a, c, g, or t

<400> SEQUENCE: 39
nnnnnnnnnn nnnntctaa tataaggaaa ggancagaat aagtactaat gctctgtata      60
atacttttcc ccgagcgatg gtttagcgga ttcggaattg taaccaagca tcctgggttc    120
```

-continued

```
tatacccgat tcaacactag agcatgcagc cgatcctgga tacataacta tataaagtgt         180
gccgttttgg atctttattg gtagccagtc tttcacttct gcctctccac tcccatgcct         240
ttcttggtcg gaccaaccca accggcgatt tccgacaagt ctttctgctt agagcaagaa         300
gcggaaccaa aataaagctt tctttatttt catttatgga taaccaatcc attttccaat         360
atagttggga gattttaccc aagaaatggg tacataaaat gaaagatcg gaacatggga          420 atagatctta taccaatact gactacccat ttccattgtt gtgctttcta aaatggcata         480
cctatacaag ggttcaagtt tcgatcgata tttgcggagt ggatcatccc tctcgaaaac         540
gaagatttga agttgtccat aatttactga gtactcggta taactcacgc attcgtgtac         600
aaacaagtgc agacgaagta acacgaatat ctccggtagt cagtctattt ccatcagccg         660
gccggtggga gcgagaagta tgggatatgt ctggtgtttc ttccatcaat catccggatt         720
tacgccgtat atcaacagat tatggtttcg agggtcatcc attacgaaaa gactttcctc         780
tgagtggata tgtggaagta cgctatgatg atccagagaa acgtgtggtt tctgaaccca         840
ttgagatgac ccaagaattt cgctatttcg attttgctag tccttgggaa cagcgtagcg         900
acggataatt ccgaatctac ataggtctag tccaggggac aaatcaatag gaaatgctat         960
ttgcttctta agaagaagaa ctttttttgaa ntaaagagtt tcacggnnnn gnnnntnnnn       1020
aaaaancccn nc                                                            1032
```

<210> SEQ ID NO 40
<211> LENGTH: 1085
<212> TYPE: DNA
<213> ORGANISM: Triticum zhukovskyi
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1012)..(1015)
<223> OTHER INFORMATION: n is a, c, g, or t
<220> FEATURE:
<221> NAME/KEY: misc_feature
<222> LOCATION: (1017)..(1025)
<223> OTHER INFORMATION: n is a, c, g, or t
<220> FEATURE:

<221> NAME/KEY: misc_feature
<222> LOCATION: (1027)..(1027)
<223> OTHER INFORMATION: n is a, c, g, or t
<220> FEATURE:
<221> NAME/KEY: misc_feature
<222> LOCATION: (1031)..(1042)
<223> OTHER INFORMATION: n is a, c, g, or t
<220> FEATURE:
<221> NAME/KEY: misc_feature
<222> LOCATION: (1044)..(1062)
<223> OTHER INFORMATION: n is a, c, g, or t
<220> FEATURE:
<221> NAME/KEY: misc_feature
<222> LOCATION: (1064)..(1072)
<223> OTHER INFORMATION: n is a, c, g, or t
<220> FEATURE:
<221> NAME/KEY: misc_feature
<222> LOCATION: (1074)..(1075)
<223> OTHER INFORMATION: n is a, c, g, or t
<220> FEATURE:
<221> NAME/KEY: misc_feature
<222> LOCATION: (1077)..(1078)
<223> OTHER INFORMATION: n is a, c, g, or t
<220> FEATURE:
<221> NAME/KEY: misc_feature
<222> LOCATION: (1080)..(1083)
<223> OTHER INFORMATION: n is a, c, g, or t

<400> SEQUENCE: 40

| | | | | | |
|---|---|---|---|---|---|
| nnnnnnnnnc | nanntctnnn | ataaggaaag | gntcagaata | agtactaatg | ctctgtataa | 60 |
| tacttttccc | cgagcgatgg | tttagcggat | tcggaattgt | aaccaagcat | cctgggttct | 120 |
| atacccgatt | caacactaga | gcatgcagcc | gatcctggat | acataactct | aaaaagtgtg | 180 |
| tgtgcagttt | tggatcttta | ttggtagcca | gtctttcact | tctgcctctc | cactcccatg | 240 |
| cctttcttgg | tcggaccaac | ccaaccggcg | atttccgaca | agtctttctg | cttagagcaa | 300 |
| gaagcggaac | caaaataaag | cttctcttat | tttcatttat | ggataaccaa | tccattttcc | 360 |
| aatatagttg | ggagatttta | cccaagaaat | gggtacataa | aatgaaaaga | tcggaacatg | 420 |
| ggaatagatc | ttataccaat | actgactacc | catttccatt | gttgtgcttt | ctaaaatggc | 480 |
| atacctatac | aagggttcaa | gtttcgatcg | atatttgcgg | agtggatcat | ccctctcgaa | 540 |
| aacgaagatt | tgaagttgtc | cataatttac | tgagtactcg | gtataactca | cgcattcgtg | 600 |
| tacaaacaag | tgcagacgaa | gtaacacgaa | tatctccggt | agtcagtcta | tttccatcag | 660 |
| ccggccggtg | ggagcgagaa | gtatgggata | tgtctggtgt | ttcttccatc | aatcatccgg | 720 |
| atttacgccg | tatatcaaca | gattatggtt | tcgagggtca | tccattacga | aaagactttc | 780 |
| ctctgagtgg | atatgtggaa | gtacgctatg | atgatccaga | gaaacgtgtg | gtttctgaac | 840 |
| ccattgagat | gacccaagaa | tttcgctatt | tcgattttgc | tagtccttgg | gaacagcgta | 900 |
| gcgacggata | attccgaatc | tacataggtc | tagtccaggg | gacaaatcaa | taggaaatgc | 960 |
| tatttgcttc | ttaanaagaa | gaacttttt | gaatgaaaag | ttcacgcgcn | gnnnnannnn | 1020 |
| nnnnntngaa | nnnnnnnnnn | nngnnnnnnn | nnnnnnnnnn | nngnnnnnnn | nntnncnngn | 1080 |
| nnngc | | | | | | 1085 |

<210> SEQ ID NO 41
<211> LENGTH: 993
<212> TYPE: DNA
<213> ORGANISM: Triticum zhukovskyi
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature

```
<222> LOCATION: (24)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (928)..(930)
<223> OTHER INFORMATION: n is a, c, g, or t
<220> FEATURE:
<221> NAME/KEY: misc_feature
<222> LOCATION: (935)..(935)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (980)..(981)
<223> OTHER INFORMATION: n is a, c, g, or t
<220> FEATURE:
<221> NAME/KEY: misc_feature
<222> LOCATION: (985)..(986)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (992)..(992)
<223> OTHER INFORMATION: n is a, c, g, or t

<400> SEQUENCE: 41
nnnnnnnnnn nnnnnntaga tctnntntaa ggaaggntca gaataagtac taatgctctg      60
tataatactt ttccccgagc gatggtttag cggattcgga attgtaacca agcatcctgg     120
gttctatacc cgattcaaca ctagagcatg cagccgatcc tggatacata actctaaaaa     180
gtgtgtgtgc agttttggat ctttattggt agccagtctt tcacttctgc ctctccactc     240
ccatgccttt cttggtcgga ccaacccaac cggcgatttc cgacaagtct ttctgcttag     300
agcaagaagc ggaaccaaaa taaagctttc tttattttca tttatggata accaatccat     360
tttccaatat agttgggaga ttttacccaa gaaatgggta cataaaatga aaagatcgga     420
acatgggaat agatcttata ccaatactga ctacccarttt ccattgttgt gctttctaaa     480
atggcatacc tatacaaggg ttcaagtttc gatcgatatt tgcggagtgg atcatccctc     540
tcgaaaacga agatttgaag ttgtccataa tttactgagt actcggtata actcacgcat     600
tcgtgtacaa acaagtgcag acgaagtaac acgaatatct ccggtagtca gtctatttcc     660
atcagccggc cggtgggagc gagaagtatg ggatatgtct ggtgtttctt ccatcaatca     720
tccggattta cgccgtatat caacagatta tggtttcgag ggtcatccat tacgaaaaga     780
```

```
ctttcctctg agtggatatg tggaagtacg ctatgatgat ccagagaaac gtgtggtttc    840
tgaacccatt gagatgaccc aagaatttcg ctatttcgat tttgctagtc cttgggaaca    900
gcgtagcgac gganaattcc gaatctannn aggtntagtc caggggganaa atcaatagga   960 aatgctnttt gcttnttagn nagannaanc tnt                                 993
```

<210> SEQ ID NO 42
<211> LENGTH: 1059
<212> TYPE: DNA
<213> ORGANISM: Triticum timopheevii
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (1005)..(1006)
<223> OTHER INFORMATION: n is a, c, g, or t
<220> FEATURE:
<221> NAME/KEY: misc_feature
<222> LOCATION: (1014)..(1024)
<223> OTHER INFORMATION: n is a, c, g, or t
<220> FEATURE:
<221> NAME/KEY: misc_feature
<222> LOCATION: (1030)..(1034)
<223> OTHER INFORMATION: n is a, c, g, or t
<220> FEATURE:
<221> NAME/KEY: misc_feature
<222> LOCATION: (1037)..(1039)
<223> OTHER INFORMATION: n is a, c, g, or t
<220> FEATURE:
<221> NAME/KEY: misc_feature
<222> LOCATION: (1045)..(1045)
<223> OTHER INFORMATION: n is a, c, g, or t
<220> FEATURE:
<221> NAME/KEY: misc_feature
<222> LOCATION: (1048)..(1048)
<223> OTHER INFORMATION: n is a, c, g, or t
<220> FEATURE:
<221> NAME/KEY: misc_feature
<222> LOCATION: (1050)..(1053)
<223> OTHER INFORMATION: n is a, c, g, or t
<220> FEATURE:
<221> NAME/KEY: misc_feature
<222> LOCATION: (1056)..(1058)
<223> OTHER INFORMATION: n is a, c, g, or t

<400> SEQUENCE: 42

```
nnnnnnnncn nnnnctnnna taaggnngga ncagaataag tactaatgct ctgtataata    60
cttttccccg agcgatggtt tagcggattc ggaattgtaa ccaagcatcc tgggttctat    120
acccgattca acactagagc atgcagccga tcctggatac ataactctaa aaagtgtgtg   180
tgcagttttg gatctttatt ggtagccagt ctttcacttc tgcctctcca ctcccatgcc   240
```

```
tttcttggtc ggaccaaccc aaccggcgat ttccgacaag tctttctgct tagagcaaga    300
agcggaacca aaataaagct ttctttattt tcatttatgg ataaccaatc cattttccaa    360
tatagttggg agattttacc caagaaatgg gtacataaaa tgaaaagatc ggaacatggg    420
aatagatctt ataccaatac tgactaccca tttccattgt tgtgctttct aaaatggcat    480
acctatacaa gggttcaagt ttcgatcgat atttgcggag tggatcatcc ctctcgaaaa    540
cgaagatttg aagttgtcca taatttactg agtactcggt ataactcacg cattcgtgta    600
caaacaagtg cagacgaagt aacacgaata tctccggtag tcagtctatt tccatcagcc    660
ggccggtggg agcgagaagt atgggatatg tctggtgttt cttccatcaa tcatccggat    720
ttacgccgta tatcaacaga ttatggtttc gagggtcatc cattacgaaa agactttcct    780
ctgagtggat atgtggaagt acgctatgat gatccagaga aacgtgtggt ttctgaaccc    840
attgagatga cccaagaatt tcgctatttc gattttgcta gtccttggga acagcgtagc    900
gacggataat tccgaatcta cataggtcta gtccagggga caaatcaata ggaaatgcta    960
tttgcttctt aagaagaaga acttttttng aatgaaagag ttccnnggcg ccgnnnnnnn   1020
nnnnaaaaan nnnncgnnnc tctantantn nnntannnt                         1059
```

<210> SEQ ID NO 43
<211> LENGTH: 1071
<212> TYPE: DNA
<213> ORGANISM: Triticum aestivum
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (1007)..(1007)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
<221> NAME/KEY: misc_feature
<222> LOCATION: (1015)..(1034)
<223> OTHER INFORMATION: n is a, c, g, or t
<220> FEATURE:
<221> NAME/KEY: misc_feature
<222> LOCATION: (1037)..(1037)
<223> OTHER INFORMATION: n is a, c, g, or t
<220> FEATURE:
<221> NAME/KEY: misc_feature
<222> LOCATION: (1040)..(1040)
<223> OTHER INFORMATION: n is a, c, g, or t
<220> FEATURE:
<221> NAME/KEY: misc_feature
<222> LOCATION: (1045)..(1047)
<223> OTHER INFORMATION: n is a, c, g, or t
<220> FEATURE:
<221> NAME/KEY: misc_feature
<222> LOCATION: (1049)..(1050)
<223> OTHER INFORMATION: n is a, c, g, or t
<220> FEATURE:

```
<221> NAME/KEY: misc_feature
<222> LOCATION: (1052)..(1056)
<223> OTHER INFORMATION: n is a, c, g, or t
<220> FEATURE:
<221> NAME/KEY: misc_feature
<222> LOCATION: (1060)..(1070)
<223> OTHER INFORMATION: n is a, c, g, or t

<400> SEQUENCE: 43
nnnnnnnnnc nanntctaaa tataaggaag gancagaata agtactaatg ctctgtataa      60
tactttccc cgagcgatgg tttagcggat tcggaattgt aaccaagcat cctgggttct     120
atacccgatt caacactaga gcatgcagcc gatcctggat acataactct aaaaagtgtg     180
tgtgcagttt tggatcttta ttggtagcca gtctttcact tctgcctctc cactcccatg     240
cctttcttgg tcggaccaac ccaaccggcg atttccgaca agtctttctg cttagagcaa     300
gaagcggaac caaaataaag ctttctttat tttcatttat ggataaccaa tccattttcc     360
aatatagttg ggagatttta cccaagaaat gggtacataa aatgaaaaga tcggaacatg     420
ggaatagatc ttataccaat actgactacc catttccatt gttgtgcttt ctaaaatggc     480
atacctatac aagggttcaa gtttcgatcg atatttgcgg agtggatcat ccctctcgaa     540
aacgaagatt tgaagttgtc cataaatttac tgagtactcg gtataactca cgcattcgtg     600
tacaaacaag tgcagacgaa gtaacacgaa tatctccggt agtcagtcta tttccatcag     660
ccggccggtg ggagcgagaa gtatgggata tgtctggtgt ttcttccatc aatcatccgg     720
atttacgccg tatatcaaca gattatggtt tcgagggtca tccattacga aaagactttc     780
ctctgagtgg atatgtggaa gtacgctatg atgatccaga gaaacgtgtg gtttctgaac     840
ccattgagat gacccaagaa tttcgctatt tcgattttgc tagtccttgg gaacagcgta     900
gcgacggata attccgaatc tacataggtc tagtccaggg gacaaatcaa taggaaatgc     960
tatttgcttc ttaagaagaa gaactttttt gaaatgaaag agttccnggc tanannnnnn    1020
nnnnnnnnnn nnnacnctn atcannnann gnnnnncccn nnnnnnnnnn g              1071

<210> SEQ ID NO 44
<211> LENGTH: 1055
<212> TYPE: DNA
<213> ORGANISM: x Triticosecale
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (1009)..(1011)
<223> OTHER INFORMATION: n is a, c, g, or t
<220> FEATURE:
<221> NAME/KEY: misc_feature
<222> LOCATION: (1015)..(1017)
<223> OTHER INFORMATION: n is a, c, g, or t
<220> FEATURE:
<221> NAME/KEY: misc_feature
<222> LOCATION: (1020)..(1026)
<223> OTHER INFORMATION: n is a, c, g, or t
```

<220> FEATURE:
<221> NAME/KEY: misc_feature
<222> LOCATION: (1030)..(1031)
<223> OTHER INFORMATION: n is a, c, g, or t
<220> FEATURE:
<221> NAME/KEY: misc_feature
<222> LOCATION: (1033)..(1035)
<223> OTHER INFORMATION: n is a, c, g, or t
<220> FEATURE:
<221> NAME/KEY: misc_feature
<222> LOCATION: (1037)..(1038)
<223> OTHER INFORMATION: n is a, c, g, or t
<220> FEATURE:
<221> NAME/KEY: misc_feature
<222> LOCATION: (1042)..(1045)
<223> OTHER INFORMATION: n is a, c, g, or t
<220> FEATURE:
<221> NAME/KEY: misc_feature
<222> LOCATION: (1049)..(1049)
<223> OTHER INFORMATION: n is a, c, g, or t
<220> FEATURE:
<221> NAME/KEY: misc_feature
<222> LOCATION: (1052)..(1054)
<223> OTHER INFORMATION: n is a, c, g, or t

<400> SEQUENCE: 44

```
nnnnnnnnnc nanntctnnn ataaggaaag gatcagaata agtactaatg ctctgtataa      60
tactttccc cgagcgatgg tttagcggat tcggaattgt aaccaagcat cctgggttct      120
atacccgatt caacactaga gcatgcagcc gatcctggat acataactct aaaaagtgtg     180
tgtgcagttt tggatcttta ttggtagcca gtctttcact tctgcctctc cactcccatg    240
cctttcttgg tcggaccaac ccaaccggcg atttccgaca agtctttctg cttagagcaa    300
gaagcggaac caaaataaag ctttctttat tttcatttat ggataaccaa tccatttcc     360
aatatagttg ggagatttta cccaagaaat gggtacataa aatgaaaaga tcggaacatg    420
ggaatagatc ttataccaat actgactacc catttccatt gttgtgcttt ctaaaatggc    480
atacctatac aagggttcaa gtttcgatcg atatttgcgg agtggatcat ccctctcgaa    540
aacgaagatt tgaagttgtc cataatttac tgagtactcg gtataactca cgcattcgtg    600
tacaaacaag tgcagacgaa gtaacacgaa tatctccggt agtcagtcta tttccatcag    660
ccggccggtg ggagcgagaa gtatgggata tgtctggtgt ttcttccatc aatcatccgg    720
atttacgccg tatatcaaca gattatggtt tcgagggtca tccattacga aaagactttc    780
ctctgagtgg atatgtggaa gtacgctatg atgatccaga gaaacgtgtg gtttctgaac    840
ccattgagat gacccaagaa tttcgctatt tcgattttgc tagtccttgg gaacagcgta    900
gcgacggata attccgaatc tacataggtc tagtccaggg gacaaatcaa taggaaatgc    960
tatttgcttc ttaagaagaa gaactttttt gaatgaaaga gttcacgcnn ngggnnnatn   1020
nnnnnntaan ncnnngnntt gnnnnatana tnnna                               1055
```

<210> SEQ ID NO 45
<211> LENGTH: 1054
<212> TYPE: DNA
<213> ORGANISM: x Triticosecale
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)

```
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (1001)..(1002)
<223> OTHER INFORMATION: n is a, c, g, or t
<220> FEATURE:
<221> NAME/KEY: misc_feature
<222> LOCATION: (1013)..(1025)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1031)..(1032)
<223> OTHER INFORMATION: n is a, c, g, or t
<220> FEATURE:
<221> NAME/KEY: misc_feature
<222> LOCATION: (1034)..(1038)
<223> OTHER INFORMATION: n is a, c, g, or t
<220> FEATURE:
<221> NAME/KEY: misc_feature
<222> LOCATION: (1040)..(1050)
<223> OTHER INFORMATION: n is a, c, g, or t

<400> SEQUENCE: 45
nnnnnnnnnn nctagancna atataaggaa ggntcagant aagtactaat gctctgtata      60
atactttcc ccgagcgatg gtttagcgga ttcggaattg taaccaagca tcctgggttc      120
tatacccgat tcaacactag agcatgcagc cgatcctgga tacataactc taaaaagtgt    180
gtgtgcagtt ttggatcttt attggtagcc agtctttcac ttctgcctct ccactcccat    240
gcctttcttg gtcggaccaa cccaaccggc gatttccgac aagtctttct gcttagagca    300
agaagcggaa ccaaaataaa gctttcttta ttttcattta tggataacca atccattttc    360
caatatagtt gggagatttt acccaagaaa tgggtacata aaatgaaaag atcggaacat    420
gggaatagat cttataccaa tactgactac ccatttccat tgttgtgctt tctaaaatgg    480
cataccttata caagggttca agtttcgatc gatatttgcg gagtggatca tccctctcga    540
aaacgaagat ttgaagttgt ccataattta ctgagtactc ggtataactc acgcattcgt    600
gtacaaacaa gtgcagacga agtaacacga atatctccgg tagtcagtct atttccatca    660
gccggccggt gggagcgaga agtatgggat atgtctggtg tttcttccat caatcatccg    720
gatttacgcc gtatatcaac agattatggt ttcgagggtc atccattacg aaaagacttt    780
cctctgagtg gatatgtgga agtacgctat gatgatccag agaaacgtgt ggtttctgaa    840
cccattgaga tgacccaaga atttcgctat ttcgattttg ctagtccttg ggaacagcgt    900
agcgacggat aattccgaat ctacataggt ctagtccagg ggacaaatca ataggaaatg    960
ctatttgctt cttaagaaga agaactttt  tgaaatgaaa nnttccacgg ctnnnnnnn     1020
nnnnnagana nngnnnnntn nnnnnnnnnn caaa                                 1054

<210> SEQ ID NO 46
<211> LENGTH: 318
<212> TYPE: DNA
<213> ORGANISM: x Triticosecale
<220> FEATURE:
<221> NAME/KEY: misc_feature
```

```
<222> LOCATION: (1)..(25)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (49)..(51)
<223> OTHER INFORMATION: n is a, c, g, or t
<220> FEATURE:
<221> NAME/KEY: misc_feature
<222> LOCATION: (54)..(62)
<223> OTHER INFORMATION: n is a, c, g, or t
<220> FEATURE:
<221> NAME/KEY: misc_feature
<222> LOCATION: (66)..(72)
<223> OTHER INFORMATION: n is a, c, g, or t
<220> FEATURE:
<221> NAME/KEY: misc_feature
<222> LOCATION: (74)..(83)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (96)..(97)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (116)..(118)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(124)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
```

```
<221> NAME/KEY: misc_feature
<222> LOCATION: (149)..(151)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (259)..(260)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
```

<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t
<220> FEATURE:
<221> NAME/KEY: misc_feature
<222> LOCATION: (311)..(311)
<223> OTHER INFORMATION: n is a, c, g, or t

<400> SEQUENCE: 46

```
nnnnnnnnnn nnnnnnnnnn nnnnttnnt nnnnnntnan gnncggnann ngtnnnnnnn    60
nnaatnnnnn nnannnnnnn nnnggnttgg atttgnnttg nnattggtat tnngannngn   120
annncantga gcactagaga gagagnntnn ncnggttnct naattttta aagngtnggt    180
ntgtgttacg cgactggnag ntangaggnc nggcanccctc tccncnccna tgcntttctt  240
ggtcgggccn accctaccnn ataatnccga caanttttc ttntttnncna tttttttgnc   300
tnnaaataac ncccccctt                                                318
```

<210> SEQ ID NO 47
<211> LENGTH: 1058
<212> TYPE: DNA
<213> ORGANISM: x Triticosecale
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (978)..(980)
<223> OTHER INFORMATION: n is a, c, g, or t
<220> FEATURE:
<221> NAME/KEY: misc_feature
<222> LOCATION: (1000)..(1001)
<223> OTHER INFORMATION: n is a, c, g, or t
<220> FEATURE:
<221> NAME/KEY: misc_feature
<222> LOCATION: (1013)..(1025)
<223> OTHER INFORMATION: n is a, c, g, or t
<220> FEATURE:
<221> NAME/KEY: misc_feature
<222> LOCATION: (1031)..(1031)

```
<223> OTHER INFORMATION: n is a, c, g, or t
<220> FEATURE:
<221> NAME/KEY: misc_feature
<222> LOCATION: (1033)..(1033)
<223> OTHER INFORMATION: n is a, c, g, or t
<220> FEATURE:
<221> NAME/KEY: misc_feature
<222> LOCATION: (1037)..(1037)
<223> OTHER INFORMATION: n is a, c, g, or t
<220> FEATURE:
<221> NAME/KEY: misc_feature
<222> LOCATION: (1045)..(1049)
<223> OTHER INFORMATION: n is a, c, g, or t
<220> FEATURE:
<221> NAME/KEY: misc_feature
<222> LOCATION: (1053)..(1057)
<223> OTHER INFORMATION: n is a, c, g, or t

<400> SEQUENCE: 47
nnnnnnnnnn cnnnntctna atataaggaa ggancagaat aagtactaat gctctgtata      60
atactttcc ccgagcgatg gtttagcgga ttcggaattg taaccaagca tcctgggttc      120
tatacccgat tcaacactag agcatgcagc cgatcctgga tacataactc taaaaagtgt     180
gtgtgcagtt ttggatcttt attggtagcc agtctttcac ttctgcctct ccactcccat     240
gcctttcttg gtcggaccaa cccaaccggc gatttccgac aagtctttct gcttagagca     300
agaagcggaa ccaaaataaa gctttctta ttttcattta tggataacca atccattttc      360
caatatagtt gggagatttt acccaagaaa tgggtacata aaatgaaaag atcggaacat     420
gggaatagat cttataccaa tactgactac ccatttccat tgttgtgctt tctaaaatgg     480
catacctata caagggttca gtttcgatc gatatttgcg gagtggatca tccctctcga      540
aaacgaagat ttgaagttgt ccataattta ctgagtactc ggtataactc acgcattcgt     600
gtacaaacaa gtgcagacga agtaacacga atatctccgg tagtcagtct atttccatca     660
gccggccggt gggagcgaga agtatgggat atgtctggtg tttcttccat caatcatccg     720
gatttacgcc gtatatcaac agattatggt ttcgagggtc atccattacg aaaagacttt     780
cctctgagtg gatatgtgga agtacgctat gatgatccag agaaacgtgt ggtttctgaa     840
cccattgaga tgacccaaga atttcgctat ttcgattttg ctagtccttg ggaacagcgt     900
agcgacggat aattccgaat ctacataggt ctagtccagg ggacaaatca ataggaaatg     960
ctatttgctt cttaagannn agaacttttt tgaaatgaan nagtttcacg gcnnnnnnnn     1020
nnnnnttaaa ntnattnttt ttttnnnnnt ttnnnnna                             1058

<210> SEQ ID NO 48
<211> LENGTH: 1040
<212> TYPE: DNA
<213> ORGANISM: x Triticosecale
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
```

```
<222> LOCATION: (999)..(1000)
<223> OTHER INFORMATION: n is a, c, g, or t
<220> FEATURE:
<221> NAME/KEY: misc_feature
<222> LOCATION: (1006)..(1007)
<223> OTHER INFORMATION: n is a, c, g, or t
<220> FEATURE:
<221> NAME/KEY: misc_feature
<222> LOCATION: (1010)..(1014)
<223> OTHER INFORMATION: n is a, c, g, or t
<220> FEATURE:
<221> NAME/KEY: misc_feature
<222> LOCATION: (1016)..(1026)
<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t
<220> FEATURE:
<221> NAME/KEY: misc_feature
<222> LOCATION: (1032)..(1035)
<223> OTHER INFORMATION: n is a, c, g, or t
<220> FEATURE:
<221> NAME/KEY: misc_feature
<222> LOCATION: (1037)..(1038)
<223> OTHER INFORMATION: n is a, c, g, or t

<400> SEQUENCE: 48
nnnnnnnnnn cnnnnntctn nnataaggaa aggntcagaa taagtactaa tgctctgtat      60
aatactttc  cccgagcgat ggtttagcgg attcggaatt gtaaccaagc atcctgggtt     120
ctatacccga ttcaacacta gagcatgcag ccgatcctgg atacatcact atataaagtg     180
tgcatgcagt tttggatctt tattggtagc cagtctttca cttctgcctc tccactccca     240
tgcctttctt ggtcggacca acccaaccgg cgatttccga caagtctttc tgcttagagc     300
aagaagcgga accaaaataa agctttcttt atttgcattt atggataacc aatccatttt     360
ccaatatagt tgggagattt tacccaagaa atgggtacat aaaatgaaaa gatcggaaca     420
tgggaataga tcttatacca atactgacta cccatttcca ttgttgtgct ttctaaaatg     480
gcatacctat acaagggttc aagtttcgat cgatatttgc ggagtggatc atccctctcg     540
aaaacgaaga tttgaagttg tccataattt actgagtact cggtataact cacgcattcg     600
tgtacaaaca agtgcagacg aagtaacacg aatatctccg gtagtcagtc tatttccatc     660
agccggccgg tgggagcgag aagtatggga tatgtctggt gtttcttcca tcaatcatcc     720
ggatttacgc cgtatatcaa cagattatgg tttcgagggt catccattac gaaaagactt     780
tcctctgagt ggatatgtgg aagtacgcta tgatgatcca gagaaacgtg tggtttctga     840
acccattgag atgacccaag aatttcgcta tttcgatttt gctagtcctt gggaacagcg     900
tagcgacgga taattccgaa tctacatagg tctagtccag gggacaaatc aataggaaat     960
gctatttgct tctaagaaga agaacttttt tgaatgaann agttcnncgn nnngnnnnn    1020
nnnnnnaaan annnncnncc                                                1040

<210> SEQ ID NO 49
<211> LENGTH: 552
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
```

<221> NAME/KEY: misc_feature
<222> LOCATION: (19)..(19)
<223> OTHER INFORMATION: n is a, c, g, or t

<400> SEQUENCE: 49

| | | | | | |
|---|---|---|---|---|---|
| nnnnnnnnnn | ntnntttgnt | ttctctgaca | ttccatgttt | ccgaaacgga | tcctataaaa | 60 |
| tatttcactt | tttctatgat | catctctatt | ttaggtattc | ggggaatcct | ccttaataga | 120 |
| cgaaatattc | ttattatgtc | aatgccaatt | gaatcaatgt | tattagctgt | caatttgaac | 180 |
| tttttggtat | tttccgtttc | tttggatgat | atgatgggtc | aatcatttgc | ttcattagtt | 240 |
| ccaacagtgg | cagctgcgga | atctgctatt | ggattagcca | ttttcgttat | tacttttcga | 300 |
| gtccgaggga | ctattgctgt | cgaatctata | aattgcattc | aaggttaaac | ataactacag | 360 |
| gagagttacc | aaatacaaag | ttctgttctc | ctttcgttct | cttctttctt | ttcttttttgc | 420 |
| ctgagtcaga | catcaaatag | cttcgatttg | cattatccgt | tggaatgtat | caaaatcaat | 480 |
| atcaaaatca | ataagatgaa | agatgtacaa | tccaatttct | cgattcaata | gaagcccaag | 540 |
| gaggtgcaaa | tt | | | | | 552 |

<210> SEQ ID NO 50
<211> LENGTH: 548
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 50

| | | | | | |
|---|---|---|---|---|---|
| nnnnnnnnnn | naatttgant | tctctgacat | tccatgtttc | cgaaacggat | cctataaaat | 60 |
| atttcactt | ttctatgatc | atctctattt | aggtattcg | gggaatcctc | cttaatagac | 120 |
| gaaatattct | tattatgtca | atgccaattg | aatcaatgtt | attagctgtc | aatttgaact | 180 |
| ttttggtatt | ttccgtttct | tggatgata | tgatgggtca | atcatttgct | tcattagttc | 240 |
| caacagtggc | agctgcggaa | tctgctattg | gattagccat | tttcgttatt | acttttcgag | 300 |
| tccgagggac | tattgctgtc | gaatctataa | attgcattca | aggttaaaca | taactacagg | 360 |
| agagttacca | aatacaaagt | tctgttctcc | tttcgttctc | ttctttcttt | tcttttttgcc | 420 |
| tgagtcagac | atcaaatagc | ttcgatttgc | attatccgtt | ggaatgtatc | aaaatcaata | 480 |
| tcaaaatcaa | taagatgaaa | gatgtacaat | ccaatttctc | gattcaatag | aagcccaagg | 540 |
| aaggtgca | | | | | | 548 |

<210> SEQ ID NO 51
<211> LENGTH: 791
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t -continued

```
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (525)..(527)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (553)..(554)
<223> OTHER INFORMATION: n is a, c, g, or t
<220> FEATURE:
<221> NAME/KEY: misc_feature
<222> LOCATION: (583)..(584)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (596)..(598)
<223> OTHER INFORMATION: n is a, c, g, or t
<220> FEATURE:
<221> NAME/KEY: misc_feature
<222> LOCATION: (609)..(610)
<223> OTHER INFORMATION: n is a, c, g, or t
<220> FEATURE:
<221> NAME/KEY: misc_feature
<222> LOCATION: (614)..(616)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (628)..(630)
<223> OTHER INFORMATION: n is a, c, g, or t
<220> FEATURE:
<221> NAME/KEY: misc_feature
<222> LOCATION: (635)..(637)
<223> OTHER INFORMATION: n is a, c, g, or t
<220> FEATURE:
<221> NAME/KEY: misc_feature
<222> LOCATION: (652)..(654)
<223> OTHER INFORMATION: n is a, c, g, or t
<220> FEATURE:
<221> NAME/KEY: misc_feature
<222> LOCATION: (669)..(674)
<223> OTHER INFORMATION: n is a, c, g, or t
<220> FEATURE:
<221> NAME/KEY: misc_feature
<222> LOCATION: (678)..(680)
<223> OTHER INFORMATION: n is a, c, g, or t
<220> FEATURE:
<221> NAME/KEY: misc_feature
<222> LOCATION: (684)..(684)
```

```
<223> OTHER INFORMATION: n is a, c, g, or t
<220> FEATURE:
<221> NAME/KEY: misc_feature
<222> LOCATION: (686)..(688)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (699)..(703)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (712)..(712)
<223> OTHER INFORMATION: n is a, c, g, or t
<220> FEATURE:
<221> NAME/KEY: misc_feature
<222> LOCATION: (714)..(718)
<223> OTHER INFORMATION: n is a, c, g, or t
<220> FEATURE:
<221> NAME/KEY: misc_feature
<222> LOCATION: (725)..(733)
<223> OTHER INFORMATION: n is a, c, g, or t
<220> FEATURE:
<221> NAME/KEY: misc_feature
<222> LOCATION: (737)..(745)
<223> OTHER INFORMATION: n is a, c, g, or t
<220> FEATURE:
<221> NAME/KEY: misc_feature
<222> LOCATION: (753)..(758)
<223> OTHER INFORMATION: n is a, c, g, or t
<220> FEATURE:
<221> NAME/KEY: misc_feature
<222> LOCATION: (761)..(767)
<223> OTHER INFORMATION: n is a, c, g, or t
<220> FEATURE:
<221> NAME/KEY: misc_feature
<222> LOCATION: (769)..(774)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t

<400> SEQUENCE: 51
nnnnnnnnnn natttgnttt ctctgacatt ccatgtttcc gaaacggatc ctataaaata      60
tttcactttt tctatgatca tctctatttt aggtattcgg ggaatcctcc ttaatagacg     120
aaatattctt attatgtcaa tgccaattga atcaatgtta ttagctgtca atttgaactt     180
tttggtattt tccgtttctt tggatgatat gatgggtcaa tcatttgctt cattagttcc     240
aacagtggca gctgcggaat ctgctattgg attagccatt ttcgttatta cttttcgagt     300
ccgagggact attgctgtcn gaatctataa attgcatttc aagggttaaa acataaacta     360
cagggagaag ttaccnaaat accaaaagtt tctgtttctc ccttttcggt tcctccttcc     420 tttcctttt cctttttttg cccttgaagt tcagaaaaca ttccaaaatt aagcctttcc     480
gaatttttgg ccantttaat tccccggttt ggggaaaatt ggttnnntcc naaaaaaatt     540
ccnaaattta ntnnaaaaaa atttcccaaa tttaaaaagg aanntggnaa aaaaannnaa     600
attgggttnn accnnnaaan ntnncccnnn aaaannnttt ttttttccct tnnccggga     660 aaatttttnn nnnnaaannn tttntnnngn naaaaaaann nnccnccnc cncnnnnnaa     720
```
aaaannnnnn nnnaaannnn nnnnnggggg ggnnnnnntt nnnnnnncnn nnnnaaaaaa    780
aaaaanaaaa a                                                         791

<210> SEQ ID NO 52
<211> LENGTH: 552
<212> TYPE: DNA
<213> ORGANISM: Aegilops sharonensis
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (550)..(551)
<223> OTHER INFORMATION: n is a, c, g, or t

<400> SEQUENCE: 52
nnnnnnnnnn ntnntttgat ttctctgaca ttccatgttt ccgaaacgga tcctataaaa    60
tatttcactt tttctatgat catctctatt ttaggtattc ggggaatcct ccttaataga    120
cgaaatattc ttattatgtc aatgccaatt gaatcaatgt tattagctgt caatttgaac    180
tttttggtat tttccgtttc tttggatgat atgatgggtc aatcatttgc ttcattagtt    240
ccaacagtgg cagctgcgga atctgctatt ggattagcca ttttcgttat tacttttcga    300
gtccgaggga ctattgctgt cgaatctata aattgcattc aaggttaaac ataactacag    360
gagagttacc aaatacaaag ttctgttctc ctttcgttct cttctttctt ttcttttttgc   420 ctgagtcaga catcaaatag cttcgatttg cattatccgt tggaatgtat caaaatcaat    480
atcaaaatca ataagatgaa agatgtacaa tccaatttct cgattcaata gaagcccagg    540
aaggtgcaan na                                                        552

<210> SEQ ID NO 53
<211> LENGTH: 478
<212> TYPE: DNA
<213> ORGANISM: Aegilops sharonensis
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t
<220> FEATURE:
<221> NAME/KEY: misc_feature
<222> LOCATION: (22)..(26)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (39)..(42)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:

<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (349)..(350)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
<221> NAME/KEY: misc_feature
<222> LOCATION: (439)..(440)
<223> OTHER INFORMATION: n is a, c, g, or t
<220> FEATURE:
<221> NAME/KEY: misc_feature
<222> LOCATION: (460)..(464)
<223> OTHER INFORMATION: n is a, c, g, or t
<220> FEATURE:
<221> NAME/KEY: misc_feature
<222> LOCATION: (468)..(470)
<223> OTHER INFORMATION: n is a, c, g, or t
<220> FEATURE:
<221> NAME/KEY: misc_feature
<222> LOCATION: (473)..(477)
<223> OTHER INFORMATION: n is a, c, g, or t

<400> SEQUENCE: 53
nnnnnnnnnn tnnnnnnnnt cnnnnncaac actanatcnn nngtcagtcn gttttctcat      60
ctcntactcn tnctnctnnn nactcanttg agataaagag tttggaactg gagttcatga     120
acatctgagt gactcataca cagatctaca cacatcaact ggaccatcca ttgagttggt     180
tggactgaag cttctctgtg agagattgta tggagccgga nccaaancgc agctcataat     240
gagatatttt tgccanagac caagacatgc ttcttgtcca agttgctcnc ctagaatcga     300

```
tgaanttcct ttacttttg acccacagaa aaaagatgaa ctactttcnn tttgtgggtt      360
actgtaacaa tagaatatta gtttgatatt tatagacatt tatgggtagg tataaaatgg      420
ctgcntncat tcctccaann cgacttactc ctgtacatgn nnnaatnnn atnnnnnt         478
```

<210> SEQ ID NO 54
<211> LENGTH: 558
<212> TYPE: DNA
<213> ORGANISM: Aegilops sharonensis
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t

<400> SEQUENCE: 54

```
nnnnnnnnnn nnctnntatt tgatttctct gacattccat gtttccgaaa cggatcctat      60
aaaatatttc actttttcta tgatcatctc tattttaggt attcggggaa tcctccttaa     120
tagacgaaat attcttatta tgtcaatgcc aattgaatca atgttattag ctgtcaattt     180
gaactttttg gtatttccg tttctttgga tgatatgatg ggtcaatcat ttgcttcatt     240
agttccaaca gtggcagctg cggaatctgc tattggatta gccatttcg ttattacttt     300 tcgagtccga gggactattg ctgtcgaatc tataaattgc attcaaggtt aaacataact     360
acaggagagt taccaaatac aaagttctgt tctcctttcg ttctcttctt tcttttcttt     420
ttgcctgagt cagacatcaa atagcttcga tttgcattat ccgttggaat gtatcaaaat     480
caatatcaaa atcaataaga tgaaagatgt acaatccaat ttctcgattc aatagaagcc     540
caaggaaggt gcnanana                                                   558
```

<210> SEQ ID NO 55
<211> LENGTH: 552
<212> TYPE: DNA
<213> ORGANISM: Aegilops sharonensis
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t

<400> SEQUENCE: 55

```
nnnnnnnnnn nnnatttgat ttctctgaca ttccatgttt ccgaaacgga tcctataaaa      60
tatttcactt tttctatgat catctctatt ttaggtattc ggggaatcct ccttaataga    120
cgaaatattc ttattatgtc aatgccaatt gaatcaatgt tattagctgt caatttgaac    180 ttttggtat tttccgtttc tttggatgat atgatgggtc aatcatttgc ttcattagtt    240
```

```
ccaacagtgg cagctgcgga atctgctatt ggattagcca ttttcgttat tactttcga       300 gtccgaggga ctattgctgt cgaatctata aattgcattc aaggttaaac ataactacag       360
gagagttacc aaatacaaag ttctgttctc ctttcgttct cttctttctt ttcttttgc       420 ctgagtcaga catcaaatag cttcgatttg cattatccgt tggaatgtat caaaatcaat       480
atcaaaatca ataagatgaa agatgtacaa tccaatttct cgattcaata gaagcccaag       540
aaggtgcaan aa                                                           552
```

<210> SEQ ID NO 56
<211> LENGTH: 557
<212> TYPE: DNA
<213> ORGANISM: Triticum zhukovskyi
<220> FEATURE:
<221> NAME/KEY: misc_feature
<222> LOCATION: (1)..(18)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (73)..(75)
<223> OTHER INFORMATION: n is a, c, g, or t

<400> SEQUENCE: 56

```
nnnnnnnnnn nnnnnnnntt gatttctctg acantccatg tttccgaaac ggatcctata        60
aaatatttca ctnnntctat gatcatctct attttaggta ttcggggaat cctccttaat       120
agacgaaata ttcttattat gtcaatgcca attgaatcaa tgttattagc tgtcaatttg       180
aactttttgg tattttccgt ttctttggat gatatgatgg gtcaatcatt tgcttcatta       240
gttccaacag tggcagctgc ggaatctgct attggattag ccattttcgt tattactttt       300
cgagtccgag ggactattgc tgtcgaatct ataaattgca ttcaaggtta aacataacta       360
caggagagtt accaaataca aagttctgtt ctcctttcgt tctcttcttt cttttctttt       420
tgcctgagtc agacatcaaa tagcttcgat ttgcattatc cgttggaatg tatcaaaatc       480
aatatcaaaa tcaataagat gaaagatgta caatccaatt tctcgattca atagaagccc       540
aaggaggtgc aaaaata                                                      557
```

<210> SEQ ID NO 57
<211> LENGTH: 555
<212> TYPE: DNA
<213> ORGANISM: Triticum zhukovskyi
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t

<400> SEQUENCE: 57

```
nnnnnnnnnn nnnnnanttg ntttctctga cattccatgt ttccgaaacg gatcctataa    60
aatatttcac tttttctatg atcatctcta ttttaggtat tcggggaatc ctccttaata   120
gacgaaatat tcttattatg tcaatgccaa ttgaatcaat gttattagct gtcaatttga   180 acttttggt attttccgtt tctttggatg atatgatggg tcaatcattt gcttcattag    240
ttccaacagt ggcagctgcg gaatctgcta ttggattagc cattttcgtt attacttttc   300
gagtccgagg gactattgct gtcgaatcta taaattgcat tcaaggttaa acataactac   360
aggagagtta ccaaatacaa agttctgttc tcctttcgtt ctcttcttc ttttcttttt    420 gcctgagtca gacatcaaat agcttcgatt tgcattatcc gttggaatgt atcaaaatca   480
atatcaaaat caataagatg aaagatgtac aatccaattt ctcgattcaa tagaagccca   540
aggaggtgca nttna                                                    555
```

<210> SEQ ID NO 58
<211> LENGTH: 553
<212> TYPE: DNA
<213> ORGANISM: Triticum timopheevii
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t

<400> SEQUENCE: 58

```
nnnnnnnnnn nnnntttgnt ttctctgaca ttccatgttt ccgaaacgga tcctataaaa    60
tatttcactt tttctatgat catctctatt ttaggtattc ggggaatcct ccttaataga   120
cgaaatattc ttattatgtc aatgccaatt gaatcaatgt tattagctgt caatttgaac   180
tttttggtat tttccgtttc tttggatgat atgatgggtc aatcatttgc ttcattagtt   240
ccaacagtgg cagctgcgga atctgctatt ggattagcca ttttcgttat tactttcga   300 gtccgaggga ctattgctgt cgaatctata aattgcattc aaggttaaac ataactacag   360
gagagttacc aaatacaaag ttctgttctc ctttcgttct cttctttctt ttcttttgc    420 ctgagtcaga catcaaatag cttcgatttg cattatccgt tggaatgtat caaaatcaat   480
atcaaaatca ataagatgaa agatgtacaa tccaatttct cgattcaata gaagcccaag   540
gaggtgcaan aag                                                      553
```

<210> SEQ ID NO 59
<211> LENGTH: 555
<212> TYPE: DNA
<213> ORGANISM: Triticum aestivum
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t

<400> SEQUENCE: 59

```
nnnnnnnnnn nnnnnntttg atttctctga cattccatgt ttccgaaacg gatcctataa    60
```

```
aatatttcac tttttctatg atcatctcta ttttaggtat tcggggaatc ctccttaata    120
gacgaaatat tcttattatg tcaatgccaa ttgaatcaat gttattagct gtcaatttga    180 acttttggt attttccgtt tctttggatg atatgatggg tcaatcattt gcttcattag    240
ttccaacagt ggcagctgcg gaatctgcta ttggattagc cattttcgtt attacttttc    300
gagtccgagg gactattgct gtcgaatcta taaattgcat tcaaggttaa acataactac    360
aggagagtta ccaaatacaa agttctgttc tcctttcgtt ctcttctttc ttttcttttt    420
gcctgagtca gacatcaaat agcttcgatt tgcattatcc gttggaatgt atcaaaatca    480
atatcaaaat caataagatg aaagatgtac aatccaattt ctcgattcaa tagaagccca    540
aggaggtgca agana                                                    555
```

<210> SEQ ID NO 60
<211> LENGTH: 555
<212> TYPE: DNA
<213> ORGANISM: x Triticosecale
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (552)..(554)
<223> OTHER INFORMATION: n is a, c, g, or t

<400> SEQUENCE: 60

```
nnnnnnnnnn nnntnntttg atttctctga cattccatgt ttccgaaacg gatcctataa     60
aatatttcac tttttctatg atcatctcta ttttaggtat tcggggaatc ctccttaata    120
gacgaaatat tcttattatg tcaatgccaa ttgaatcaat gttattagct gtcaatttga    180 acttttggt attttccgtt tctttggatg atatgatggg tcaatcattt gcttcattag    240
ttccaacagt ggcagctgcg gaatctgcta ttggattagc cattttcgtt attacttttc    300
gagtccgagg gactattgct gtcgaatcta taaattgcat tcaaggttaa acataactac    360
aggagagtta ccaaatacaa agttctgttc tcctttcgtt ctcttctttc ttttcttttt    420
gcctgagtca gacatcaaat agcttcgatt tgcattatcc gttggaatgt atcaaaatca    480
atatcaaaat caataagatg aaagatgtac aatccaattt ctcgattcaa tagaagccca    540
aggaggtgca annna                                                    555
```

<210> SEQ ID NO 61
<211> LENGTH: 558
<212> TYPE: DNA
<213> ORGANISM: x Triticosecale
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(18)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (557)..(557)
<223> OTHER INFORMATION: n is a, c, g, or t

<400> SEQUENCE: 61
nnnnnnnnna nntnnnnntt tgatttctct gacattccat gtttccgaaa cggatcctat    60
aaaatatttc acttttttcta tgatcatctc tattttaggt attcggggaa tcctccttaa   120
tagacgaaat attcttatta tgtcaatgcc aattgaatca atgttattag ctgtcaattt   180 gaacttttg gtattttccg tttctttgga tgatatgatg ggtcaatcat ttgcttcatt   240
agttccaaca gtggcagctg cggaatctgc tattggatta gccatttcg ttattacttt   300 tcgagtccga gggactattg ctgtcgaatc tataaattgc attcaaggtt aaacataact   360
acaggagagt taccaaatac aaagttctgt tctcctttcg ttctcttctt tcttttcttt   420
ttgcctgagt cagacatcaa atagcttcga tttgcattat ccgttggaat gtatcaaaat   480
caatatcaaa atcaataaga tgaaagatgt acaatccaat ttctcgattc aatagaagcc   540
caaggaaggt gcaanana                                                 558

<210> SEQ ID NO 62
<211> LENGTH: 555
<212> TYPE: DNA
<213> ORGANISM: x Triticosecale
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (530)..(531)
<223> OTHER INFORMATION: n is a, c, g, or t
<220> FEATURE:
<221> NAME/KEY: misc_feature
<222> LOCATION: (550)..(551)
<223> OTHER INFORMATION: n is a, c, g, or t

<400> SEQUENCE: 62

```
nnnnnnnnnn nnnnnnatnn ntngatttct ctgacnttcc ntgtttccga aacggatcct      60
ataaaatatt tcacttttnn tnngatcatc tctattttag gtattcgggg aatcctcctt     120
aatagacgaa atattcttat tatgtcaatg ccaattgaat caatgttatt agctgtcaat     180
ttgaactttt tggnatttc  cgtttctttg gatgatatga tgggtcaatc atttgcttca     240
ttagttccaa cagtggcagc tgcggaatct gctattggat tagccatttt cgttattact     300
tttcgagtcc gagggactat tgctgtcgaa tctataaatt gcattcaagg ttaaacataa     360
ctacaggaga gttaccaaat acaaagttct gttctccttt cgttctcttc tttcttttct     420
ttttgcctga gtcagacatc aaatagcttc gatttgcatt atccgttgga atgtatcaaa     480
atcaatatca aaatcaataa gatgaaagat gtacaatcca atntctcgan ncaatagaag     540
cccaaagagn ngcaa                                                     555

<210> SEQ ID NO 63
<211> LENGTH: 554
<212> TYPE: DNA
<213> ORGANISM: x Triticosecale
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 63
nnnnnnnnnn nnntnntttg anttctctga cattccatgt ttccgaaacg gatcctataa      60
aatatttcac tttttctatg atcatctcta ttttaggtat tcggggaatc ctccttaata     120
gacgaaatat tcttattatg tcaatgccaa ttgaatcaat gttattagct gtcaatttga     180 acttttggt  attttccgtt tctttggatg atatgatggg tcaatcattt gcttcattag     240
ttccaacagt ggcagctgcg gaatctgcta ttggattagc catttcgtt  attacttttc     300 gagtccgagg gactattgct gtcgaatcta taaattgcat tcaaggttaa acataactac     360
aggagagtta ccaaatacaa agttctgttc cctttcgtt  ctcttctttc ttttcttttt     420
gcctgagtca gacatcaaat agcttcgatt tgcattatcc gttggaatgt atcaaaatca     480
atatcaaaat caataagatg aaagatgtac aatccaattt ctcgattcaa tagaagccca     540
aggaggtgca aaag                                                      554

<210> SEQ ID NO 64
<211> LENGTH: 558
<212> TYPE: DNA
<213> ORGANISM: x Triticosecale
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
```

```
<222> LOCATION: (29)..(29)
<223> OTHER INFORMATION: n is a, c, g, or t
<220> FEATURE:
<221> NAME/KEY: misc_feature
<222> LOCATION: (31)..(37)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (77)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (304)..(305)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
```

```
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (349)..(352)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (461)..(463)
<223> OTHER INFORMATION: n is a, c, g, or t
<220> FEATURE:
<221> NAME/KEY: misc_feature
<222> LOCATION: (481)..(486)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t
<220> FEATURE:
<221> NAME/KEY: misc_feature
<222> LOCATION: (527)..(528)
<223> OTHER INFORMATION: n is a, c, g, or t
```

<220> FEATURE:
<221> NAME/KEY: misc_feature
<222> LOCATION: (533)..(533)
<223> OTHER INFORMATION: n is a, c, g, or t
<220> FEATURE:
<221> NAME/KEY: misc_feature
<222> LOCATION: (535)..(537)
<223> OTHER INFORMATION: n is a, c, g, or t
<220> FEATURE:
<221> NAME/KEY: misc_feature
<222> LOCATION: (552)..(553)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t

<400> SEQUENCE: 64

| | | | | | |
|---|---|---|---|---|---|
| nnnnnnnnnn | nnnnnnnnnn | tctgntntnt | nnnnnnngtc | nnaataagca | cntatgctcn | 60 |
| gnataatact | tttcctnnnn | nnnnanntta | acgnancgga | attggaacct | agcatcctgg | 120 |
| nntctatacc | gaattcaaca | cgagagcatg | cngccgatcc | tggatacatc | actatataaa | 180 |
| gtgtgcntgc | attgttggat | ctttattggt | agccagtctt | tcacgtctgc | ccctccgctc | 240 |
| ccatnccttt | cttgttcgga | ccnacccaac | cggggatgtg | cgacgagtct | ntctgnttag | 300 |
| ngcnngaagc | ggaaccnaaa | tnaagctntc | tttatttgna | tttatggann | nnccatccat | 360 |
| tttccaatat | agttgggana | ttttaaccaa | naaattggga | cataaaatgt | tnagatcgga | 420 |
| acatgggaat | agatctnatn | ccaanactgn | ctacccattt | nnnttggtgg | gctttctaaa | 480 |
| nnnnnntacc | tctacaaggg | ntccnagntn | cgatctntat | ttncggnntg | gancnnnccc | 540 |
| ctcaaaaaag | annaattn | | | | | 558 |

<210> SEQ ID NO 65
<211> LENGTH: 471
<212> TYPE: DNA
<213> ORGANISM: Triticum aestivum

<400> SEQUENCE: 65

| | | | | | |
|---|---|---|---|---|---|
| atgcctcaac | ttgataaatt | aacttatttc | tcacaattct | tctggttatg | tcttctcctc | 60 |
| tttactttt | atattctctt | atttaataat | aataatggaa | tacttggaat | tagtagaatt | 120 |
| ctcaaactac | ggaaccaact | gctttcgcac | cggggggggcg | agatccggag | caaggaccct | 180 |
| aagaatctgg | aagatatctc | gagaaaaggt | tttagcaccg | gtctctcata | tatgtactcc | 240 |
| agtttatccg | aagtatccca | atggtgtaag | accgtcgact | atttgggaaa | aaggaggaaa | 300 |
| atcactctga | tctctgattt | cggagaaata | agtggctcac | gaggaatgga | gagacagatt | 360 |
| ctctatttga | tctcgaagtc | ctcatataac | acttcttcca | gtcggatcac | ttgttggaaa | 420 |
| aacataatgc | tcacacatgt | tccacacggg | caaggaagca | taatatcatg | a | 471 |

<210> SEQ ID NO 66
<211> LENGTH: 471
<212> TYPE: DNA
<213> ORGANISM: x Triticosecale
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (93)..(93)

```
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (163)..(164)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (200)..(202)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (226)..(230)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (261)..(262)
<223> OTHER INFORMATION: n is a, c, g, or t
<220> FEATURE:
<221> NAME/KEY: misc_feature
<222> LOCATION: (267)..(268)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (305)..(307)
<223> OTHER INFORMATION: n is a, c, g, or t
<220> FEATURE:
<221> NAME/KEY: misc_feature
```

```
<222> LOCATION: (309)..(310)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (316)..(317)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (340)..(341)
<223> OTHER INFORMATION: n is a, c, g, or t
<220> FEATURE:
<221> NAME/KEY: misc_feature
<222> LOCATION: (350)..(354)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (373)..(375)
<223> OTHER INFORMATION: n is a, c, g, or t
<220> FEATURE:
<221> NAME/KEY: misc_feature
<222> LOCATION: (385)..(386)
<223> OTHER INFORMATION: n is a, c, g, or t
<220> FEATURE:
<221> NAME/KEY: misc_feature
<222> LOCATION: (391)..(392)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (409)..(410)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (435)..(440)
<223> OTHER INFORMATION: n is a, c, g, or t
<220> FEATURE:
```

<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (456)..(458)
<223> OTHER INFORMATION: n is a, c, g, or t
<220> FEATURE:
<221> NAME/KEY: misc_feature
<222> LOCATION: (460)..(461)
<223> OTHER INFORMATION: n is a, c, g, or t
<220> FEATURE:
<221> NAME/KEY: misc_feature
<222> LOCATION: (464)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t

<400> SEQUENCE: 66

```
atgcctcanc ttgataaatt aacttatttc ncacaattct tctggttatg tcttcccccc      60
tttactttt atattcccct atttaaaaat aanaatggaa tacttggaat tagnagaatt      120
ctcaaactac ggaaccaact gctttcgcnc cggggggggg ggnnccggng cagggcccct      180
aaaaattngg aaaattttn nngaaaaggt tttagccccg gnntcnnnnn tntntccccc      240
ngtttntccn aagtntccca nngggggnnan accgtcgnct ttttgggaaa aaggggggaaa   300
atccnnntnn tctntnnttt cggaaaaaaa aggggcnccn ngggaagggn nnnncaaatt    360
ctnttttga tcnnaagcc ctcanntaac nnttntnccn gccggancnn ttgttggaaa      420
aacanaangn tcncnnnnnn cccncncggg naaggnnncn naanntctg a               471
```

<210> SEQ ID NO 67
<211> LENGTH: 864
<212> TYPE: DNA
<213> ORGANISM: Triticum aestivum

<400> SEQUENCE: 67

```
atgctctgta taatactttt ccccgagcga tggtttagcg gattcggaat tgtaaccaag      60
catcctgggt tctatacccg attcaacact agagcatgca gccgatcctg gatacataac     120
tctaaaaagt gtgtgtgcag ttttggatct ttattggtag ccagtctttc acttctgcct     180
ctccactccc atgcctttct tggtcggacc aacccaaccg gcgatttccg acaagtcttt     240
ctgcttagag caagaagcgg aaccaaaata aagctttctt tatttcatt tatggataac     300
caatccattt tccaatatag ttgggagatt ttacccaaga atgggtaca taaaatgaaa      360
agatcggaac atgggaatag atcttatacc aatactgact acccatttcc attgttgtgc    420
tttctaaaat ggcataccta tacaagggtt caagtttcga tcgatatttg cggagtggat    480
catccctctc gaaaacgaag atttgaagtt gtccataatt tactgagtac tcggtataac    540
tcacgcattc gtgtacaaac aagtgcagac gaagtaacac gaatatctcc ggtagtcagt    600
ctatttccat cagccggccg gtgggagcga gaagtatggg atatgtctgg tgtttcttcc    660
atcaatcatc cggatttacg ccgtatatca acagattatg gtttcgaggg tcatccatta    720
cgaaaagact ttcctctgag tggatatgtg gaagtacgct atgatgatcc agagaaacgt    780
```

```
gtggtttctg aacccattga gatgacccaa gaatttcgct atttcgattt tgctagtcct      840
tgggaacagc gtagcgacgg ataa                                             864
```

<210> SEQ ID NO 68
<211> LENGTH: 864
<212> TYPE: DNA
<213> ORGANISM: x Triticosecale

<400> SEQUENCE: 68

```
atgctctgta taatactttt ccccgagcga tggtttagcg gattcggaat tgtaaccaag       60
catcctgggt tctatacccg attcaacact agagcatgca gccgatcctg gatacatcac      120
tatataaagt gtgcatgcag ttttggatct ttattggtag ccagtctttc acttctgcct      180
ctccactccc atgcctttct tggtcggacc aacccaaccg gcgatttccg acaagtcttt      240
ctgcttagag caagaagcgg aaccaaaata aagctttctt tatttgcatt tatggataac      300
caatccattt tccaatatag ttgggagatt ttacccaaga aatgggtaca taaaatgaaa      360
agatcggaac atgggaatag atcttatacc aatactgact acccatttcc attgttgtgc      420
tttctaaaat ggcataccta tacaagggtt caagttttcga tcgatatttg cggagtggat      480
catccctctc gaaaacgaag atttgaagtt gtccataatt tactgagtac tcggtataac      540
tcacgcattc gtgtacaaac aagtgcagac gaagtaacac gaatatctcc ggtagtcagt      600
ctatttccat cagccggccg gtgggagcga gaagtatggg atatgtctgg tgtttcttcc      660
atcaatcatc cggatttacg ccgtatatca acagattatg gtttcgaggg tcatccatta      720
cgaaaagact ttcctctgag tggatatgtg gaagtacgct atgatgatcc agagaaacgt      780
gtggtttctg aacccattga gatgacccaa gaatttcgct atttcgattt tgctagtcct      840
tgggaacagc gtagcgacgg ataa                                             864
```

<210> SEQ ID NO 69
<211> LENGTH: 156
<212> TYPE: PRT
<213> ORGANISM: Triticum aestivum

<400> SEQUENCE: 69

```
Met Pro Gln Leu Asp Lys Leu Thr Tyr Phe Ser Gln Phe Phe Trp Leu
1               5                   10                  15

Cys Leu Leu Leu Phe Thr Phe Tyr Ile Leu Leu Phe Asn Asn Asn Asn
                20                  25                  30

Gly Ile Leu Gly Ile Ser Arg Ile Leu Lys Leu Arg Asn Gln Leu Leu
            35                  40                  45

Ser His Arg Gly Gly Glu Ile Arg Ser Lys Asp Pro Lys Asn Leu Glu
        50                  55                  60

Asp Ile Ser Arg Lys Gly Phe Ser Thr Gly Leu Ser Tyr Met Tyr Ser
65                  70                  75                  80

Ser Leu Ser Glu Val Ser Gln Trp Cys Lys Thr Val Asp Tyr Leu Gly
                85                  90                  95

Lys Arg Arg Lys Ile Thr Leu Ile Ser Asp Phe Gly Glu Ile Ser Gly
                100                 105                 110

Ser Arg Gly Met Glu Arg Gln Ile Leu Tyr Leu Ile Ser Lys Ser Ser
            115                 120                 125

Tyr Asn Thr Ser Ser Ser Arg Ile Thr Cys Trp Lys Asn Ile Met Leu
        130                 135                 140

Thr His Val Pro His Gly Gln Gly Ser Ile Ile Ser
```

145          150          155

<210> SEQ ID NO 70
<211> LENGTH: 156
<212> TYPE: PRT
<213> ORGANISM: x Triticosecale
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (74)..(78)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (87)..(90)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (102)..(106)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (117)..(118)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid -continued

```
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (131)..(134)
<223> OTHER INFORMATION: Xaa can be any naturally occurring amino acid
<220> FEATURE:
<221> NAME/KEY: misc_feature
<222> LOCATION: (136)..(137)
<223> OTHER INFORMATION: Xaa can be any naturally occurring amino acid
<220> FEATURE:
<221> NAME/KEY: misc_feature
<222> LOCATION: (142)..(149)
<223> OTHER INFORMATION: Xaa can be any naturally occurring amino acid
<220> FEATURE:
<221> NAME/KEY: misc_feature
<222> LOCATION: (151)..(156)
<223> OTHER INFORMATION: Xaa can be any naturally occurring amino acid

<400> SEQUENCE: 70

Met Pro Xaa Leu Asp Lys Leu Thr Tyr Phe Xaa Gln Phe Phe Trp Leu
1               5                   10                  15

Cys Leu Pro Pro Phe Thr Phe Tyr Ile Pro Leu Phe Lys Asn Xaa Asn
                20                  25                  30

Gly Ile Leu Gly Ile Xaa Arg Ile Leu Lys Leu Arg Asn Gln Leu Leu
            35                  40                  45

Ser Xaa Arg Gly Gly Xaa Arg Xaa Arg Ala Pro Lys Asn Xaa Glu
50                  55                  60

Asn Phe Xaa Xaa Lys Gly Phe Ser Pro Xaa Xaa Xaa Xaa Ser Pro
65                  70                  75                  80

Xaa Xaa Ser Xaa Xaa Ser Xaa Xaa Xaa Thr Val Xaa Phe Leu Gly
                85                  90                  95

Lys Arg Gly Lys Ile Xaa Xaa Xaa Xaa Phe Gly Lys Lys Arg Gly
            100                 105                 110

Xaa Xaa Gly Arg Xaa Xaa Gln Ile Xaa Phe Leu Ile Xaa Lys Pro Ser
        115                 120                 125

Xaa Asn Xaa Xaa Xaa Xaa Arg Xaa Xaa Cys Trp Lys Asn Xaa Xaa Xaa
    130                 135                 140

Xaa Xaa Xaa Xaa Xaa Gly Xaa Xaa Xaa Xaa Xaa Xaa
145                 150                 155

<210> SEQ ID NO 71
<211> LENGTH: 287
<212> TYPE: PRT
<213> ORGANISM: Triticum aestivum

<400> SEQUENCE: 71

Met Leu Cys Ile Ile Leu Phe Pro Glu Arg Trp Phe Ser Gly Phe Gly
1               5                   10                  15

Ile Val Thr Lys His Pro Gly Phe Tyr Thr Arg Phe Asn Thr Arg Ala
                20                  25                  30

Cys Ser Arg Ser Trp Ile His Asn Ser Lys Lys Cys Val Cys Ser Phe
            35                  40                  45

Gly Ser Leu Leu Val Ala Ser Leu Ser Leu Pro Leu His Ser His
50                  55                  60

Ala Phe Leu Gly Arg Thr Asn Pro Thr Gly Asp Phe Arg Gln Val Phe
65                  70                  75                  80
```

```
Leu Leu Arg Ala Arg Ser Gly Thr Lys Ile Lys Leu Ser Leu Phe Ser
            85                  90                  95

Phe Met Asp Asn Gln Ser Ile Phe Gln Tyr Ser Trp Glu Ile Leu Pro
            100                 105                 110

Lys Lys Trp Val His Lys Met Lys Arg Ser Glu His Gly Asn Arg Ser
            115                 120                 125

Tyr Thr Asn Thr Asp Tyr Pro Phe Pro Leu Leu Cys Phe Leu Lys Trp
            130                 135                 140

His Thr Tyr Thr Arg Val Gln Val Ser Ile Asp Ile Cys Gly Val Asp
145                 150                 155                 160

His Pro Ser Arg Lys Arg Phe Glu Val Val His Asn Leu Leu Ser
            165                 170                 175

Thr Arg Tyr Asn Ser Arg Ile Arg Val Gln Thr Ser Ala Asp Glu Val
            180                 185                 190

Thr Arg Ile Ser Pro Val Val Ser Leu Phe Pro Ser Ala Gly Arg Trp
            195                 200                 205

Glu Arg Glu Val Trp Asp Met Ser Gly Val Ser Ser Ile Asn His Pro
            210                 215                 220

Asp Leu Arg Arg Ile Ser Thr Asp Tyr Gly Phe Glu Gly His Pro Leu
225                 230                 235                 240

Arg Lys Asp Phe Pro Leu Ser Gly Tyr Val Glu Val Arg Tyr Asp Asp
            245                 250                 255

Pro Glu Lys Arg Val Val Ser Glu Pro Ile Glu Met Thr Gln Glu Phe
            260                 265                 270

Arg Tyr Phe Asp Phe Ala Ser Pro Trp Glu Gln Arg Ser Asp Gly
            275                 280                 285

<210> SEQ ID NO 72
<211> LENGTH: 287
<212> TYPE: PRT
<213> ORGANISM: x Triticosecale

<400> SEQUENCE: 72

Met Leu Cys Ile Ile Leu Phe Pro Glu Arg Trp Phe Ser Gly Phe Gly
1               5                   10                  15

Ile Val Thr Lys His Pro Gly Phe Tyr Thr Arg Phe Asn Thr Arg Ala
            20                  25                  30

Cys Ser Arg Ser Trp Ile His His Tyr Ile Lys Cys Ala Cys Ser Phe
            35                  40                  45

Gly Ser Leu Leu Val Ala Ser Leu Ser Leu Leu Pro Leu His Ser His
            50                  55                  60

Ala Phe Leu Gly Arg Thr Asn Pro Thr Gly Asp Phe Arg Gln Val Phe
65                  70                  75                  80

Leu Leu Arg Ala Arg Ser Gly Thr Lys Ile Lys Leu Ser Leu Phe Ala
            85                  90                  95

Phe Met Asp Asn Gln Ser Ile Phe Gln Tyr Ser Trp Glu Ile Leu Pro
            100                 105                 110

Lys Lys Trp Val His Lys Met Lys Arg Ser Glu His Gly Asn Arg Ser
            115                 120                 125

Tyr Thr Asn Thr Asp Tyr Pro Phe Pro Leu Leu Cys Phe Leu Lys Trp
            130                 135                 140
```

```
His Thr Tyr Thr Arg Val Gln Val Ser Ile Asp Ile Cys Gly Val Asp
145                 150                 155                 160

His Pro Ser Arg Lys Arg Arg Phe Glu Val Val His Asn Leu Leu Ser
                165                 170                 175

Thr Arg Tyr Asn Ser Arg Ile Arg Val Gln Thr Ser Ala Asp Glu Val
            180                 185                 190

Thr Arg Ile Ser Pro Val Val Ser Leu Phe Pro Ser Ala Gly Arg Trp
        195                 200                 205

Glu Arg Glu Val Trp Asp Met Ser Gly Val Ser Ser Ile Asn His Pro
    210                 215                 220

Asp Leu Arg Arg Ile Ser Thr Asp Tyr Gly Phe Glu Gly His Pro Leu
225                 230                 235                 240

Arg Lys Asp Phe Pro Leu Ser Gly Tyr Val Glu Val Arg Tyr Asp Asp
                245                 250                 255

Pro Glu Lys Arg Val Val Ser Glu Pro Ile Glu Met Thr Gln Glu Phe
            260                 265                 270

Arg Tyr Phe Asp Phe Ala Ser Pro Trp Glu Gln Arg Ser Asp Gly
        275                 280                 285
```